United States Patent
Bentsen et al.

(12) 
(10) Patent No.: US 6,208,880 B1
(45) Date of Patent: Mar. 27, 2001

(54) BLOOD PARAMETER MEASUREMENT DEVICE

(75) Inventors: James G. Bentsen, North St. Paul, MN (US); Stanley O. Heinemann, Trabuco Canyon, CA (US); Gary W. Lee, Long Beach, CA (US); Thomas G. Hacker, Anaheim, CA (US); N. Alan Abul-Haj; Roxanne E. Abul-Haj, both of Lake Forest, CA (US)

(73) Assignee: Terumo Cardiovascular Systems Corporation, Somerset, NJ (US)

( * ) Notice: Subject to any disclaimer, the term of this patent is extended or adjusted under 35 U.S.C. 154(b) by 0 days.

(21) Appl. No.: 09/455,166

(22) Filed: Dec. 6, 1999

(Under 37 CFR 1.47)

Related U.S. Application Data

(62) Division of application No. 08/810,955, filed on Feb. 27, 1997, now Pat. No. 6,009,339.

(51) Int. Cl.⁷ .................................................. A61B 5/00
(52) U.S. Cl. .......................... 600/322; 356/410; 422/68.1
(58) Field of Search ...................................... 600/310, 322, 600/326; 356/39, 41, 244, 410, 411; 422/44, 55, 68.1, 102, 104; 436/63, 66, 68, 172

(56) References Cited

U.S. PATENT DOCUMENTS

| Re. 31,879 | 5/1985 | Lubbers et al. . |
|---|---|---|
| 3,639,829 | 2/1972 | Harnoncourt . |
| 3,639,830 | 2/1972 | Harnoncourt . |
| 3,718,568 | 2/1973 | Neuwelt . |
| 3,799,672 | 3/1974 | Vurek . |
| 3,826,730 | 7/1974 | Watanabe et al. . |
| 4,041,932 | 8/1977 | Fostick . |
| 4,338,174 | 7/1982 | Tamura . |
| 4,401,547 | 8/1983 | Schinkmann et al. . |
| 4,447,150 | 5/1984 | Heinemann . |
| 4,557,900 | 12/1985 | Heitzmann . |
| 4,577,109 | 3/1986 | Hirschfeld . |
| 4,640,820 | 2/1987 | Cooper . |

(List continued on next page.)

FOREIGN PATENT DOCUMENTS

| 26 30 606 | 12/1978 | (DE) . |
|---|---|---|
| 376 168 | 7/1990 | (EP) . |
| 380 664 | 8/1990 | (EP) . |
| 399 227 | 11/1990 | (EP) . |
| 0 56 83 80 | 11/1993 | (EP) . |
| 575 712 | 12/1993 | (EP) . |
| 0 585 212 | 3/1994 | (EP) . |
| 0 705 610 | 10/1996 | (EP) . |
| WO 87/04914 | 8/1987 | (WO) . |
| WO 92/21281 | 12/1992 | (WO) . |
| WO 93/06775 | 4/1993 | (WO) . |
| WO 96/07268 | 3/1996 | (WO) . |
| WO 96/10747 | 4/1996 | (WO) . |
| WO 96/22730 | 8/1996 | (WO) . |
| WO 98/37800 | 9/1998 | (WO) . |

OTHER PUBLICATIONS

"CDI Blood Gas Monitoring System 400", 3M Health Care Operator's Manual (undated), pp. 3–24 and 31–44.

*Primary Examiner*—Eric F. Winakur
(74) *Attorney, Agent, or Firm*—Burns, Doane, Swecker & Mathis, LLP

(57) ABSTRACT

A blood parameter measurement device especially useful for surgical procedures includes a compact housing with a light source, light detector and signal converter contained within the housing. In use, the device is releasably coupled to a cassette that can be either used as an in-line cell in series with a cardiopulmonary by-pass circuit, or in another passageway that shunts the cardiopulmonary by-pass circuit. Preferably, the housing of the device has a longitudinal axis that extends in a direction generally parallel to the direction of blood flowing through the cassette.

11 Claims, 28 Drawing Sheets

U.S. PATENT DOCUMENTS

| | | |
|---|---|---|
| 4,640,826 | 2/1987 | Williams et al. . |
| 4,745,279 | 5/1988 | Karkar et al. . |
| 4,786,474 | 11/1988 | Cooper . |
| 4,798,738 | 1/1989 | Yafuso et al. . |
| 4,824,789 | 4/1989 | Yafsuo et al. . |
| 4,830,013 | 5/1989 | Maxwell . |
| 4,849,172 | 7/1989 | Yafuso et al. . |
| 4,867,919 | 9/1989 | Yafuso et al. . |
| 4,886,338 | 12/1989 | Yafuso et al. . |
| 4,895,156 | 1/1990 | Schulze . |
| 4,919,891 | 4/1990 | Yafuso et al. . |
| 4,929,561 | 5/1990 | Hirschfield . |
| 4,938,218 | 7/1990 | Goodman et al. . |
| 4,951,669 | 8/1990 | Maxwell et al. . |
| 4,989,606 | 2/1991 | Gehrich et al. . |
| 4,999,306 | 3/1991 | Yafuso et al. . |
| 5,006,314 | 4/1991 | Gourley et al. . |
| 5,043,285 | 8/1991 | Surgi . |
| 5,048,525 | 9/1991 | Maxwell . |
| 5,053,520 | 10/1991 | Bieniarz et al. . |
| 5,057,278 | 10/1991 | Maxwell et al. . |
| 5,081,041 | 1/1992 | Yafuso et al. . |
| 5,081,042 | 1/1992 | Yafuso et al. . |
| 5,094,820 | 3/1992 | Maxwell et al. . |
| 5,102,625 | 4/1992 | Milo . |
| 5,104,623 | 4/1992 | Miller . |
| 5,127,077 | 6/1992 | Iyer et al. . |
| 5,128,019 | 7/1992 | Karpf et al. . |
| 5,132,057 | 7/1992 | Tomisaka et al. . |
| 5,134,998 | 8/1992 | Tusa et al. . |
| 5,136,033 | 8/1992 | Masilamani et al. . |
| 5,154,890 | 10/1992 | Mauze et al. . |
| 5,162,525 | 11/1992 | Masilamani et al. . |
| 5,171,029 | 12/1992 | Maxwell et al. . |
| 5,175,016 | 12/1992 | Yafuso et al. . |
| 5,176,882 | 1/1993 | Gray et al. . |
| 5,272,088 | 12/1993 | Morlotti . |
| 5,272,090 | 12/1993 | Gavish et al. . |
| 5,278,072 | 1/1994 | Wall et al. . |
| 5,279,793 | 1/1994 | Glass . |
| 5,289,255 | 2/1994 | Mullin et al. . |
| 5,291,884 | 3/1994 | Heinermann et al. . |
| 5,296,381 | 3/1994 | Yafuso et al. . |
| 5,304,492 | 4/1994 | Klinkhammer . |
| 5,348,706 | 9/1994 | Abul-Haj et al. . |
| 5,377,287 | 12/1994 | Lee et al. . |
| 5,403,746 | 4/1995 | Bentsen et al. . |
| 5,409,666 | 4/1995 | Nagel et al. . |
| 5,453,248 | 9/1995 | Olstein . |
| 5,461,476 | 10/1995 | Fournier . |
| 5,462,879 | 10/1995 | Bentsen . |
| 5,462,880 | 10/1995 | Kane et al. . |
| 5,464,587 | 11/1995 | Kippitsch et al. . |
| 5,474,743 | 12/1995 | Trend et al. . |
| 5,480,723 | 1/1996 | Klainer et al. . |
| 5,498,549 | 3/1996 | Nagel et al. . |
| 5,508,509 | 4/1996 | Yafuso et al. . |
| 5,517,313 | 5/1996 | Colvin, Jr. . |
| 5,518,694 | 5/1996 | Bentsen . |
| 5,525,520 | 6/1996 | Dinh . |
| 5,580,527 | 12/1996 | Bell et al. . |
| 5,591,400 | 1/1997 | Dektar et al. . |
| 5,822,137 | 10/1998 | Abul-Haj et al. . |
| 5,958,782 | 9/1999 | Bentsen et al. . |

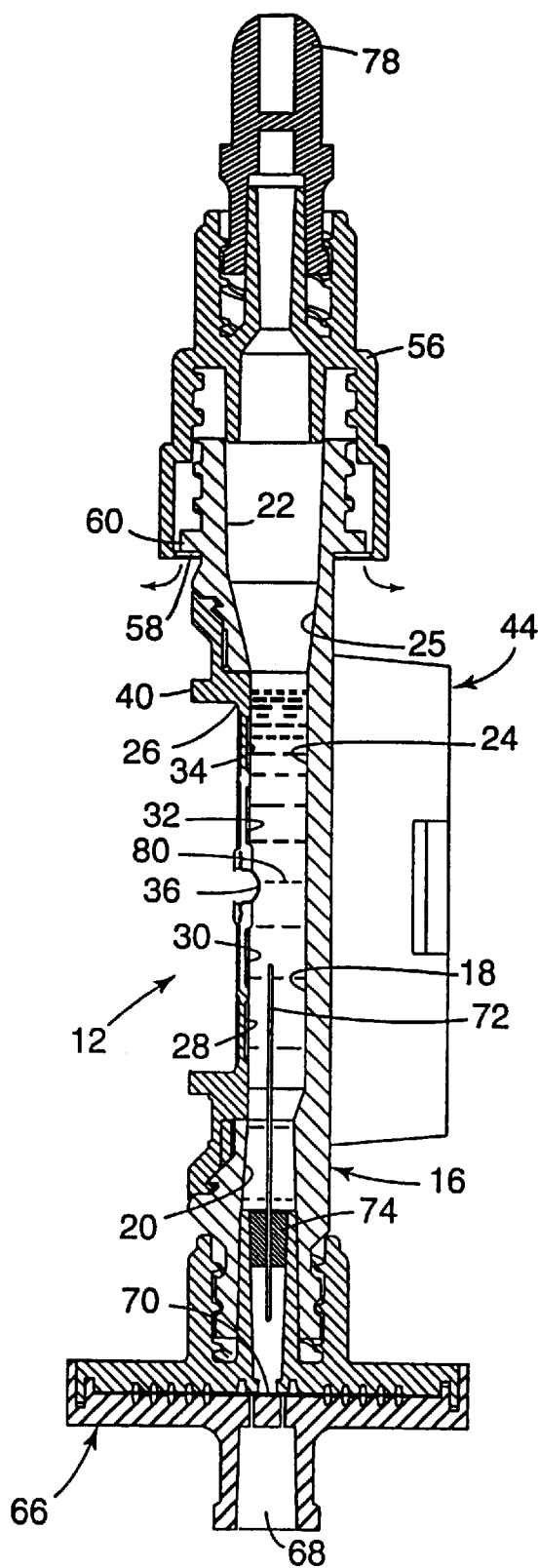
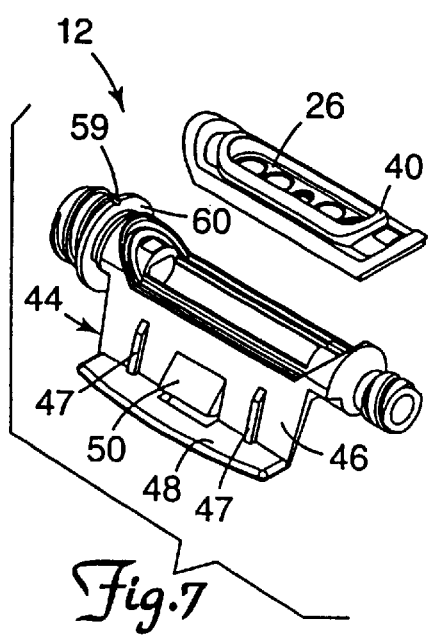
Fig.6
Fig.7

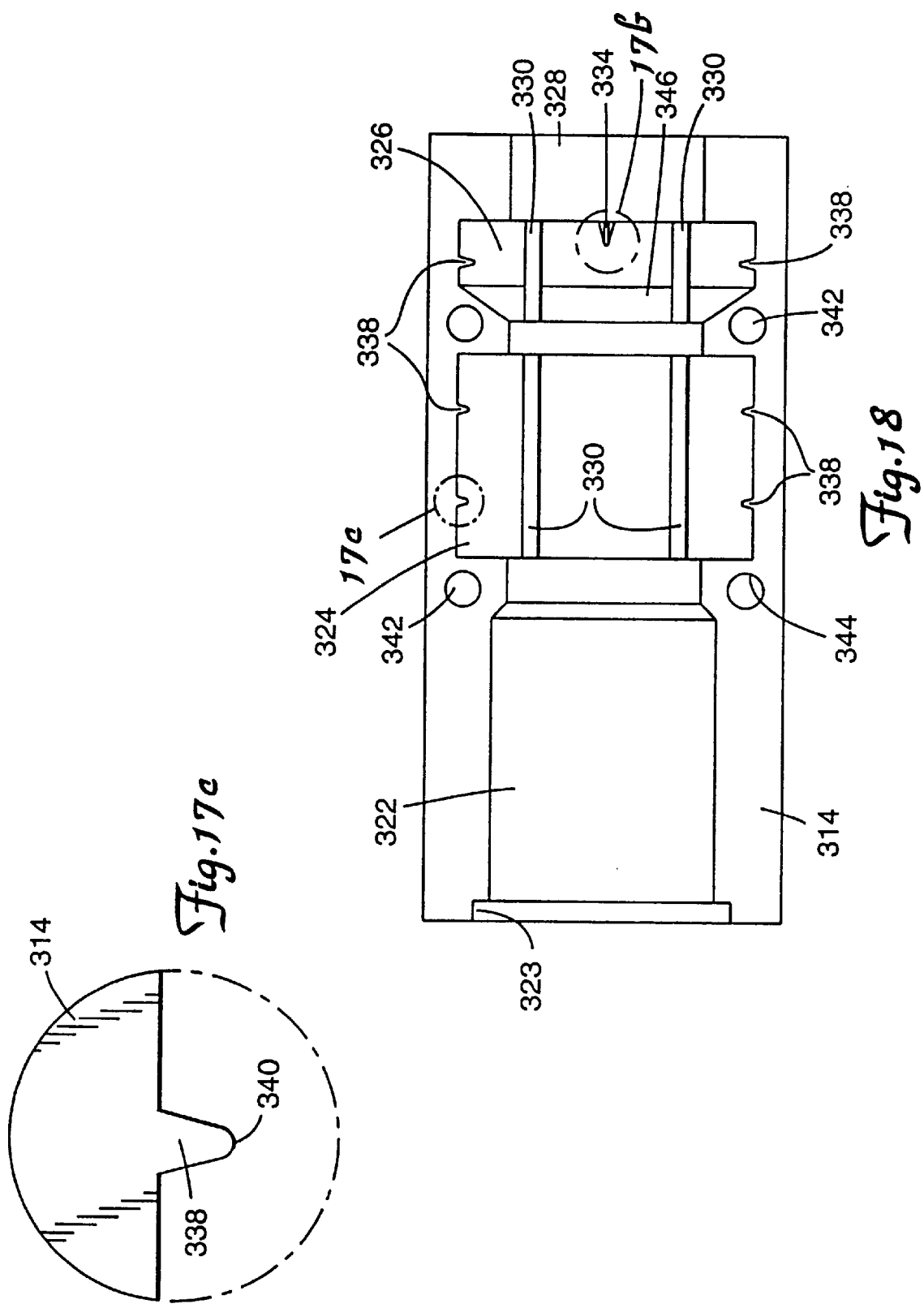

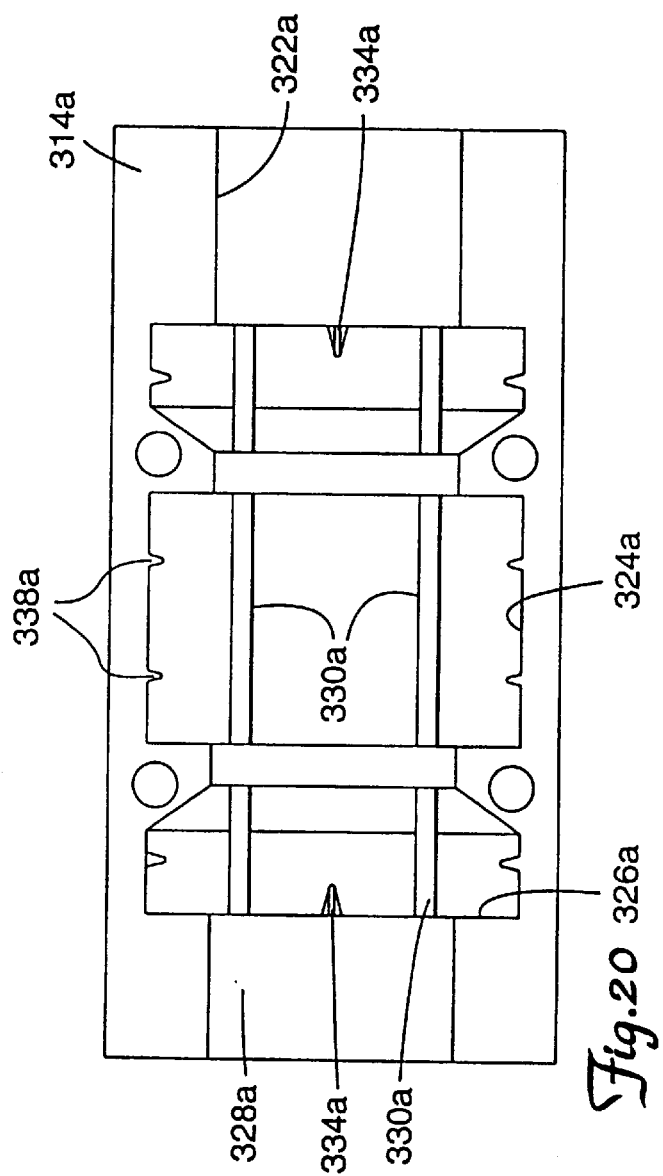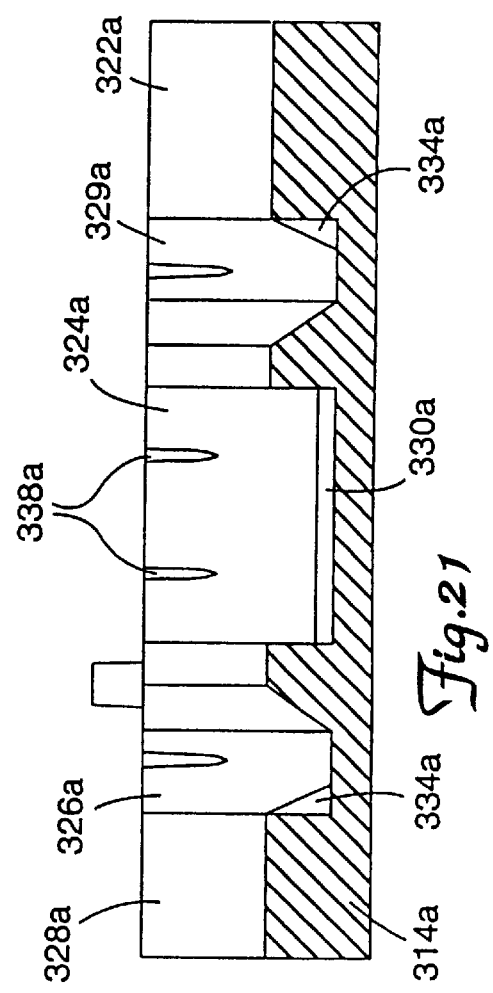

BLOOD PARAMETER MEASUREMENT DEVICE

This application is a divisional, of application Ser. No. 08/810,955, filed Feb. 27, 1997, now U.S. Pat. No. 6,009,339.

BACKGROUND OF THE INVENTION

1. Field of the Invention

This invention broadly relates to a device for measuring one or more parameters of blood, and is especially suitable for use during surgical procedures.

2. Description of the Related Art

Various characteristics or parameters of blood are often monitored in real time during certain surgical procedures. For example, during open heart surgery the surgeon and other members of the surgical team often monitor the pH of the patient's blood as well as the concentration of certain blood gases such as carbon dioxide and oxygen. In many instances, the parameters of the patient's blood are monitored not only as the surgery is progressing, but also in the time period before and after the surgical procedure. In addition, the potassium ion is used to stop the heart during open heart surgery and as a consequence the potassium ion must be monitored periodically during the procedure.

Measurement of blood parameters is often accomplished using an extracorporeal blood circuit having lengths of flexible tubing with passageways that are in fluid communication with the vascular system of the patient. In many extracorporeal blood circuits, one or more sensors that are useful for determining blood parameters are placed adjacent the passageway and are connected to a processing unit. The processing unit is typically connected to a display device such as a monitor so that the surgical team can review the parameters of interest when desired. Optionally, the processing unit is connected to a recording device such as a printer to provide a log of the parameters over a period of time.

Optical sensors are often used for sensing blood parameters in real time. For example, U.S. Pat. No. Re. 31,879 to Lubbers et al. and U.S. Pat. No. 5,403,746 to Bentsen et al. describe fluorescent sensors that respond to light in accordance to the partial pressure of oxygen, the partial pressure of carbon dioxide and the pH of blood. U.S. Pat. No. 5,162,525 to Masilamani et al. and U.S. Pat. No. 5,474,743 to Trend et al. Describe fluorescent sensors that respond to the potassium ion or other ions. Sensors that function on the principles of light absorbance are described, for example, in U.S. Pat. No. 4,041,932 to Fostick.

Optical sensors for measuring blood parameters are often optically coupled to a remote measuring device that includes a source of light for directing light to the sensors, apparatus for analyzing the light returned from the sensors and a monitor for providing a visual display of the measurement. In many systems, a bundle of optical fibers extends from the remote device to a transmission block or retainer, and a releasable coupling is provided to detachably connect the retainer or block to a cell or housing that supports the sensors. Such a system is shown, for example, in U.S. Pat. No. 4,989,606 to Gehrich et al. Unfortunately, the bundle of optical fibers in those systems is somewhat costly and may be damaged unless protected.

Extracorporeal blood circuits having sensors for determining blood parameters may be arranged in various manners, and the manner selected for use in a particular instance often depends upon the preferences of the surgical team. In some cases, the sensors are mounted in a housing located along a length of relatively small-diameter tubing that is connected at only one end to the patient's blood supply, and a device such as a syringe is used to draw a sample of blood past the sensors. Examples of such circuits are described in the aforementioned U.S. Pat. No. 4,989,606 to Gehrich et al.

Another type of extracorporeal blood circuit has sensors located along tubing that is part of an arterial or a venous passageway connected to an oxygenator. The sensors in this type of circuit are often connected to an element known as a flow-through cell that has fitting on opposite sides for coupling to the circuit tubing. Flow-through cells are described, for example, in U.S. Pat. No. 4,640,820 to Cooper.

While the systems mentioned above are generally satisfactory, there is a continuing need in the art to improve the convenience, accuracy and efficiency of conventional blood gas measuring devices. In addition, a system that is relatively compact and unobtrusive would be a particular advantage during many medical procedures.

SUMMARY OF THE INVENTION

The present invention in one aspect relates to a system for measuring one or more parameters of blood. The system includes a cassette having a chamber for receiving a quantity of blood and at least one light sensor. The system also includes a device having a housing with a coupling for releasable connection to the cassette. The device includes at least one light source that is fixed to the housing for directing light toward the at least one sensor. The device also includes at least one light detector fixed to the housing for detecting light from the at least one sensor. A signal converter is fixed to the housing and is connected to the at least one light detector. The signal converter provides a digital output signal that varies in response to the quantity of light detected by the at least one light detector.

Another aspect of the present invention is related to a device for measuring one or more parameters of blood. The device includes a housing having a coupling for releasable connection to a blood parameter measurement cassette having a sensor, a light source, and a first set of optical fibers that is optically coupled to the light source. The device also includes a first light detector and a second light detector, an optical reference material, and a second set of optical fibers optically coupled to the first light detector and the second light detector. The first set includes a first group of optical fibers to direct light from the light source to the sensor and a second group of optical fibers to direct light from the light source to the reference material. The second set includes a first group of optical fibers to direct light from the sensor to the first light detector and a second group of optical fibers to direct light from the reference material to the second light detector. A signal converter is connected to the first light detector and the second light detector and provides at least one output signal that varies in response to the quantity of light detected by the first light detector and the second light detector. The light source, the first light detector, the second light detector, the first set of optical fibers, the second set of optical fibers, the reference material and the signal converter are all contained within the housing.

The present invention also concerns a device for measuring one or more parameters of blood. The device includes a housing having a coupling for releasable connection to a blood parameter measurement cassette, at least one light source and a first plurality of optical fibers optically coupled to the at least one light source and extending toward the coupling for directing light toward the cassette. The first plurality of optical fibers has a certain cross-sectional area adjacent the coupling. The device also includes at least one light detector and a second plurality of optical fibers optically coupled to the at least one light detector and extending toward the coupling for receiving light from the cassette. The second plurality of optical fibers has a cross-sectional area adjacent the coupling that is in the range of about two to about four times the certain cross-sectional area of the first plurality.

In yet another aspect, the present invention is directed toward a system for measuring one or more parameters of blood. The system includes a device having an elongated housing with a coupling, at least one light source fixed to the housing and at least one light detector fixed to the housing. The system also includes a cassette having wall sections defining a chamber for receiving a quantity of blood. The cassette includes a coupling for releasably connecting the cassette to the device. The cassette includes at least one sensor connected to the wall sections for sensing at least one parameter of the blood in the chamber. The chamber includes an inlet port and an outlet port for enabling the flow of blood through the chamber along a certain path, and the certain path extends in a direction substantially parallel to the longitudinal axis of the housing.

The signal converter as set out in some of the embodiments mentioned above is an advantage, in that the output signal provided by the signal converter can be transmitted to a remote analyzer by means of, for example, an inexpensive electrical cable or by telemetry, and as such the fiber optic bundle associated with conventional blood parameter measurement devices is no longer necessary. In other embodiments as set out above, the parallel orientation of the device housing with respect to the path of blood flowing through the cassette provides a relatively compact arrangement that does not unduly restrict access to the patient during the procedure.

These and other aspects of the invention are further set out in the detailed description that follows as well as in the accompanying drawings.

BRIEF DESCRIPTION OF THE DRAWINGS

FIG. 6 is a view somewhat similar to FIG. 5 except that the measuring device is not shown and additional components have been connected to the cassette for calibration of sensors of the cassette;

FIG. 7 is an exploded, perspective view of the cassette alone that is shown in FIG. 1 but from a different view, illustrating a two-piece construction of the cassette for exemplary purposes;

FIG. 14 is an enlarged perspective view of an insert plate that is part of the fiber terminal block assembly shown in FIG. 11;

FIGS. 17a, 17b and 17c are enlarged views of various portions of the optical retainer shown in FIG. 17;

FIG. 18 is a plan view of the optical retainer shown in FIG. 17;

FIG. 20 is an enlarged plan view of another optical retainer of the optics assembly depicted in FIG. 16;

FIG. 21 is a cross-sectional view taken along a longitudinal axis of the optical retainer shown in FIG. 20;

DETAILED DESCRIPTION OF THE PREFERRED EMBODIMENTS

Figure 1:
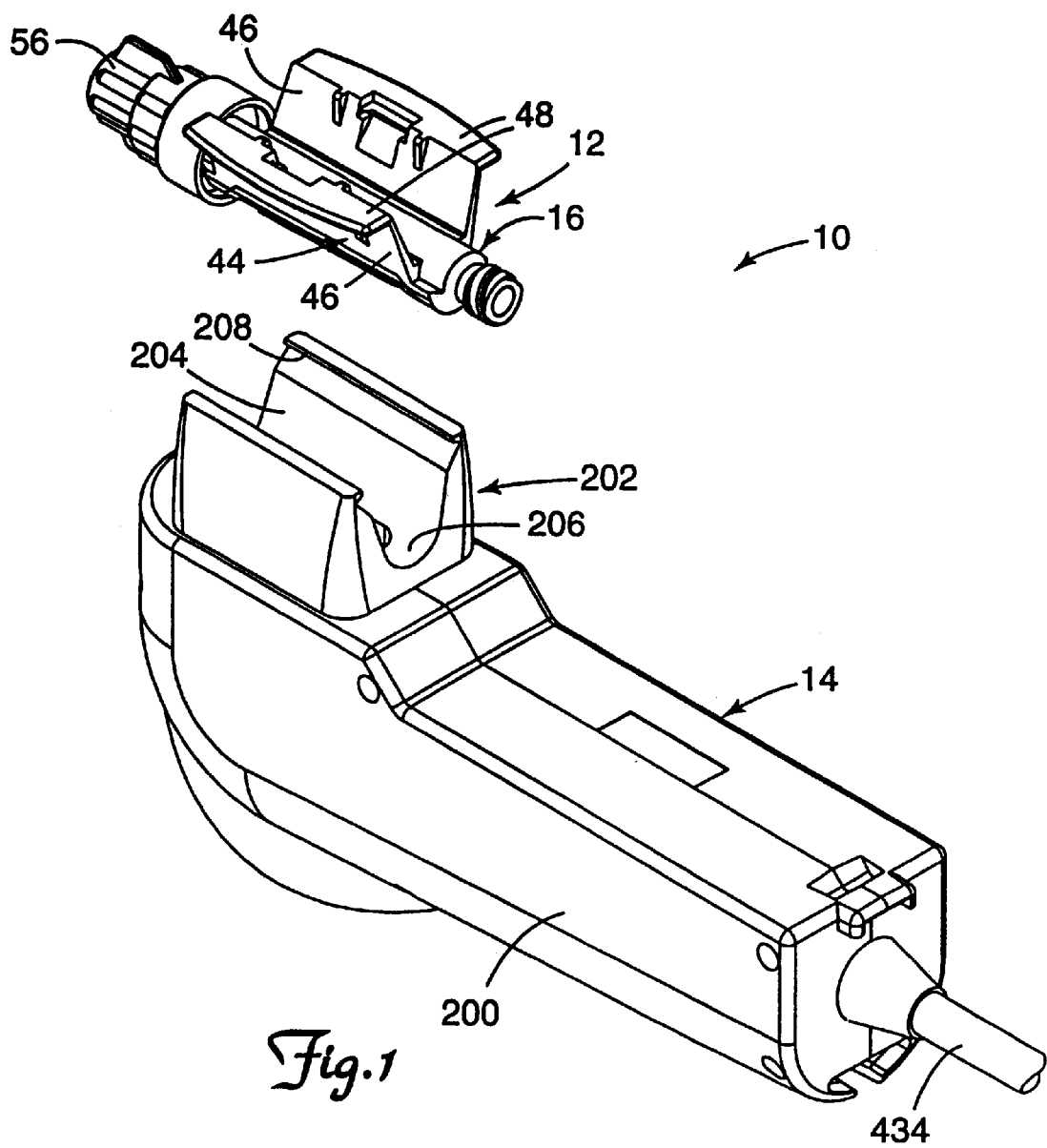
FIG. 1 is a perspective view of a calibration and fluid parameter measurement cassette of the invention along with a fluid parameter measuring device, showing one example of how the cassette and the measuring device are oriented with respect to each other before being coupled together.

A system 10 for measuring one or more characteristics or parameters of fluid such as blood is illustrated in FIG. 1. The system 10 broadly includes a cassette 12 that receives the fluid along with a measuring device 14 for measuring parameters of fluid in the cassette 12.

Figure 3:
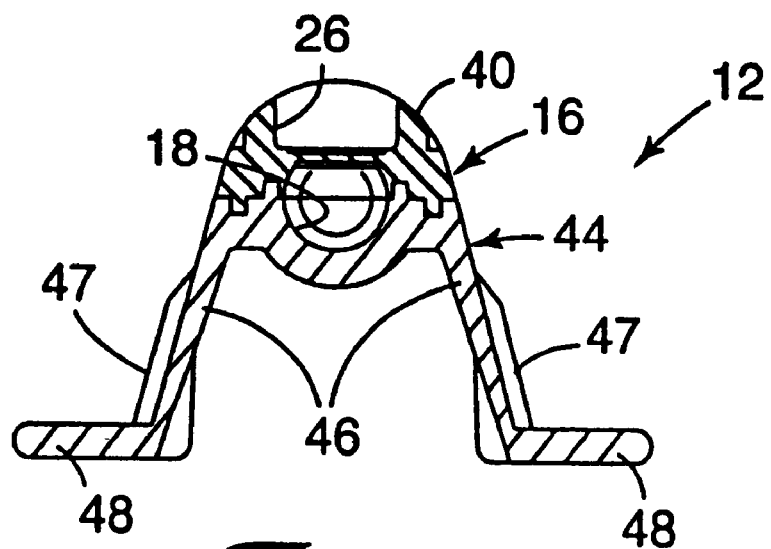
FIG. 3 is a view somewhat similar to FIG. 2 except that FIG. 3 is taken along a different reference plane.
Figure 4:
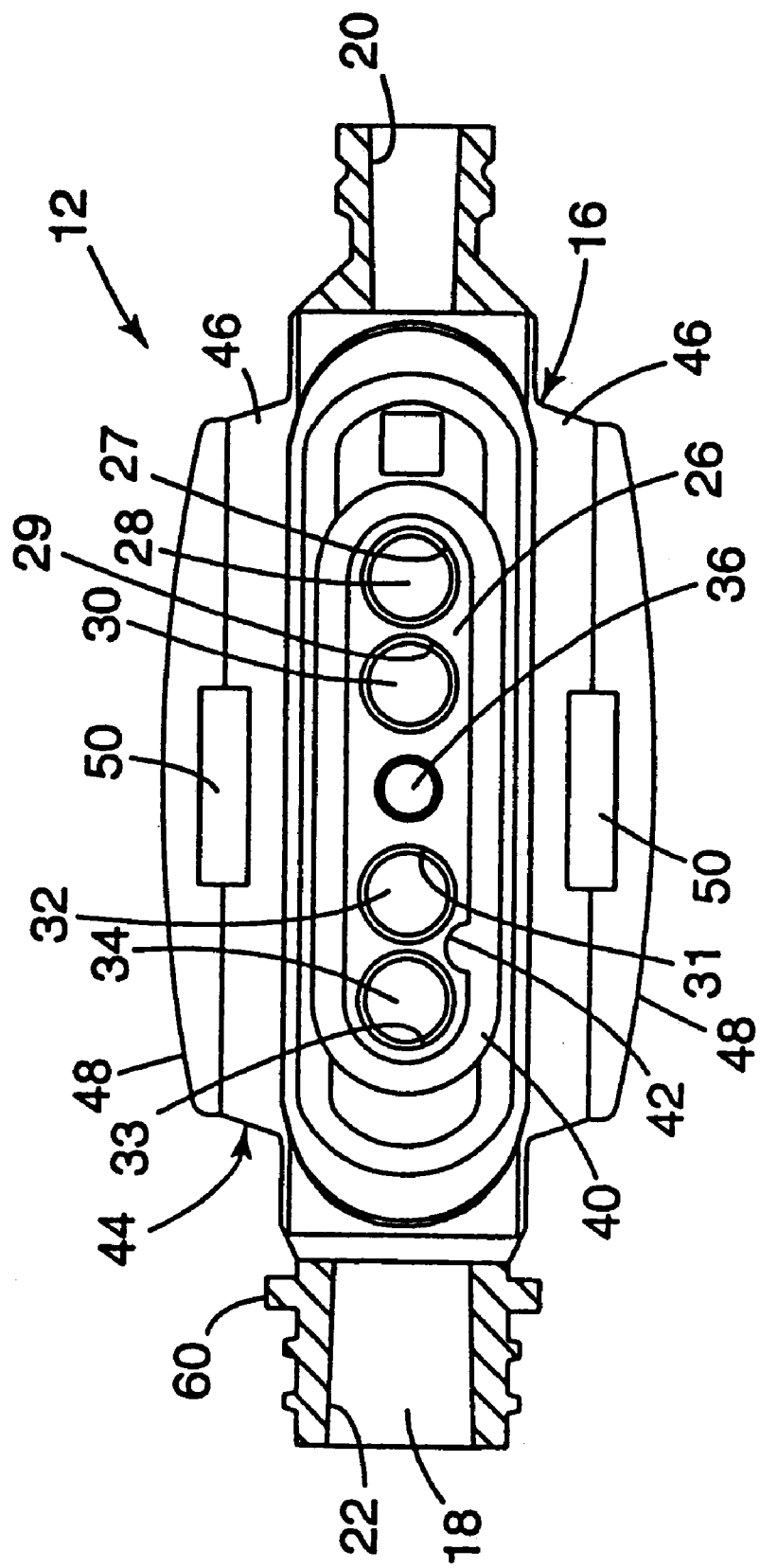
FIG. 4 is an enlarged elevational view in partial section of the cassette shown in FIGS. 2–3, looking toward a side of the cassette that faces the measuring device when the cassette and the measuring device of FIG. 1 are coupled together.
Figure 5:
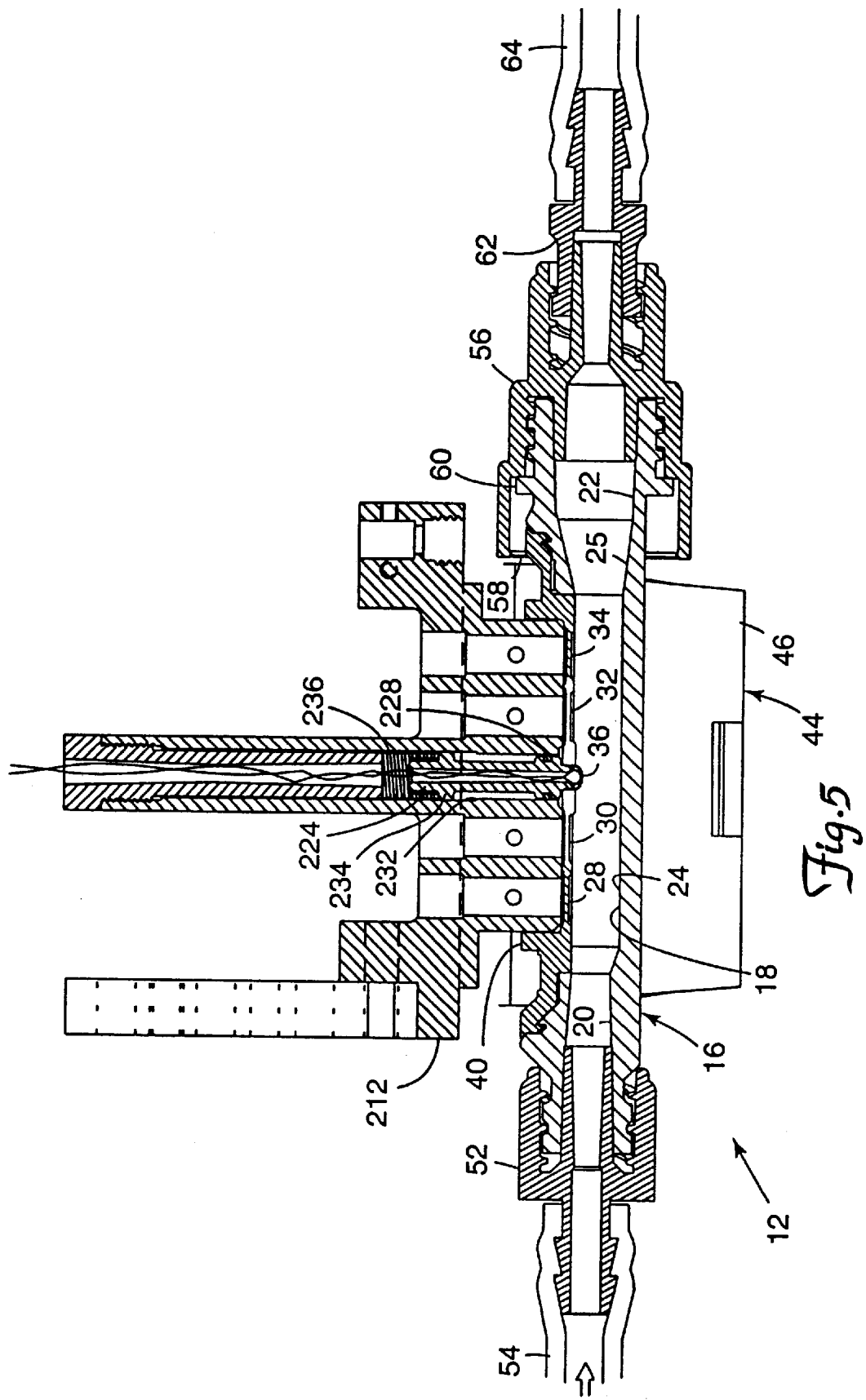
FIG. 5 is an enlarged side cross-sectional view of the cassette and part of the measuring device of FIG. 1 but shown as coupled together, and additionally showing connectors and tubing for coupling the cassette to a fluid circuit such as a cardiopulmonary by-pass circuit.

The cassette 12 is shown in more detail in FIGS. 2–6, and includes an elongated casing 16 having wall sections defining an elongated, internal, flow-through fluid chamber 18 that extends along the longitudinal axis of the casing 16. As illustrated in FIGS. 5 and 6, the fluid chamber 18 includes a first portion 20 having a first or "inlet" port for admitting fluid into the chamber 18, a second portion 22 having a second or "outlet" port for allowing fluid to exit the fluid chamber 18 and a central portion 24 located between the portions 20, 22. (Although the description that follows refers to fluid flowing into the chamber 18 through the first portion 20 and discharged from the chamber 18 through the second portion 22, it should be understood that the fluid may also flow if desired in an opposite direction through the chamber 18 such that the fluid enters the chamber 18 through the second port and exits through the first port).

The fluid chamber 18 also includes a frustoconical expansion region or portion 25 that is located between the central portion 24 and the second portion 22. The expansion portion 25 has free area that is larger than the free area of the middle portion 24 in reference planes perpendicular to the longitudinal axis of the casing 16 and that increases in size as the second portion 22 is approached. The portions 20, 22, 24 and 25 communicate with each other and have circular cross-sections in reference planes perpendicular to the longitudinal axis of the cassette 16. Preferably, at least the wall sections defining the central portion 24 include a hydrophilic surface, and more preferably the wall sections defining all of the portions 20, 22, 24 and 25 include a hydrophilic surface. Optionally, the hydrophilic surface comprises a coating of heparin.

An external side of the casing 16 includes a central section with a generally oval-shaped recess 26. At least one sensor for determining one or more parameters of fluid in the chamber 18 is carried by the casing 16. In the embodiment shown, a series of four sensors are located between the recess 26 and the middle portion 24 of the fluid chamber 18, and the sensors are placed in four cavities that are arranged in aligned, spaced-apart relationship along the longitudinal axis of the casing 16. As depicted in FIG. 4, the sensors include an ion (potassium) sensor 28, a pH sensor 30, and carbon dioxide sensor 32 and an oxygen sensor 34 that are received in cavities 27, 29, 31, 33 respectively.

If desired additional sensors may be employed as described below. Sensors useful in the apparatus of the invention preferably comprise a multi-layer assembly that can be adhesively attached to the cassette casing 16.

The ion sensor 28 preferably comprises the following layers: (i) a backing membrane, (ii) a pressure-sensitive adhesive (PSA) coated on the backing membrane, (iii) a sensing element comprising an ion sensing compound bound to a substrate, the substrate being attached to the membrane (e.g., by a non-interfering adhesive), and (iv) an outermost opacifying overcoat layer on the exposed surface of the substrate.

Useful pressure-sensitive adhesives include silicone adhesives and polyurethane adhesives and others that are capable of bonding a membrane (described below) to the cassette. Preferably, the adhesives are essentially transparent to wavelengths of light used in sensing cassettes of the invention, and are chemically non-interfering with useful ion sensors. Useful silicone adhesives include PSA-518™ (General Electric Co., Schenectady, N.Y.), described in Example 2 of U.S. Pat. No. 5,508,509, which is incorporated herein by reference. Useful polyurethane adhesives include FLEXO-BOND 431™ (Bacon Co., Irvine, Calif.), described in Example 3 of U.S. Pat. No. 5,591,400, which is incorporated herein by reference.

A release liner may be useful when manufacturing the ion sensors to protect the exposed surface of the adhesive layer. These liners can be any that are in common use in industry for the purpose, and are selected according to the adhesive from which they are to release. Examples of useful release liners include poly(ethyleneterephthalate) (PET) that may optionally be coated with, e.g., silicone or a fluoropolymer, for increased ease of release from the adhesive. One useful liner is Scotch Pack 1022™ (3M Company, St. Paul, Minn.), a PET film coated with perfluoro polyether, described in U.S. Pat. No. 5,508.509, Example 2.

The backing membrane provides support (e.g., stiffness and handling capability) for the multilayer assemblies. Preferably, the backing membrane is transparent and essentially impermeable to, or much less permeable than the sensing substrate to, the solution in which a target ion is present, such as blood or a calibrating solution. The membrane preferably allows the signal or signals, preferably the optical signals, from the sensing element and substrate, to pass therethrough. Particularly useful materials of construction for this backing membrane include polymeric materials, such as polyesters, polycarbonates, polysulfones including but not limited to polyethersulfones and polyphenylsulfones, polyvinylidine fluoride, polymethylpentenes, and the like. In a presently preferred embodiment for ion sensor 28, the backing membrane is polycarbonate.

Suitable ion sensors which may be used as the potassium sensor 28 are described in U.S. Pat. No. 5,474,743 (Trend et al.), U.S. Pat. No. 5,176,882 (Gray et al.), U.S. Pat. Nos. 5,136,033, and 5,162,525 (Masilamani et al.); U.S. patent application Ser. No. 08/521,869; and U.S. patent application Docket No. 52630USA7A (filed on even date herewith and assigned to the assignee of the present invention), which are herein incorporated by reference.

Preferred sensors 28 comprise a fluorescent ionophoric compound ("the ionophore") that contains a complexing moiety for binding an ion and a fluorescing moiety. The compound has a wavelength of maximum absorbance of at least about 350 nm. Suitable fluorescing moieties preferably contain close-lying $n\pi^*$ and $\pi\pi^*$ excited states. Suitable fluorescing moieties, when coupled to an appropriate complexing moiety, preferably are capable of ion dependent out-of-plane puckering. Also, the $\pi\pi^*$ state of suitable fluorescing moieties preferably is sufficiently high in energy that ion dependent mixing dominates non-radiative coupling to the ground state. Particularly preferred fluorescing moieties include coumarin moieties, although other aromatic carbonyls or nitroaromatics or N-heterocyclic moieties may be employed. Suitable ion complexing moieties include cyclic "cage" moieties capable of binding an ion. Preferably the cage is capable of selective binding of an ion. Preferred ion complexing moieties include cryptand and crown ether moieties, with cryptand moieties being particularly preferred.

Ions which may be sensed using the ionophore include, for example, $Ag^+$, $Ba^{+2}$, $Ca^{+2}$, $Ce+$, $Cd^{2+}$, $Fr+$, $Hg^{2+}$, $K^+$, $Li^+$, $Mg^{+2}$, $Mn^{2+}$, $Na^+$, $Pb^{+2}$, $Ru+$, $Sr^{+2}$, $Ti^+$, and $Zn^{2+}$. If desired the ionophore may be used in conjunction with an ion selective membrane. Preferred sensors comprise ionophores that sense for $K^+$, $Na^+$, and $Ca^{+2}$.

Suitable fluorescent ionophoric compounds include compounds having the following general formula (Formula "A"):

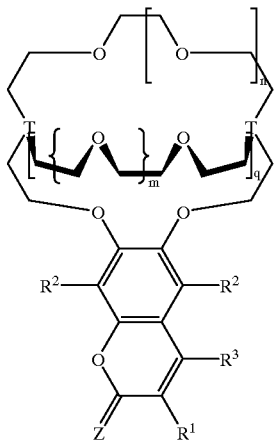

wherein
T is O or N, with the proviso that when T is O q is 0 and n is 0 to 2, and when T is N q is 1 and m and n are independently 0 or 1;
each $R^2$ independently is a sterically non-interferring group, including moieties such as hydrogen, halogen, a hydrocarbyl-containing group, a hetero-acyclic group, or a group having the formula $(CH_2X)_aE$ in which X is O, NH, or a single bond, E is a functional group that includes active hydrogen, and a is a whole number from 1 to 100;

$R^3$ preferably is a non-electron withdrawing group, including non-electron withdrawing moieties such as hydrogen, a hydrocarbyl-containing group, a hetero-acyclic group, a heterocyclic group, or a group having the formula $(CH_2X)_bE$ in which X and E are defined as above and b is a whole number from 0 to 100;

$R^1$ is an electron withdrawing or polarizable group, including moieties such as carboxyl, carboxamide, sulfonylaryl, ester, keto-alkyl ester, heterocyclic moieties and aromatic groups (preferably substituted at one or more positions), most preferred $R^1$ groups include substituted heterocyclic moieties having the general formula (Formula "C"):

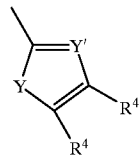

wherein Y and Y' independently are O, S, $NH_x$, or $CH_y$, where x is 0 or 1 and y is 1 or 2, with the proviso that at least one of Y and Y' must be O, S, or $NH_x$, each $R^4$ group is independently hydrogen, halogen, a hydrocarbyl-containing group, a hetero-acyclic group, a heterocyclic group, or a group having the formula $(CH_2X)_cE$ in which X and E are defined as above and c is a whole number from 0 to 100, or both $R^4$ groups together with the carbon atoms to which they are attached form a 5- or 6-membered ring which optionally can have one or more further $R^4$ groups attached; and Z is O or $NR^5$, where $R^5$ is hydrogen or a hydrocarbyl-containing group, more preferably $R^5$ is H or a C1 to C4 alkyl group, and most preferably $R^5$ is H.

In general, compounds of Formula A have a wavelength of excitation of at least about 350 nm and a wavelength of emission preferably of no more than about 500 nm. Preferred compounds, (e.g., wherein $R^1$ is a heterocyclic moiety having the general formula of Formula "C") have a wavelength of excitation of at least about 380 nm and a wavelength of emission of no more than about 500 nm. In a particularly preferred embodiment, substituent groups and their position on the coumarin ring have been chosen so as to ensure that the excitation (i.e., absorption) maximum of the ionophore of the present invention is centered at a wavelength greater than 380 nm. This allows the ionophore of the present invention to be used with solid state light sources such as, for example, blue LEDs and lasers. The wavelengths of excitation and emission of these compounds are preferably at least about 10 nm apart, which allow these compounds to be useful in fluoresence-based cation concentration measurement techniques. Substituent groups and their positions are also preferably chosen to keep the emission wavelength below 500 nm, thereby preserving ionophore response for this class of indicators. Finally, substituent groups and their positions are preferably chosen to provide the option for colvalent attachment to substrates. Preferably, the substrate to which the indicator is attached is chosen to support uniform and reproducible ionophore response and to minimize the effect of physiological pH changes on ionophore response. Suitable coupling agents for covalent attachment are described in U.S. Pat. No. 5,053, 520, which is herein incorporated by reference. Homobifunctional and/or heterobifunctional coupling agents are described in World Pat. No. WO 96/07268 and WO 96/10747, which are herein incorporated by reference.

Preferably, the ionophore is covalently bonded to a suitable substrate that can be attached to the backing membrane, as described below. The substrate preferably is a polymeric material that is water-swellable and permeable to the ionic species of interest, and is preferably insoluble in the medium to be monitored. Particularly useful substrate polymers include, for example, ion-permeable cellulosic materials, high molecular weight or crosslinked polyvinyl alcohol (PVA), dextran, crosslinked dextran, polyurethanes, quaternized polystyrenes, sulfonated polystryrenes, polyacrylamides, polyhydroxyalkyl acrylates, polyvinyl pyrrolidones, hydrophilic polyamides, polyesters and mixtures thereof. In a particularly useful embodiment, the substrate is cellulosic, especially ion-permeable crosslinked cellulose. In a presently preferred embodiment, the substrate comprises a regenerated cellulose membrane (CUPROPHAN™, Enka AG, Ohderstrasse, Germany) that is crosslinked with an epoxide, such as butanediol diglycidyl ether, further reacted with a diamine to provide amine functionality pendant from the cellulosic polymer, as described in U.S. Pat. No. 5,591,400, Example 4, incorporated herein by reference.

The above-described ionophore is preferably covalently bonded to the amine-functional cellulose substrate by any useful reactive technique, which may depend upon the chemical functionality of the ionophore.

The ionophore-functionalized cellulose substrate optionally can be adhesively bonded to the above-described backing membrane by any non-interfering adhesive. Preferably, the adhesive is essentially transparent to light used in excitation of the ionophore and to light emitted therefrom. One such useful adhesive is FLEXOBOND 431™ urethane adhesive (Bacon Co., Irvine, Calif.).

Alternatively, the functionalized substrate can be thermally fused to the membrane, providing the conditions necessary for thermal bonding are not detrimental to functioning of the ionophore, sensor and backing membrane.

The outermost layer of the multilayer sensing assembly, that is, the layer in immediate contact with the fluid to be monitored, preferably comprises an opacifying layer that optically isolates the ionophore in the sensing assembly. The opacifying agent can be applied before the ionophore-substrate component is applied to the backing membrane, as described in U.S. Pat. Nos. 5,081,041 and 5,081,042, incorporated herein by reference, or after the sensing component is attached to the substrate. It can be directly attached to the sensing element or it can be separate from the sensing element. In preferred embodiments, it is applied after the sensing component is attached to the backing membrane.

The overcoat preferably is a material that is permeable to the analyte of interest, such as a polymeric material as described above, containing an opaque agent such as carbon black, or carbon-based opaque agents, ferric oxide, metallic phthalocyanines, and the like. Such opaque agents are preferably substantially uniformly dispersed in the polymer in an amount effective to provide the desired degree of opacity to provide the desired optical isolation. A particularly useful opaque agent is carbon black. The overcoat can also be an ink coating on the sensing element applied using a variety of techniques, such as an inkjet technique or an ink-screening technique. The overcoat can also be a black membrane stapled or heat-staked to the cassette holding the sensing element. For example, it can be a black DURAPORE™ membrane (available from Millipore as a white membrane which is then treated with black ink) and heat sealed to the cassette, as described in U.S. Pat. Nos. 5,508,509 and 5,591,400, incorporated herein by reference. A presently preferred embodiment comprises carbon black dispersed in a matrix of epoxy-crosslinked dextran, as described in U.S. Pat. No. 4,919,891, incorporated herein by reference.

A presently preferred embodiment of sensor 28 comprises a sensing layer that includes 6,7-[2.2.2]-cryptando-3-[2"-(5"-carboxy)furyl]coumarin covalently bonded to a crosslinked amine functional cellulose membrane (CUPROPHAN™, Enka AG, Ohderstrasse, Germany), the sensing layer being adhered to a polycarbonate backing membrane by FLEXOBOND 430™ urethane adhesive and the backing membrane having coated thereon CW14™ pressure-sensitive adhesive on a release liner.

Suitable pH sensors 30 are described in U.S. Reissue Pat. No. Re 31,879 (Lubbers), U.S. Pat. No. 4,798,738 (Yafuso), U.S. Pat. No. 4,824,789 (Yafuso), U.S. Pat. No. 4,886,338 (Yafuso), U.S. Pat. No. 4,999,306, (Yafuso), U.S. Pat. No. 5,081,041 (Yafuso), U.S. Pat. No. 5,081,042 (Yafuso), U.S. Pat. No. 5,127,077 (Iyer), U.S. Pat. No. 5,132,057 (Tomisaka), U.S. Pat. No. 5,403,746 (Bentsen), U.S. Pat. No. 5,508,509 (Yafuso), and U.S. Pat. No. 5,591,400 (Dektar et al.), the teachings of which are incorporated herein by reference.

The pH sensor 30 preferably comprises the following layers: (i) a backing membrane, (ii) a pressure-sensitive adhesive (PSA) coated on the backing membrane, (iii) a sensing element comprising a pH sensing component bound to a substrate, the substrate being attached to the membrane (e.g., by a non-interfering adhesive), and (iv) an outermost opacifying overcoat layer on the exposed surface of the substrate. With the exception of the pH sensor, these layers and the multilayer construction are essentially as described above for the potassium-ion sensor 28.

Suitable pH sensing components include many well known pH indicators and/or functionalized derivatives of such indicators. Among the useful pH sensing components are hydroxypyrenetrisulfonic acid ("HPTS") and derivatives, e.\g., salts, thereof, phenolphthalein, fluorescein, phenol red, cresol red, pararosaniline, magenta red, xylenol blue, bromocresol purple, bromphenol blue, bromothymol blue, metacresol purple, thymol blue, bromophenol blue, bromothymol blue, tetrabromophenol blue, bromchlorphenol blue, bromocresol green, chlorpheno red, o-cresolphthalein, thymolphthalein, metanil yellow diphenylamine, N,N-dimethylaniline, indigo blue, alizarin, alizarin yellow GG, alizarin yellow R, congo red, methyl red, methyl violet 6B, 2,5-dinitrophenol, and/or the various functionalized derivatives of the above species. Sensing components for other ionic species can be made from organic species which include fluorescein, diiodofluorescein, dichlorofluorescin, phenosafranin, rose bengal, cosin I bluish, cosin yellowish, magneson, tartrazine, eriochrome black T, coumarin, alizarin, and others. The preferred pH sensing component is hydroxypyrenetrisulfonic acid (HPTS), derivatives of hydroxypyrenetrisulfonic acid, and mixtures thereof.

Additional suitable indicator components for use in the present invention include: 9-amino-6-chloro-2-methoxyacridine; 2',7'-bis-(2-carboxyethyl)-5-(and-6)-carboxyfluorescein; 2',7'-bis-(2-carboxyethyl)-5-(and-6)-carboxyfluorescein, acetoxymethyl ester; 2',7'-bis-(2-carboxyethyl)-5-(and-6)-carboxyfluorescein, acetoxymethyl ester; 5-(and-6)-carboxy-2',7'-dichlorofluorescein; 5-(and-6)-carboxy-2',7'-dichlorofluorescein diacetate; 5-(and-6)-carboxy-4',5'-dimethylfluorescein; 5-(and-6)-carboxy-4',5'-dimethylfluorescein diacetate; 5-carboxyfluorescein; 6-carboxyfluorescein; 5-(and-6)-carboxyfluorescein; 5-carboxyfluorescein diacetate; 6-carboxyfluorescein diacetate; 5-carboxyfluorescein diacetate, acetoxymethyl ester; 5-(and-6)-carboxyfluorescein diacetate; 5-(and-6)-carboxynaphthofluorescein; 5-(and-6)-carboxynaphthofluorescein diacetate; 5-(and-6)-carboxySNAFL®-1, succinimidyl ester {5'(and 6')-succinimidyl ester-3,10-dihydroxy-spiro[7H-benzo[c]xanthene-7,1'(3'H)-isobenzofuran]-3'-one}; 5-(and-6)-carboxySNAFL®-2, succinimidyl ester {5'(and 6')-succinimidyl ester-9-chloro-3,10-dihydroxy-spiro[7H-benzo[c]xanthene-7,1'(3'H)-isobenzofuran]-3'-one}; carboxySNAFL®-1{5'(and 6')-carboxy-3,10-dihydroxy-spiro[7H-benzo[c]xanthene-7,1'(3'H)-isobenzofuran]-3'-one}; carboxySNAFL®-1 diacetate {5'(and 6')-carboxy-3,10-diacetoxy-spiro[7H-benzo[c]xanthene-7,1'(3'H)-isobenzofuran]-3'-one}; carboxySNAFL®-2{5'(and 6')-carboxy-9-chloro-3,10-dihydroxy-spiro[7H-benzo[c]xanthene-7,1'(3'H)-isobenzofuran]-3'-one}; carboxySNAFL®-2 diacetate {5'(and 6')-carboxy-9-chloro-3,10-diacetoxy-spiro[7H-benzo[c]xanthene-7,1'(3'H)-isobenzofuran]-3'-one}; carboxySNARF® -1 {5'(and 6')-carboxy-10-dimethylamino-3-hydroxy-spiro[7H-benzo[c]xanthene-7,1'(3'H)-isobenzofuran]-3'-one}; carboxySNARF®-1, AM acetate {3-acetoxy-5'-acetoxymethoxycarbonyl-10-dimethylamino-spiro[7H-benzo[c]xanthene-7,1'(3'H)-isobenzofuran]-3'-one}; carboxySNARF®-2 {5'(and 6')-carboxy-10-diethylamino-3-hydroxy-spiro[7H-benzo[c]xanthene-7,1'(3'H)-isobenzofuran]-3'-one}; carboxySNARF®-2, AM acetate {3-acetoxy-5'-acetoxymethoxycarbonyl-10-diethylamine-3-hydroxy-spiro[7H-benzo[c]xanthene-7,1'(3'H)-isobenzofuran]-3'-one}; carboxySNARF®-6 {5'(and 6')-carboxy-10-diethylamino-3-hydroxy-spiro[7H-benzo[c]xanthene-7,1'(3'H)-isobenzofuran]-3'-one}; carboxySNARF®-X {5'(and 6')-carboxy-3-hydroxy-tetrahydroquinolizino[1,9-hi]spiro[7H-benzo[c]xanthene-7,1'(3'H)-isobenzofuran]-3'-one}; 5-chloromethylfluorescein diacetate; 4-chloromethyl-7-hydroxycoumarin; Cl-NERF {4-[2-chloro-6-(ethylamino)-7-methyl-3-oxo-3H-xanthen-9-yl]-1,3-benzene-dicarboxylic acid}; dextran, BCECF, 10,000 MW, anionic {dextran, 2',7'-bis(2-carboxyethyl)-5 (and 6)-carboxy-fluorescein, anionic}; dextran, BCECF, 40,000 MW, anionic; dextran, BCECF, 70,000 MW, anionic; dextran, Cl-NERF, 10,000 MW, anionic; dextran, Cl-NERF, 70,000 MW, anionic; dextran, Cl-NERF, 10,000 MW, anionic, lysine fixable; dextran, DM-NERF, 10,000 MW, anionic {dextran, 4-[2,7-dimethyl-6-(ethylamino)-3-oxo-3H-xanthen-9-yl]-1,3-benzene dicarboxylic acid, anionic}; dextran, DM-NERF, 70,000 MW, anionic; dextran, DM-NERF, 10,000 MW, anionic, lysine fixable; dextran, 7-hydroxycoumarin, 10,000 MW, neutral; dextran, 7-hydroxycoumarin, 70,000 MW, neutral; dextran, b-methylumbelliferone, 10,000 MW, neutral; dextran, b-methylumbelliferone, 70,000 MW, neutral; dextran, SNAFL®-2, 10,000 MW, anionic {dextran, 9-chloro-3,10-dihydroxy-spiro[7H-benzo[c]xanthene-7,1'(3'H)-isobenzofuran]3'-one, anionic}; dextran, SNAFL®-2, 70,000 MW, anionic {dextran, 10-dimethylamino-3-hydroxy-spiro[7H-benzo[c]xanthene-7,1'(3'H)-isobenzofuran] -3'-one, anionic}; dextran, SNARF®-1, 10,000 MW, anionic; dextran, SNARF®-1, 70,000 MW, anionic; 1,4-dihydroxyphthalonitrile; DM-NERF {4-[2,7-dimethyl-6-ethylamino)-3-oxo-3H-xanthen-9-yl]1,3-benzene dicarboxylic acid}; fluorescein diacetate; 8-hydroxypyrene-1,3,6-trisulfonic acid, trisodium salt; naphthofluorescein; naphthofluorescein diacetate; SNAFL®-1 {3,10-dihydroxy-spiro[7H-benzo[c]xanthene-7,1'(3'H)-isobenzofuran]-3'-one}; and SNAFL®-1, diacetate {3,10-diacetoxy-spiro[7H-benzo[c]xanthene-7,1'(3'H)-isobenzofuran]-3'-one}.

In a presently preferred embodiment, HPTS indicator is covalently bonded to an amine-functional CUPROPHANrM substrate that is bonded by FLEXOBOND 431™ polyurethane adhesive to a polycarbonate backing membrane. The sensing substrate is overcoated with an epoxy-crosslinked dextran matrix having carbon black dispersed therein.

Suitable carbon dioxide sensors 32 are described in U.S. Reissue Pat. No. Re 31,879 (Lubbers), U.S. Pat. No. 4,557,900 (Heitzmann), U.S. Pat. No. 4,824,789 (Yafuso), U.S. Pat. No. 4,849,172 (Yafuso), U.S. Pat. No. 4,867,919 (Yafuso), U.S. Pat. No. 4,919,891 (Yafuso), U.S. Pat. No. 5,127,077 (Iyer), U.S. Pat. No. 5,175,016 (Yafuso), U.S. Pat. No. 5,272,088 (Morlotti), U.S. Pat. No. 5,403,746 (Bentsen), U.S. Pat. No. 5,453,248 (Olstein), and U.S. Pat. No. 5,508,509 (Yafuso), incorporated herein by reference.

The carbon dioxide sensor 32 may also be in the form of a multilayer assembly. In one presently preferred embodiment, the sensing substrate layer of sensor 32 comprises a hydrophobic matrix in which is dispersed a plurality of hydrophilic particles or beads carying a carbon dioxide sensing indicator. The indicator can be attached to or in the beads in any effective manner.

Because the beads are hydrophilic, they are adapted to receive and contain an aqueous solution of the indicator. "Hydrophilic" means a material, such as a polymeric substance, that retains a large fraction (e.g, greater than 20% of its weight) of water within its structure but does not dissolve in water. Hydrophilic materials useful as beads in carbon dioxide sensors include glass beads or hydrogels, polyacrylamide, cross-linked dextran, agarose, poly (hydroxyalkyl methacrylate), sulfonated polystyrene, and the like. A presently preferred hydrophilic bead material is SEPHADEX 75G™ cross-linked dextran (Pharmacia Biotech, Inc., Piscataway, N.J.).

In sensing carbon dioxide concentrations, examples of absorbance indicators that can be used include chlorophenyl red, bromo cresol purple, nitrophenol, bromo thymol blue, penachlorome, phenol red and the like. Useful fluorescence indicators for carbon dioxide include the sensors listed above that are useful for pH sensing, beta-methylumbelliferone, fluorescein and the like. A particularly useful carbon dioxide sensor is hydroxypyrene 3,6,8-trisulfonic acid, herein referred to as HPTS or hydroxypyrene trisulfonic acid and derivatives, e.g., salts of HPTS. The more preferred sensing component, particularly for sensing the concentration of carbon dioxide in blood, is selected from HPTS, derivatives of HPTS and mixtures thereof. The alkali and alkaline earth metal salts of HPTS are useful HPTS derivatives.

The hydrophobic matrix material in which the beads bearing a suitable indicator are dispersed is preferably transparent to excitation and emission wavelengths of light useful in sensing cassettes of the invention, and is otherwise inert to carbon dioxide, the absorbance or fluorescence indicator, and the beads. The hydrophobic matrix serves to isolate the indicator, while allowing carbon dioxide to diffuse therethrough. Suitable hydrophobic matrix materials include numerous silicones, such as silicone elastomer, room temperature vulcanizable (RTV) silicone rubber, heat vulcanizable silicone rubber, polydimethylsiloxane, poly (vinyl siloxane), silicone-polycarbonate copolymer, and the like, as well as perfluorinated (polyether) urethanes. Particularly preferred silicone matrix materials include PS 443™ vinyl-terminated dimethylsiloxane and PE1055™ polydimethylsiloxane, both commercially available from Petrarch Systems, Inc.

In a presently preferred embodiment, the carbon dioxide sensor 32 comprises a sensing layer including HPITS sensing dye on SEPHADEX 75G™ crosslinked dextran beads in a silicone matrix adhered to a polycarbonate backing membrane and overcoated with a opacifying layer comprising iron oxide pigment dispersed in a silicone matrix.

In an alternative embodiment, a solution of a suitable indicator dye can be formed in an aqueous buffer, and the solution can be emulsified with a liquid precursor of the hydrophobic polymeric matrix. Upon polymerization of the precursor, the emulsified indicator is essentially uniformly dispersed throughout the polymer matrix. Indicator dyes and silicone polymers described above can be useful in the embodiment.

Suitable oxygen sensors 34 are described in U.S. Pat. No. 4,557,900 (Heitzmann), U.S. Pat. No. 4,849,172 (Yafuso), U.S. Pat. No. 4,867,919 (Yafuso), U.S. Pat. No. 4,919,891 (yafuso), U.S. Pat. No. 5,043,285 (Surgi), U.S. Pat. No. 5,127,077 (Iyer), U.S. Pat. No. 5,296,381 (Yafuso), U.S. Pat. No. 5,409,666 (Nagel et al.), U.S. Pat. No. 5,453,248 (Olstein), U.S. Pat. No. 5,462,879 (Bentsen), U.S. Pat. No. 5,462,880 (Kane), U.S. Pat. No. 5,480,723 (Klainer), U.S. Pat. No. 5,498,549 (Nagel et al.), and U.S. Pat. No. 5,508,509 (Yafuso), incorporated herein by reference, and European Patent application EP 585,212.

The oxygen sensor 34 may be in the form of a multilayer sensing assembly. In particular, the construction of the oxygen sensor 34 may closely resemble that of the carbon dioxide sensor 32, in that the sensing layer comprises a sensing dye or indicator in a gas-permeable (e.g. silicone) matrix, and the overcoat layer may comprise a pigment in a silicone matrix. The gas-permeable matrix materials useful in the oxygen sensor 34 preferably can be the same as those previously described.

Useful oxygen sensing indicators comprise fluorescence indicators including one or more polynuclear aromatic compounds, derivatives of polynuclear aromatic compounds and the like. Examples of such polynuclear aromatic compounds include decacyclene, benzo-ghi-perylene and coronene. Oxygen indicators may include a mixture of tertiary butyl derivatives of such polynuclear aromatic compounds. Such indicators are more fully described in Yafuso, et al U.S. Pat. No. 4,849,172 which is incorporated in its entirety herein by reference.

Additional useful oxygen indicators include complexes of ruthenium(II), osmium(II), iridium(III), rhodium, rhenium, and chromium(III) with 2,2'bipyridine, 1,10-phenanthroline, 4,7-diphenyl-1,10-phenanthroline, 4,7-dimethyl-1,10-phenanthroline, 4,7-disulfonated-diphenyl-1,10-phenanthroline, 2,2'bi-2-thiazoline, 2,2'bithiazole, 5-bromo-1,10-phenanthroline, and 5-chloro-1,10-phenthroline, and complexes of Co(II), Cu(II), Pt(II), Pd(II) and Zn(II) with porphyrin, etioporphyrin, tetraphenylporphorin, tetrafluorophenylporphirin, tetrabenzporphirin, tetrafluorobenzporphirin, tetrachlorobenzporphirin, mesoporphirin IX diester, protoporphirin IX dimethyl ester, and octaethylporphorin. Ruthenium complexes are preferred, among the metal complexes.

The oxygen indicators may be covalently bonded to the polymeric materials or matrix materials included in the sensing composition. Such covalent bonding is preferably accomplished by providing an oxygen indicator component including a reactable group which reacts with a reactable group, preferably a different reactable group, present in one of the components of the precursor of the polymeric matrix material. Thus, during the formation of the polymeric matrix material, the above-noted reactable groups also react to covalently bond the oxygen indicator to the matrix material. Particularly useful oxygen indicator components include the above-noted polynuclear aromatic compounds derivatized to include a reactable group, such as a reactable group with functional carbon-carbon unsaturation. Vinyl derivatives of such compounds are particularly preferred.

Alternatively, the oxygen sensor can comprise a sensing element, an excitation means, and a detecting means, wherein the sensing means includes one or more, preferably one or two, monomeric indicator components, preferably located in, more preferably covalently bonded to, a matrix material, preferably a solid matrix material. Each of these monomeric indicator components is capable of providing a first emitted signal of a given wavelength in response to exposure to a first excitation signal. Further, this sensing element is capable of providing a second emitted signal (due to emission by the excited state complex), preferably having a longer wavelength than the first emitted signal or signals, in response to a second excitation signal.

In a particularly useful embodiment, the indicator component is sensitive to the concentration of oxygen in a fluid and comprises one or more polynuclear aromatic compounds and/or one or more derivatives thereof. The polynuclear aromatic compound is preferably any fluorescent or absorbent, more preferably fluorescent, optical indicator of the polynuclear aromatic class. The polynuclear aromatic compound from which the indicator component is derived is still more preferably selected from the group consisting of perylene, decacyclene, benzoperylene (e.g., benzolghilperylene), coronene, pyrene, porphycine, porphyrin, chlorin, phthalocyanine and derivatives and mixtures thereof. Since perylene and derivatives of perylene have a relatively reduced sensitivity to oxygen, other polynuclear aromatic compounds, such as those noted herein, are preferably employed when the analyte is oxygen. When an excimer component is to be utilized, the monomeric indicator component is preferably selected from one polynuclear aromatic compound, derivatives of the same one polynuclear aromatic compound and mixtures thereof. Excellent results are achieved if the polynuclear aromatic compound is benzo[ghi]perylene.

If desired, the basic polynuclear aromatic compound may be derivatized with one or more other groups, e.g., non-functional substituent groups such as alkyl groups, provided such derivatization does not substantially interfere with excited state complex provided emitted signal generation. Such derivatives are discussed in Nagel et al. U.S. Pat. No. 5,409,666 which is incorporated by reference. For example, the monomeric indicator component of a sensing element derived by covalently bonding vinyl benzo[ghi]perylene in an addition cure silicone polymer is said to be a derivative of benzo[ghi]perylene.

Monomeric components useful in sensor 34 may include, for example, two or more similar monomeric indicator components, two or more different monomeric indicator components, or one or more, preferably one, monomeric indicator components and one or more, preferably one, monomeric non-indicator components. Preferably, such monomeric components have no substantial detrimental effect on the sensing element, on the sensor system, on the analyte or on the medium to which the sensing element is exposed.

Examples of monomeric components which produce more preferred oxygen-sensing components include: (1) polynuclear aromatic monomeric components; (2) aliphatic or aromatic amine-containing or aromatic ether-containing monomeric components; and (3) aromatic nitrile monomeric components. More preferred exciplex components comprise at least one monomeric component selected from group (1) and at least one monomeric component selected from group (2). Alternatively, another more preferred component comprises at least one monomeric component selected from group (3) and at least one monomeric component selected from either group (1) or (2).

Examples of useful aromatic monomeric components (group 1) include biphenyl, naphthalene, phenanthrene, p-terphenyl, chrysene, benzpyrene, pyrene, dibenzanthrene, benzanthrene, anthracene, perylene, benzperylene, fluoranthene, coronene, quinoline, phenylquinoline, benzquinoline, quinoxaline, dibenzquinoxaline, benzquinoxaline, phthalimide, pyridine, phenazine, dibenzphenzine, acridine, benzacridine and derivatives of these compounds. Examples of useful aliphatic or amine-containing or aromatic ether-containing monomeric components (group 2) include tetramethyl-p-phenylenediamine, dimethoxydimethylaniline, methoxydimethylaniline, diethylaniline, diphenylmethylamine, triethylamine, indole, dimethyltoluidine, tri-p-anisylamine, ditolylmethylamine, tritolylamine, triphenylamine, ethylcarbazole, trimethoxybenzene, tetramethoxybenzene and derivatives of these compounds. Examples of aromatic nitrile acceptor monomeric components (group 3) include benzonitrile, cyanonaphthalene, dicyanobenzene and derivatives of these compounds.

Any of these monomeric component pairs can be tethered and/or covalently bonded to a matrix material, e.g., silicone.

In a presently preferred embodiment, the oxygen sensor 34 comprises a sensing layer including vinyl benzo[ghi] perylene covalently bonded to a silicone matrix comprising crosslinked polyalkyl(aryl)hydrosiloxane, adhered to a polycarbonate backing membrane and overcoated with a silicone matrix of dispersed carbon black.

In a particularly presently preferred embodiment, the sensor 28 is provided as a multilayered laminate attached to the cassette 12 in the cavity 27. The ion sensor 28 and the pH sensor 30 are preferably placed near the first "inlet" portion 20 of the fluid chamber 18 so that they will be positioned at the bottom half of the cassette during calibration. This assures that the sensors 28 and 30 will be exposed to liquid during calibration. The sensors 32 and 34 are less sensitive to the need for immersion in liquid during calibration.

Alternatively, the cassette 12 can include sensors for potassium, sodium, calcium and glucose, wherein these sensors use essentially the same chemistry as described above. For example, potassium, sodium, and calcium ion detection can use suitable ionophoric coumarocryptands according to Formula A, wherein the size of the cryptand cage is specific for each ion. A suitable glucose sensor can comprise any one of the oxygen sensors described above, modified by the presence of the enzyme glucose oxidase. Glucose detection can be based upon depletion of oxygen during enzymatic oxidation of glucose, as described, e.g., in U.S. Pat. No. 5,518,694, incorporated herein by reference. With minor modifications to the optical train described below, the measuring device 14 can be adapted to accommodate these alternate sensors. In some applications, e.g., cardiovascular blood parameter monitoring, it may be advantageous to use both types of measuring devices.

Other sensors that can be useful in the cassette 12 may include, e.g., a fluorescence-based temperature sensor, such as can be prepared by immobilizing a ruthenium based indicator such as ruthenium(II)(diphenylphenanthroline)$_3$ (dimethylsilylpropanesulfonate)$_2$ in an oxygen-impermeable matrix, e.g., poly(methylmethacrylate).

A hole in the casing 16 is located between the pH sensor 30 and the carbon dioxide sensor 32. A thermistor-receiving well 36 is fixed to the casing 16 and extends over the hole. The well 36 has a hat-shaped configuration with a brim that is bonded by an adhesive to wall sections of the casing 16 that face the central portion 24 of the fluid chamber 18. A suitable adhesive is an acrylic urethane adhesive such as "UV Cure" brand adhesive from Loctite Corporation. The well 36 is preferably made of a corrosion-resistant material having a thermal conductivity similar to metal, such as 0.004 inch (0.1 mm) thick titanium. As illustrated for example in FIGS. 5 and 6, the well 36 protrudes into the central portion 24 of the fluid chamber 18 to provide intimate thermal contact with fluid therein.

The casing 16 also includes a generally oval-shaped rim 40 that circumscribes the recess 26 and extends outwardly in a direction away from the longitudinal axis of the casing 16. As can be appreciated by reference to FIG. 4, the major axes of the oval-shaped recess 26 and the surrounding rim 40 coincide and extend across the center of the sensors 28, 30, 32, 34 and the well 36 and are also parallel with the longitudinal axes of the casing 16 and the fluid chamber 18.

A semi-cylindrical alignment key 42 is integrally connected to an inner wall of the rim 40. Preferably, the alignment key 42 is oriented such that a reference plane that is perpendicular to the longitudinal axis of the casing 16 and extends equidistant between the sensor 32 and the sensor 34 also bisects the key 42 along its central diametrical plane.

Figure 2:
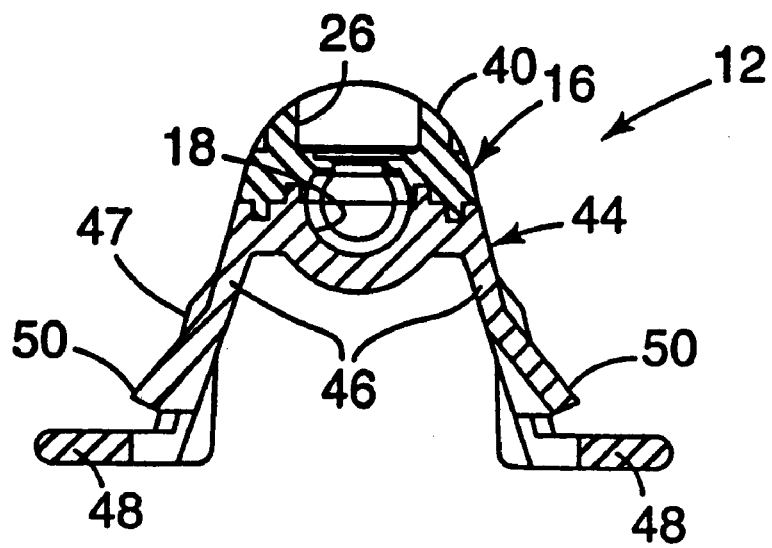
FIG. 2 is an enlarged, longitudinally transverse cross-sectional view through the cassette alone that is shown in FIG. 1.

The cassette 12 further includes a first, male coupling 44 for detachably connecting the casing 16 to the measuring device 14. The coupling 44 has a convex, generally U-shaped configuration in directions perpendicular to the longitudinal axis of the casing 16 as depicted in FIGS. 2 and 3. The coupling 44 includes the aforementioned central section of the casing 16 and opposed leg portions 46 that extend outwardly from the casing 16 in a direction away from the direction of outward extension of the rim 40. Each leg portion 46 includes a pair of support sections having flat, coplanar outer surfaces 47 (see, e.g., FIGS. 2, 3 and 7; omitted in FIG. 4) that are parallel to the outer side of the respective leg portion 46. Preferably, the outer surfaces 47 of the opposed leg portions 46 converge as the casing 16 is approached and extend along respective reference planes that are oriented at an angle in the range of about 28 degrees to about 32 degrees relative to each other. More preferably, the outer surfaces 47 extend along respective reference planes that are oriented at an angle of about 30 degrees relative to each other.

A flange 48 is integrally connected to the outer end of each leg portion 46. The flanges 48 lie in a common reference plane that is parallel to the longitudinal axis of the casing 16. The leg portions 46 are somewhat flexible and can be moved slightly toward each other under the influence of finger pressure, but also have sufficient memory to quickly and repeatedly return to their original, normal orientation as shown in the drawings once finger pressure is released.

An outer, central end region of each leg portion 46 is integrally connected to a wedge-shaped tab 50 that lies between the support sections. The tabs 50 extend away from each other and outwardly from the respective leg portions 46 along respective reference planes that are oriented at an angle of about 80 degrees relative to each other. Additionally, a distal edge of each tab 50 extends in a reference plane that is oriented at an angle of 25 degrees relative to the direction of extension of the flanges 48. Outermost edges of the tabs 50 are spaced outwardly relative to adjacent regions of respective leg portions 46 and lie in a common reference plane that is between the longitudinal axis of the casing 16 and the aforementioned reference plane containing the flanges 48.

Preferably, the casing 16 is made of a relatively clear plastic material such as medical grade polycarbonate, and is constructed of two or more initially separate pieces that are injection-molded and then joined together. An example of a suitable two-piece construction is shown in FIG. 7. In FIG. 7, one piece of the casing 16 includes the recess 26 and the rim 40, and carries the four sensors 28, 30, 32, 34 and the second piece includes the leg portions 47, the inlet and outlet ports and other elements as shown. The pieces may be connected together by ultrasonic welding, solvent welding or adhesive bonding. Of course, other constructions (such as an integral, one-piece construction or a three-piece construction) are also possible.

As illustrated in FIGS. 1 and 4–6, the casing 16 has a first external threaded section that surrounds the inlet port of the first portion 20. The first threaded section is preferably constructed to matingly connect to an internally threaded Luer-type connector such as the male Luer connector 52 shown in FIG. 5 when the cassette 12 is in use for measuring parameters of fluid flowing through the chamber 18. The connector 52 has a ribbed portion for providing an interference-fit coupling to a section of flexible tubing 54 that directs fluid toward the chamber 18.

A second external threaded section surrounds the outlet port of the second fluid chamber portion 22. As shown in FIG. 5, a fitting 56 has an internal threaded section that matingly receives the second threaded section. The fitting 56 optionally includes a rearwardly extending collar having a radially inwardly extending rib 58. The casing 16 has a circumscribing, radially outwardly extending rib 60 adjacent the second threaded section that functions as a stop and provides a physical interference to the rib 58 in order to prevent detachment of the fitting 56 under normal circumstances whenever the fitting 56 is partially unthreaded from the casing 16.

The fitting 56 also includes another internal threaded section that is constructed to matingly receive a female Luer connector 62 (FIG. 5) when the cassette 12 is used with the measuring device 14 for measuring parameters of fluid flowing through the chamber 18. A section of flexible tubing 64 is connected in interference fit relation to a ribbed section of the connector 62 for directing the flow of fluid that exits the chamber 18.

FIG. 6 is a depiction for exemplary purposes of the cassette 12 during calibration of the sensors 28, 30, 32 and 34. During calibration, a gas filter assembly 66 replaces the connector 52 that is illustrated in FIG. 5 and has an internal threaded section that matingly receives the threaded section surrounding the inlet port of the first fluid chamber portion 20. An opposite end of the gas filter assembly 66 has a gas inlet opening 68 that is provided with a connector constructed with a partial screw thread. This connector is adapted to couple with a tubing connector (not shown) and the tubing, in turn, is connected to a source of calibration gas.

The gas filter assembly 66 has an enlarged, cylindrical central housing section that contains a disk-shaped section of filtering membrane 70. Preferably, the membrane 70 is made of a hydrophobic material (such as polytetrafluoroethylene) that is sterilized by autoclaving or a material (such as a modified acrylic) that is sterilized by radiation. A suitable modified acrylic material is VERSAPORE "H" brand membrane from Gelman Sciences. A network of nested, concentric circular channels and intersecting radial channels is provided throughout walls facing both sides of the membrane 70 to facilitate the passage of calibration gas through substantially all of the various regions of the membrane 70.

The gas filter assembly 66 also includes an outlet that receives a section of sparger tube 72. An example of a suitable tube 72 is a tube made of polyetheresterketone, having a 0.003 inch (0.075 mm) inner diameter and 0.012 inch (0.3 mm) outer diameter, from Zeus Products. A plug 74 surrounds the sparger tube 72 and secures the sparger tube 72 to the outlet of the filter assembly 66 in sealed relation. Examples of suitable material for the plug 74 include polycarbonate if the cassette 12 is to be sterilized by radiation and acrylic resin if the cassette 12 is to be sterilized by autoclaving.

When packaged for shipment to the end user, the cassette 12 preferably is provided with the filter assembly 66 as well as a cap 78 (FIG. 6) and a quantity of calibration fluid 80 received in the fluid chamber 18. For shipping purposes, the cap 78 is tightly threaded into the outlet section of the fitting 56 in sealed relation and the fitting 56 is tightened against the casing 16 (as shown in its orientation depicted in FIG. 5) to provide a fluid seal between the fitting 56 and the casing 16. Although not shown in the drawings, a shipping cap is securely coupled to the outer end of the filter assembly 66 for substantially preventing contaminants from entering the inlet opening 68 during transit and initial handling.

During calibration, the cassette 12 is oriented in an upright, preferably vertical position as shown in FIG. 6 and the fitting 56 is partially unthreaded by rotating the fitting 56 relative to the casing 16 in an arc about the longitudinal axis of the latter. During such motion, the fitting 56 is moved from a first position closing a gas outlet port and to a second position for opening or venting the gas outlet port. The ribs 58, 60 prevent inadvertent separation of the fitting 56 from the casing 16. Loosening of the fitting 56 relative to the casing 16 enables gas to flow from the second fluid chamber portion 22 to the atmosphere through the gas outlet port as depicted by the arrows in FIG. 6. Optionally, the outer peripheral wall of the rib 60 is provided with one or more channels 59 (see FIGS. 1 and 7) that extend in a direction parallel to the longitudinal axis of the casing 16 in order to facilitate the discharge of gas from the upper outlet port of the fluid chamber 18.

The quantity of calibration fluid 80 is preferably selected so that the level of fluid 80 in the chamber 18 during calibration extends across a lower section of the expansion zone portion 25 as illustrated in FIG. 6. Such a level decreases the likelihood that a portion of the calibration fluid 80 may escape through the upper outlet port, and yet assures that the fluid 80 fully covers the sensors 28, 30, 32, 34. Advantageously, the frustoconical configuration of the expansion zone portion 25 facilitates the rupture of calibration gas bubbles that pass through the fluid 80 in order to further decrease the likelihood of escape of the fluid 80 from the chamber 18. In addition, the hydrophilic surface on the wall sections of the chamber portion 24 facilitates the smooth passage of calibration gas bubbles past the sensors 28, 30, 32, 34. Optionally, an anti-foaming agent may be used in addition to or in place of the hydrophilic surface.

The calibration steps are described in further detail below. Once calibration is complete, the filter assembly 66 is removed from the casing 16 and replaced with the connector 52 that is depicted in FIG. 5. Additionally, the fitting 56 is tightened to its orientation as shown in FIG. 5 to provide a fluid leakage-resistant seal between the fitting 56 and the casing 16. The cap 78 that is shown in FIG. 6 is also removed and replaced with the connector 62 (FIG. 5), and the outer end of the connector 62 is coupled to the section of tubing 64. As will be described in more detail below, the sections of tubing 54, 64 enable the flow of fluid (such as blood) into and out of the chamber 18 for measuring parameters of the fluid.

The measuring device 14 that is shown in FIGS. 1 and 5 is also illustrated in more detail in FIGS. 8–20. The device 14 includes a two-part elongated housing 200 that is illustrated as it appears before assembly in FIG. 9. The two parts could be held by internal barbed connectors (for snap-together assembly) or by screws. Preferably, the housing 200 is made of an impact-resistant plastic material such as a mixture of polycarbonate and acrylonitrile-butadiene-styrene ("ABS") polymer, and has a smooth outer surface for facilitating disinfection. Optionally, the inner surface of the housing 200 is coated with an electromagnetally-compatible shielding material.

The measuring device 14 includes a second, female coupling 202 that is optionally made of a metallic material such as anodized aluminum. The coupling 202 has a concave recess with a generally U-shaped configuration in directions perpendicular to the longitudinal axis of the housing 200. The recess includes two flat, opposed sidewall sections 204 that are interconnected by a central bight section 206 (see, e.g., FIG. 1). Preferably, the opposed sidewall sections 204 converge as the bight section 206 is approached and extend along respective reference planes that are oriented at an angle in the range of about 28 degrees to about 32 degrees relative to each other. More preferably, the sidewall sections 204 extend along respective reference planes that are oriented at an angle of about 30 degrees relative to each other. An outer edge portion of each sidewall section 204 has an elongated groove 208 that extends in a direction parallel to the longitudinal axis of the housing 200.

Figure 9:
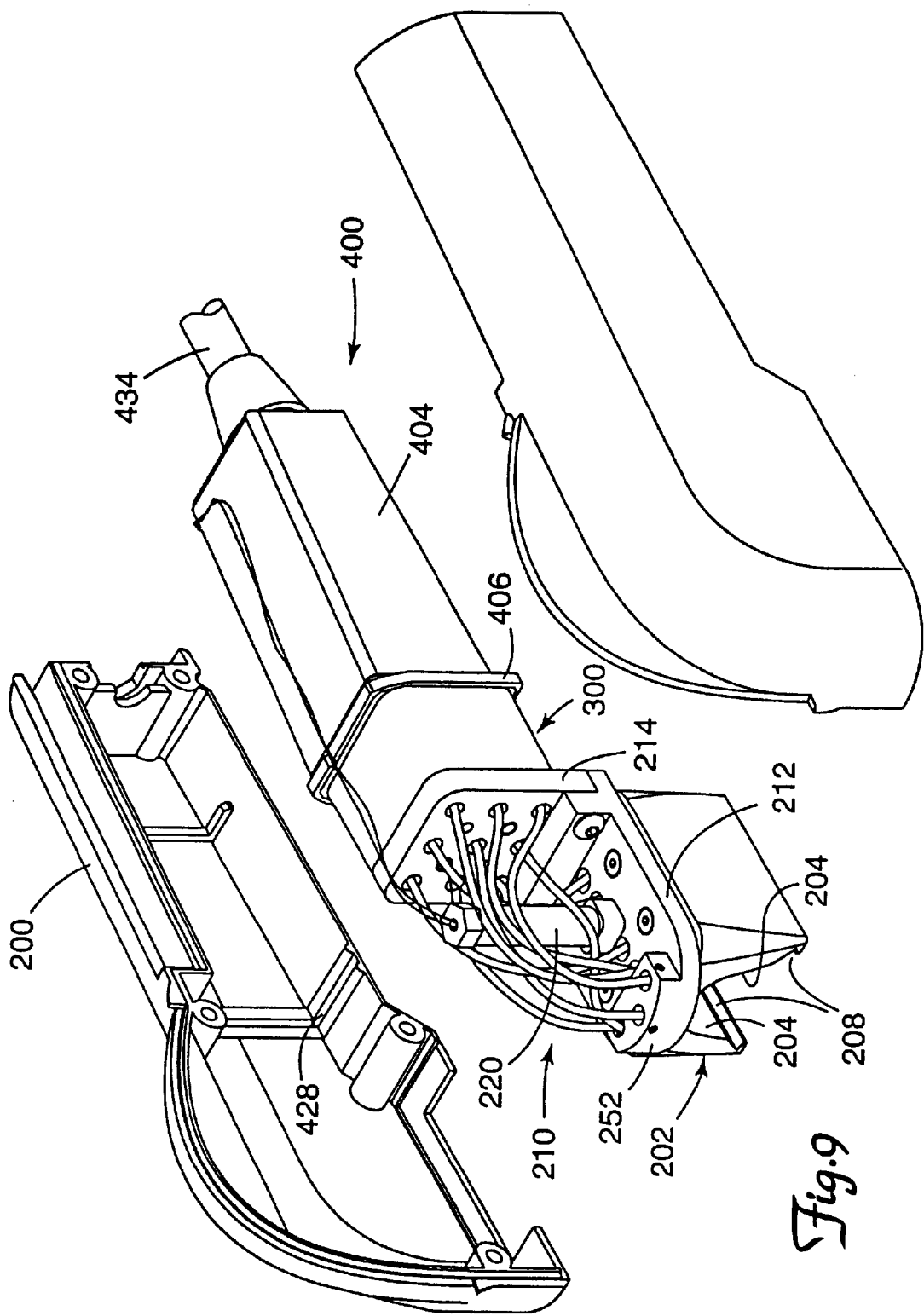
FIG. 9 is an exploded perspective view of the measuring device shown in FIG. 1.
Figure 10:
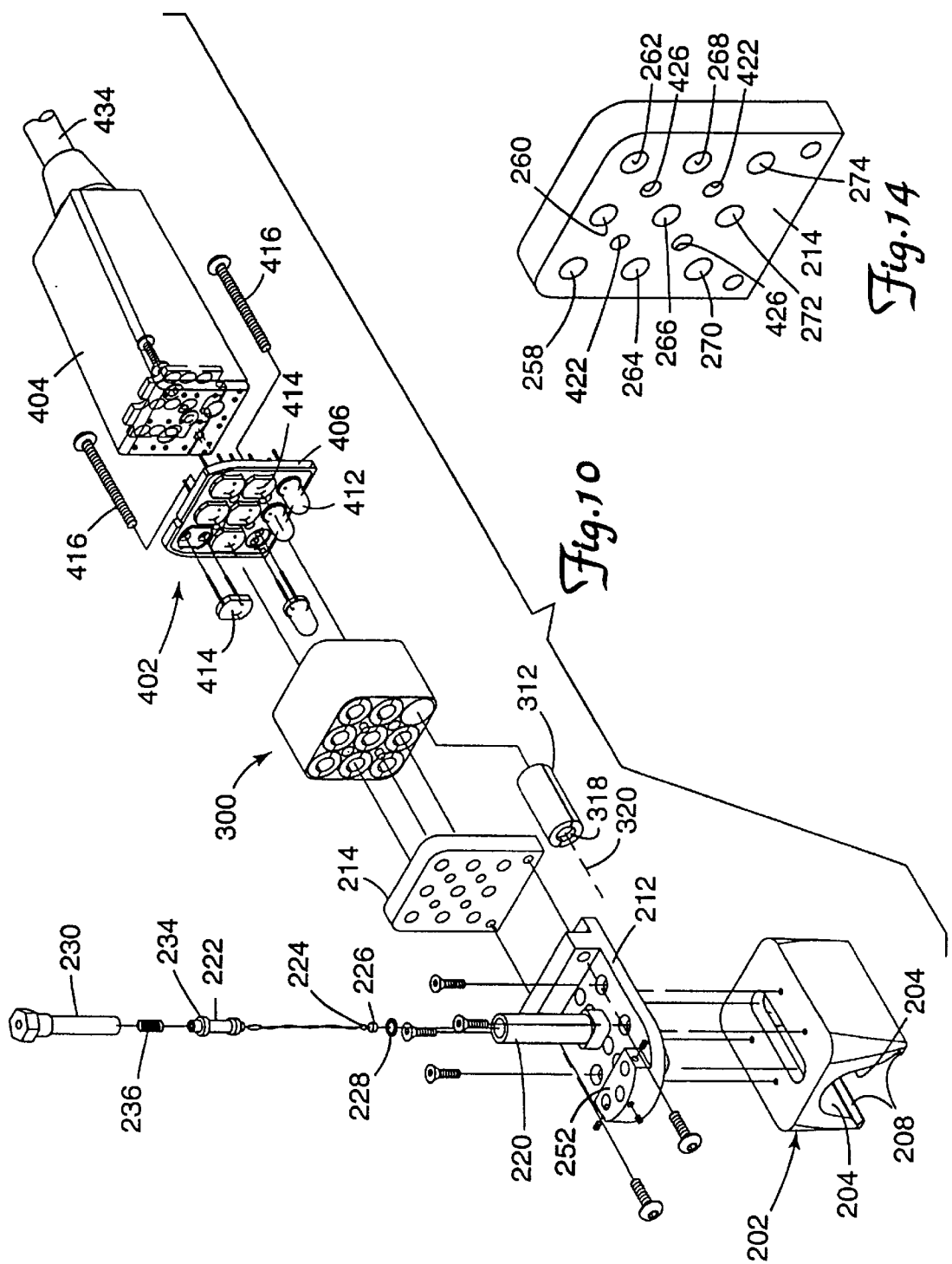
FIG. 10 is an enlarged, exploded perspective view of the measuring device of FIG. 1 except that a housing of the measuring device has been removed.
Figure 11:
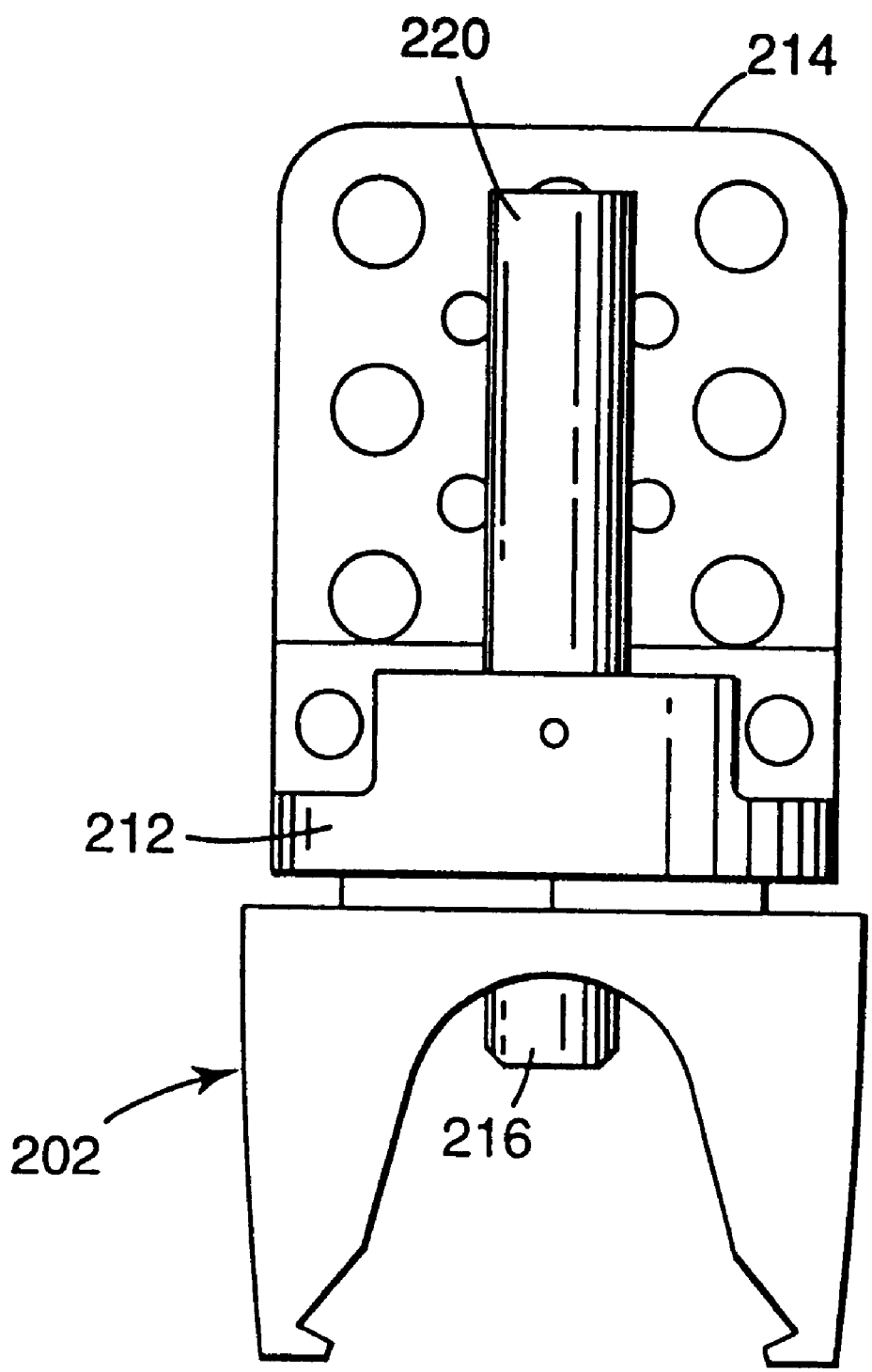
FIG. 11 is an enlarged end view of part of the measuring device of FIG. 1, looking in a direction parallel to a longitudinal axis of the device housing and showing among other items a fiber terminal block assembly.

The measuring device 14 includes a fiber terminal block assembly 210 (see, e.g., FIG. 9). The fiber block assembly 210 includes a fiber block insert plate 212 and a fiber block end plate 214 that are joined together by a pair of machine screws as depicted in FIG. 10. Preferably, the insert plate 212 is made of polycarbonate and the end plate 214 is made of aluminum.

The underside of the insert plate 212 is secured to the top of the coupling 202 by four machine screws that are illustrated in FIG. 10. The underside of the insert plate 212 includes a generally oval-shaped protrusion 216 (see, e.g., FIG. 12) having a major axis that is parallel to the longitudinal axis of the housing 200. The protrusion 216 includes a semi-cylindrical keyway 218 with a diameter that is just slightly larger than the diameter of the cassette key 42. Preferably, the keyway 218 is oriented such that a reference plane that bisects the keyway 218 along its central diametrical plane is also perpendicular to the longitudinal axis of the housing 200.

The protrusion 216 has a side wall that is matingly received and extends through an oval-shaped opening that is centrally located in the bight section 206 of the coupling 202. The outer side wall of the protrusion 216 has an oval-shaped configuration in bottom view that is complemental in shape to the oval-shaped configuration of the inner sidewall of the rim 40 of the cassette 12 (see, e.g. FIG. 4).

FIG. 5 illustrates the cassette 12 and a portion of the measuring device 14 when coupled together. When the measuring device 14 is connected to the cassette 12, the tabs 50 of the cassette 12 are received in respective grooves 208 of the measuring device 14. Furthermore, the outer surfaces 47 of the cassette support sections flatly contact the respective flat, facing surfaces of the measuring device sidewall sections 204. As can be appreciated, the first coupling 44 that is connected to the cassette casing 16 and the second coupling 202 that is connected to the housing 200 together represent a connector for releasably connecting the cassette 12 to the measuring device 14.

During assembly of the cassette 12 to the measuring device 14, the casing 16 is pushed in a direction toward the protrusion 216, and during such pushing motion the outer surfaces of the wedge-shaped tabs 50 function as a cam to deflect the leg portions 46 inwardly and toward each other until such time as the outer edge of each tab 50 is adjacent the respective groove 208. Once the outer edges of the tabs 50 are adjacent the grooves 208, the inherent bias of the leg portions 46 causes the latter to spread apart and return to their normal configuration in a snap-like manner such that the outer edges of the tabs 50 are received in the grooves 208 and thereby couple the cassette 12 to the measuring device 14.

The protrusion 216 has an outer end portion that matingly and snugly fits within the recess 26 when the measuring device 14 and the cassette 12 are connected together. In addition, when the measuring device 14 and the cassette 12 are connected together, the key 42 of the cassette 12 fits within the mating keyway 218 of the measuring device 14. Advantageously, the key 42 substantially prevents coupling of the cassette 12 to the measuring device 14 when an attempt is made to couple the cassette 12 to the measuring device 14 in an opposite fashion (i.e., in such a manner that the cassette 12 is oriented 180 degrees about a vertical reference axis from its orientation shown in FIG. 5).

The cassette 12 is detached from the measuring device 14 by squeezing the leg portions 46 together and moving the cassette 12 away from the device 14 until the tabs 50 clear the grooves 208. Although not shown in the drawings, outer sides of the coupling 202 are preferably each provided with a fingertip-sized recess to enhance the user's grip on the outer edge of the cassette flanges 48 during detachment of the cassette 12 from the measuring device 12. The recesses also help guide the user's finger toward a position for engaging the center of the flanges 48 at a location close to the tabs 50.

The fiber terminal block assembly 210 includes an upstanding polycarbonate tube 220 that is solvent-welded to the insert plate 212 and receives a thermistor assembly. As shown in FIGS. 5 and 10, the thermistor assembly includes a thermistor support 222 having a central internal passageway and a necked-down lower end section. A thermistor 224 is mounted partially within a cavity of the lower end section of the thermistor support 222 and has a pair of leads that extend through the passageway. An example of a suitable thermistor is part no. SC30BF103A-L8 from Thermometrics.

A cap 226 (see FIG. 5) made of a material such as stainless steel covers the thermistor 224 and is secured by potting compound to a circumscribing side wall of the lower end section of the support 222. The cap 226 has a thermal conductivity that is high relative to the thermal conductivity of the adjacent plastic material. The potting compound (such as no. H20 from Epo-tek) substantially fills the space between the inner surface of the cap 226 and the external surface of the thermistor 224 and facilitates heat transfer between the cap 226 and the thermistor 224.

The support 222 is received in an internal, generally cylindrical passage of the tube 220, and an O-ring 228 located in a peripheral groove of the support 222 provides a fluid-resistant seal. The support 222 is kept in the passage of the tube 220 by a retainer 230 having an upper threaded section that is threaded into a mating threaded section of the tube 220.

The passage of the tube 220 narrows to a somewhat smaller diameter near its lower end and presents an annular shoulder 232 that is depicted in FIG. 5. The support 222 includes an upper, circumscribing cylindrical rib 234 having an outer diameter that is larger than the internal diameter of the tube passage in regions beneath the shoulder 232. In addition, a helical compression spring 236 (see also FIG. 10) extends between and bears against the lower end of the retainer 230 and an upwardly facing annular wall of the rib 234. The spring 236 yieldably biases the support 222 in a downwardly direction viewing FIG. 5 such that the rib 234 comes to rest against the shoulder 232 when the measuring device 14 is not coupled to the cassette 12.

When the cassette 12 and the measuring device 14 are not coupled together, the lower end of the thermistor cap 226 protrudes beneath the bottom of the plate 212 a distance that is greater than the depth of the well 36 of the cassette 12 relative to the top surface of the recess 26 when viewing FIG. 5. As such, as the cassette 12 is coupled to the measuring device 14, the cap 226 contacts the bottom of the well 36 and urges the support 222 in an upwardly direction against the bias of the spring 236. Once the coupling 44 and the coupling 202 are connected together, the spring 236 tends to retain the bottom of the cap 226 in a position of close contact with the bottom of the well 36 to increase the effective contact area between the cap 226 and the well 36 and reduce thermal resistance. The inner configuration of the well 36 is preferably somewhat complemental and more preferably is closely complemental to the external configuration of the cap 226 in order to improve heat transfer along a path from the fluid in the central portion 24 of the chamber 18, across the joint between the well 36 and the cap 226, and ultimately to the thermistor 224.

Figure 13:
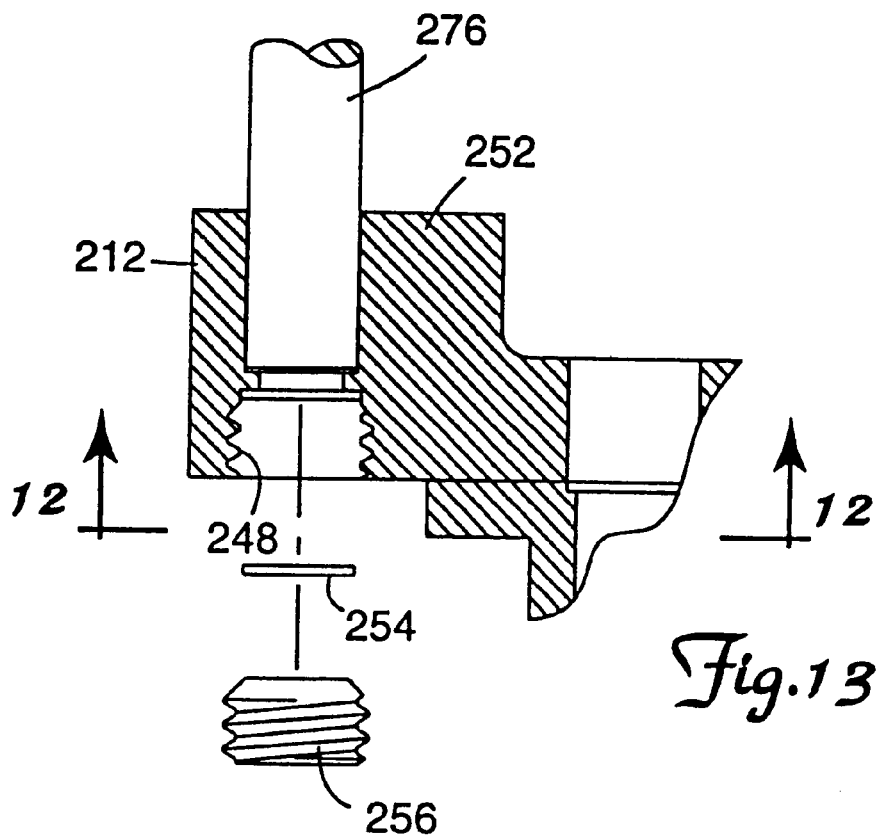
FIG. 13 is an enlarged side cross-sectional view of a portion of the fiber terminal block assembly that is depicted in FIG. 11.
Figure 12:
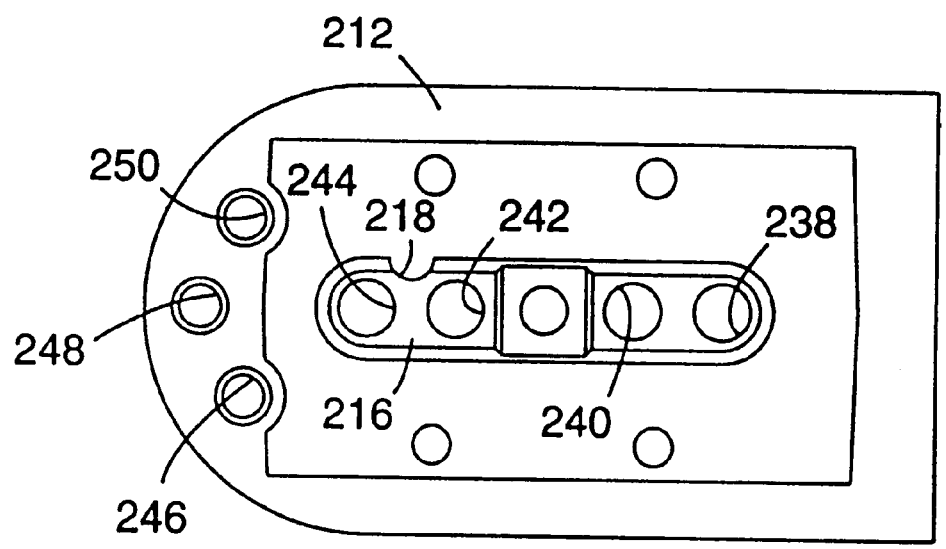
FIG. 12 is an enlarged bottom view of the fiber terminal block assembly shown in FIG. 11.

With reference to FIG. 12, the insert plate 212 includes four holes 238, 240, 242 and 244 that extend through the protrusion 216 and are arranged in spaced-apart relation along the major axis of the oval-shaped protrusion 216. In addition, the bottom plate includes three holes 246, 248, 250 that are spaced from the protrusion 216 and extend through a raised platform 252 (see FIGS. 10 and 13) located on an upper, outer end section of the insert plate 212. As shown in FIG. 13, a disk 254 made of an optical reference material is placed in the hole 248 and is secured against a shoulder of the hole 248 by a set screw 256 that is threaded into a lower threaded section of the hole 248. The optical reference disk 254 is preferably made of a fluorescing material (such as a 0.002 weight percent fluorescent material in polycarbonate). A suitable fluorescent material is a high quantum efficiency fluorescent dye, such as "MACROLUX 10GN" brand material from Bayer.

Figure 15:
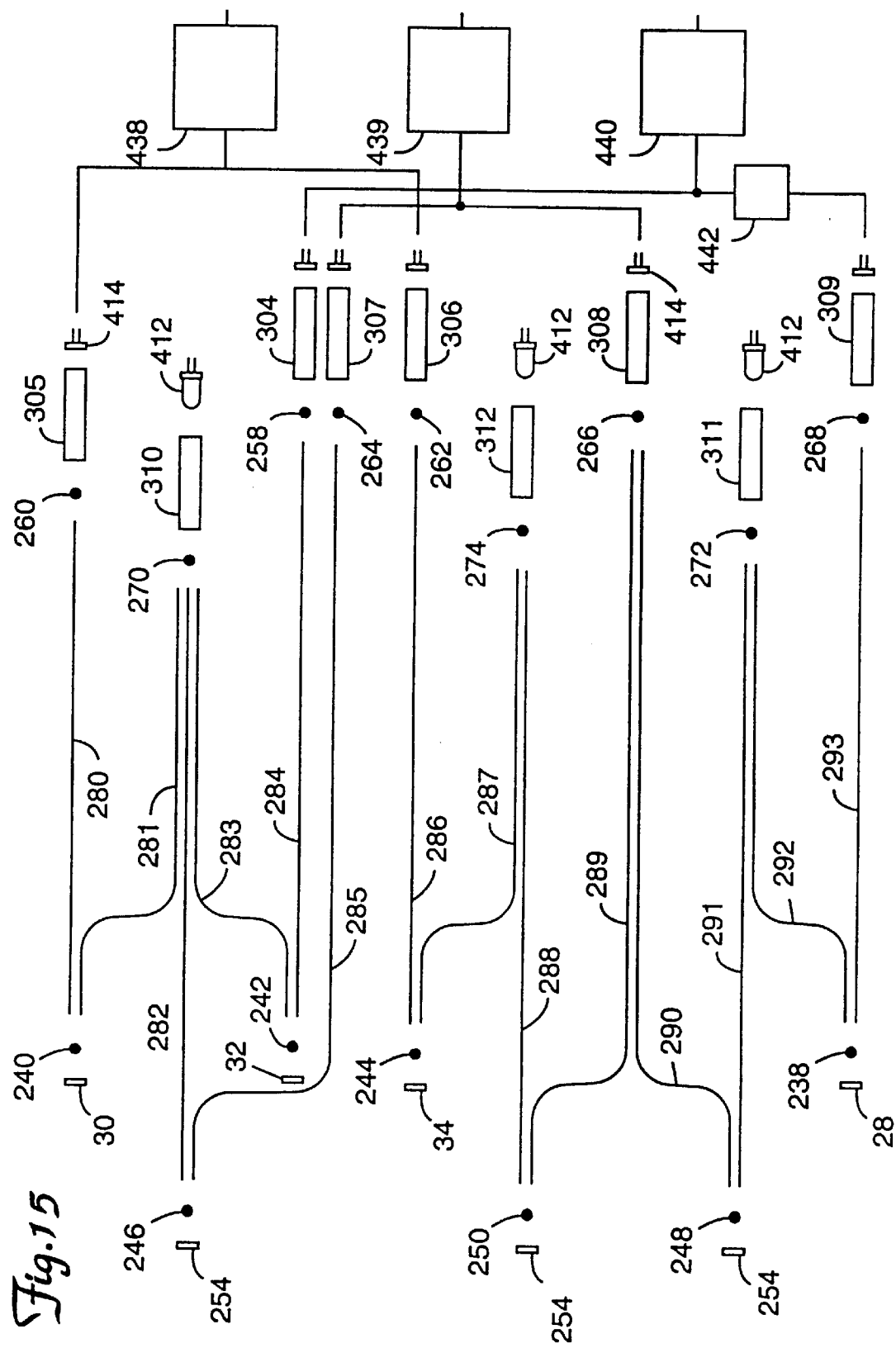
FIG. 15 is a schematic illustration showing among other things the various paths of optical fiber bundles of the measuring device illustrated in FIG. 1.

The holes 246, 250 are identical to the hole 248 and each receives a set screw similar to set screw 256 and an optical reference disk 254a, 254b (shown numbered only in FIG. 15). The optical reference disk 254a in the hole 246 is identical to the optical reference disk 254. The optical reference disk 254b in the hole 250 is similar to the optical reference disk 254 but is instead preferably made of a 0.0035 weight percent fluorescent material dissolved in polycarbonate.

The end plate 214 of the fiber terminal block assembly 210 has nine holes 258–274 that are numbered in FIG. 14. The holes 258–274 are arranged in an array of three rows with three holes in each row. The holes 258–274 as well as the holes 238–250 are each adapted to receive a ferrule surrounding an end of a bundle of optical fibers. An exemplary ferrule is designated by the numeral 276 in FIG. 13. An example of a suitable material for the ferrules received in holes 246–250 is brass or stainless steel, an example of a suitable material for the ferrules received in holes 238–244 is stainless steel and an example of a suitable material for the ferrules received in holes 258–274 is brass or aluminum. Optionally, the platform of the bottom plate includes three small threaded openings (see FIGS. 10 and 13), each of which intersects with one of the holes 246, 248, 250. Those small openings are each adapted to threadably receive a small set screw (not shown) that secures the ferrule in the adjacent hole 246, 248, 250 to the platform in order to facilitate assembly.

The fiber terminal block assembly 210 includes a number of bundles of optical fibers. The optical fiber bundles are omitted from all of the views except that an exemplary network (not accurately depicted) of bundles is shown in FIG. 9 for purposes of explanation. A schematic of the various optical fiber bundles is illustrated in FIG. 15 and shows the true preferred various paths of the optical fiber bundles between the holes 238–250 and the holes 258–274.

In more detail, and with reference to FIG. 15, the fiber terminal block assembly 210 includes a first bundle of optical fibers 280 that extends between the hole 240 and the hole 260, a second bundle of optical fibers 281 that extends between the hole 240 and the hole 270, a third bundle of optical fibers 282 that extends between the hole 246 and the 270, a fourth bundle of optical fibers 283 that extends between the hole 242 and the hole 270, a fifth bundle of optical fibers 284 that extends between the hole 242 and the hole 258, a sixth bundle of optical fibers 285 that extends between the hole 246 and the hole 264, a seventh bundle of optical fibers 286 that extends between the hole 244 and the hole 262, an eighth bundle of optical fibers 287 that extends between the hole 244 and the hole 274, a ninth bundle of optical fibers 288 that extends between the hole 250 and the hole 274, a tenth bundle of optical fibers 289 that extends between the hole 250 and the hole 266, an eleventh bundle of optical fibers 290 that extends between the hole 248 and the hole 226, a twelfth bundle of optical fibers 291 that extends between the hole 248 and the hole 272, a thirteenth bundle of optical fibers 292 that extends between the hole 238 and the hole 272 and a fourteenth bundle of optical fibers 293 that extends between the hole 238 and the hole 268.

A suitable optical fiber for each of the various bundles 280–293 is a fiber having a nominal outer diameter of 0.0022 inch (56 micron), with core glass of Schott LF5 or F2, clad glass of Schott 8250 Corning 7056 or 7052 and a clad thickness of 0.00008 to 0.00012 inch (2–3 microns). Preferably, although not necessarily, all of the optical fibers in the various bundles 280–293 are identical. Of course, other types of fibers and number of fibers in each of the bundles 280–293 may be different from the description set out above.

Preferably, an optical adhesive such as "Epo-tek" brand optical epoxy no. 301 or 301-2 is used to secure bundled ends of the fibers into the ferrules (such as ferrule 276) to present optical apertures. The bundles 280–293 are preferably coated with a non-fluorescing, optically opaque stiff plastic or rubber material. Ends of some of the bundles 280–293 are intermixed to present bifurcated sections such that the optical fibers received in one ferrule may lead to different ferrules at the opposite ends of the fibers as depicted schematically in FIG. 15. Moreover, the optical fibers of each optical aperture are randomized (i.e., the fibers of each optical aperture are spatially well-mixed even in instances where the fibers pass through bifurcated sections). For example, the fibers of the optical aperture in hole 240 are randomized such that no circular area having a diameter of 0.020 inch (0.5 mm) or greater exists that has less than three fibers originating from either of the bundles 280, 281.

An example of a suitable number of optical fibers for the middle region of each bundle 280–293 is set out below in Table I. (For purposes herein, the "middle" regions shall mean a central section of the bundle along its length at a location between its ends and any bifurcated sections.) Table II identifies the target number of optical fibers and overall diameter of the optical aperture (which may include fibers originating from one or more than one bundle) in the ferrules placed in each of the holes 238–250 and 258–274. The values in Tables I and II are based on optical fibers having an outer diameter of 56 microns as mentioned above and a packing fraction of 70 percent (i.e. the area occupied by the fibers divided by the overall, circular area of the optical aperture). Since small optical fibers are difficult to count during assembly, the manufacturer may instead prefer to measure the diameter of a bundle to more quickly determine by estimation the number of optical fibers in the bundle.

TABLE I

| Bundle Number | Target Number of Optical Fibers Middle Region of Bundle |
|---|---|
| 280 | 1150 |
| 281 | 375 |
| 282 | 200 |
| 283 | 375 |
| 284 | 1150 |
| 285 | 600 |
| 286 | 1150 |
| 287 | 375 |
| 288 | 200 |
| 289 | 600 |
| 290 | 600 |
| 291 | 200 |
| 292 | 375 |
| 293 | 1150 |

TABLE II

| Hole Number | Target Number of Optical Fibers in Optical Aperture | Diameter of Optical Aperture | |
|---|---|---|---|
| | | Inch | mm |
| 238–244 | 1525 | 0.104 | 2.64 |
| 246–250 | 800 | 0.076 | 1.93 |
| 258–262 | 1150 | 0.089 | 2.26 |
| 264 | 600 | 0.067 | 1.70 |
| 266 | 1200 | 0.093 | 2.36 |
| 268 | 1150 | 0.089 | 2.26 |
| 270 | 950 | 0.081 | 2.06 |
| 272–274 | 575 | 0.064 | 1.62 |

Figure 16:
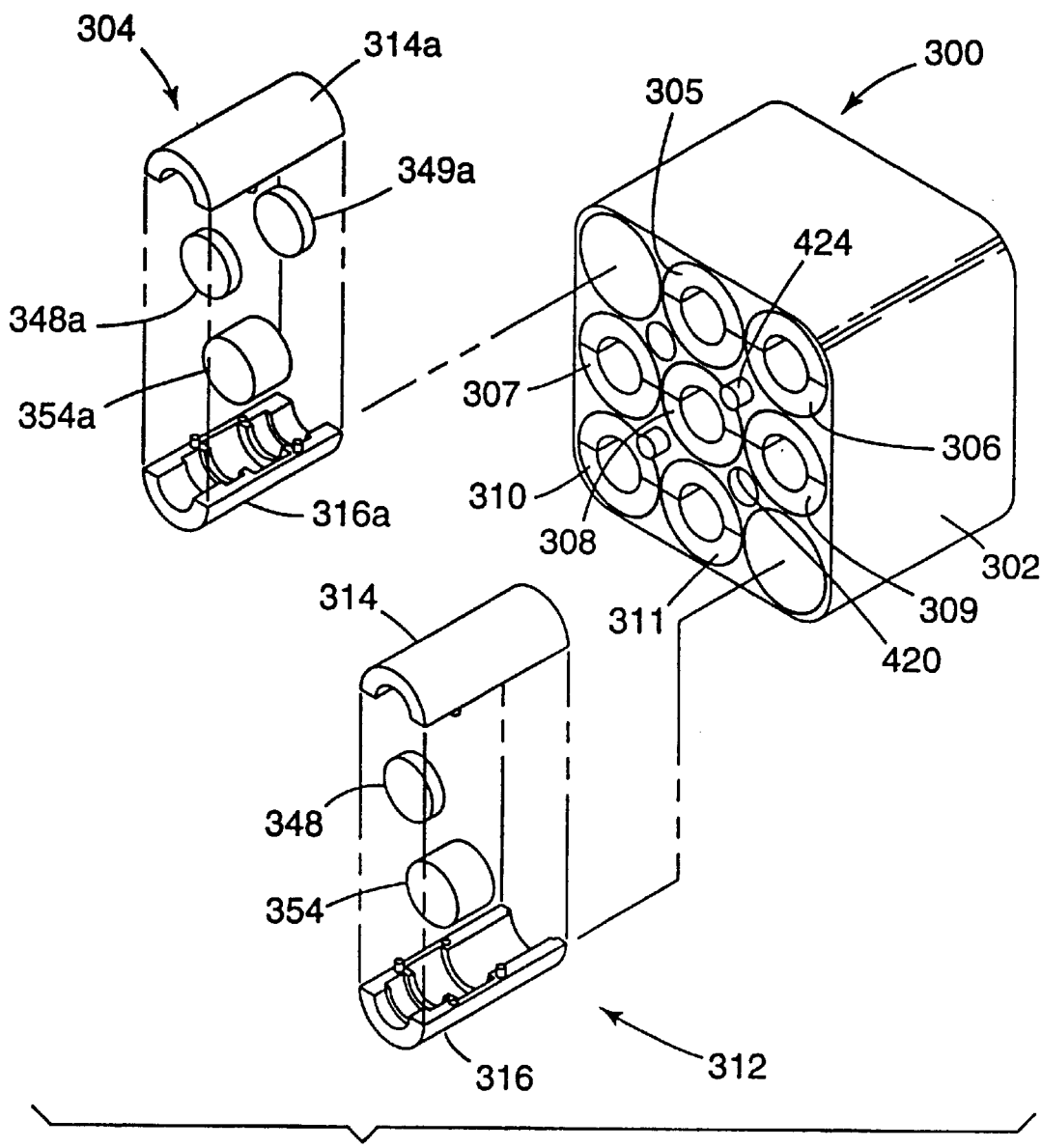
FIG. 16 is an enlarged perspective view in partially exploded form of part of an optics assembly of the measuring device of FIG. 1.

The measuring device 14 also has an optics assembly 300 which includes a block 302 as well as nine optic subassemblies 304–312 (which are numbered in FIG. 16 only). The block 302 has nine cylindrical cavities symmetrically arranged in three rows with three cavities in each row, and one of the optic subassemblies 304–312 is received in each cavity. Preferably, the block 302 is made of a material having a thermal conductivity similar to metal. An example of a suitable material is aluminum. The block 302 could also be made of a ceramic material having an appropriate thermal conductivity.

The optic subassemblies numbered 310, 311 and 312 are excitation optic subassemblies, and the subassembly 312 is illustrated in exploded view in FIG. 16 for exemplary purposes. The subassembly 312 includes a first optical retainer 314 and a second optical retainer 316 which is identical to the first retainer 314. When the retainers 314, 316 are connected together in the manner shown in FIG. 10, internal wall sections of the retainers 314, 316 together present an elongated chamber 318 having a somewhat cylindrical overall configuration with a central, longitudinal reference axis 320.

Figure 17:
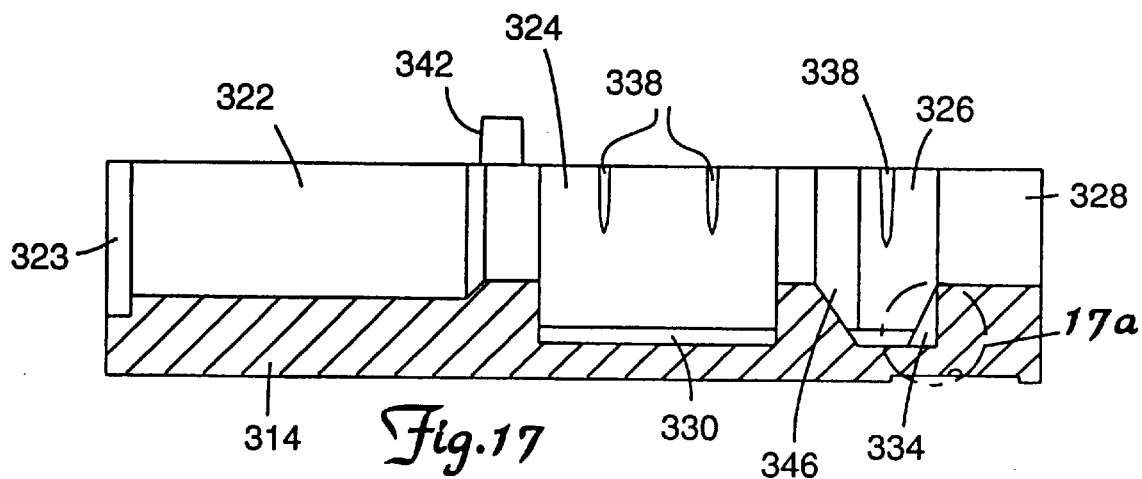
FIG. 17 is an enlarged cross-sectional view taken along a longitudinal axis of one optical retainer of the optics assembly depicted in FIG. 16.
Figure 19:
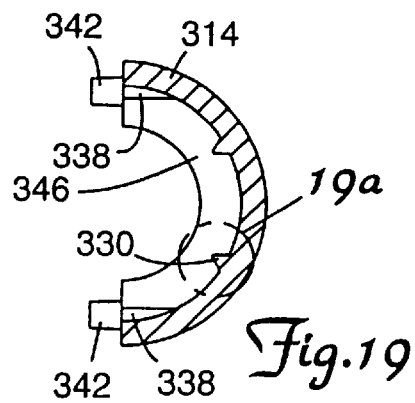
FIG. 19 is a cross-sectional view of the retainer illustrated in FIGS. 16–17, taken along a reference plane perpendicular to the longitudinal axis of the retainer.

The first retainer 314 is shown alone in FIGS. 17–19. The retainer 314 has internal wall sections that define a first chamber portion 322 (FIGS. 17 and 18), a second chamber portion 324, a third chamber portion 326 and a fourth chamber portion 328. When the retainers 314, 316 are connected together in the manner shown in FIG. 10, the first chamber portions 322 of the retainers 314, 316 present a generally cylindrical light inlet port having a shape for enshrouding a light emitting diode (as described in more detail below), the second chamber portions 324 present a generally cylindrical subchamber for receiving an optical filter, the third chamber portions 326 present a subchamber for receiving an optical lens, and the fourth chamber portions 328 present a generally cylindrical light outlet port. A small cylindrical opening extends between and communicates the light inlet port with the optical filter subchamber, and a second, small cylindrical opening extends between and communicates the optical filter subchamber with the lens subchamber.

Figure 19A:
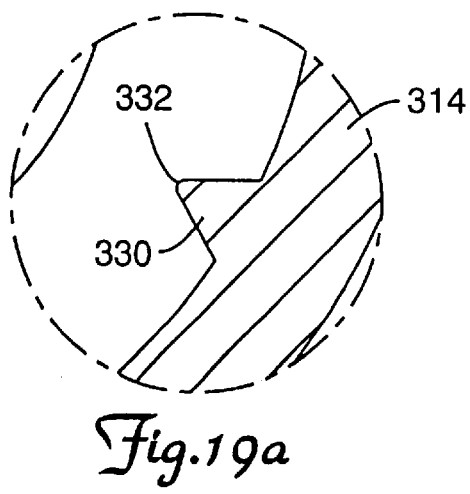
FIG. 19a is an enlarged view of a portion of the retainer shown in FIG. 19.

The wall sections of the retainer 314 defining the chamber portions 324, 326 are each connected to a first set of one or more ribs 330. In the embodiment shown in the drawings, the first set includes two spaced apart ribs 330 that extend in a direction parallel to the central axis 320. Each of the ribs 330 (see, e.g. FIG. 18) preferably extends the entire length of the respective chamber portions 324, 326 and has an outermost deformable tip portion 332 that is shown in more detail in FIGS. 19a. The deformable tip portion 332 may be elastomeric (i.e., it self-returns to its original shape after the force causing the deformation is removed) or non-elastomeric.

Figure 17A:
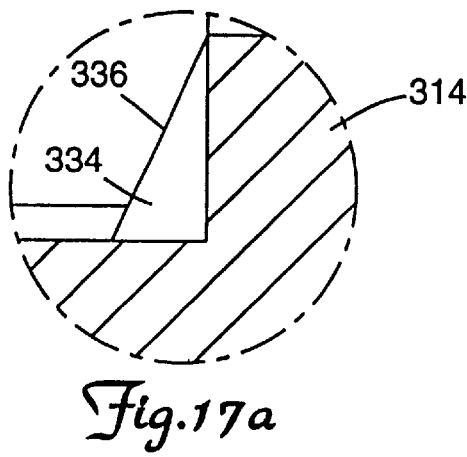
Figure 17B:
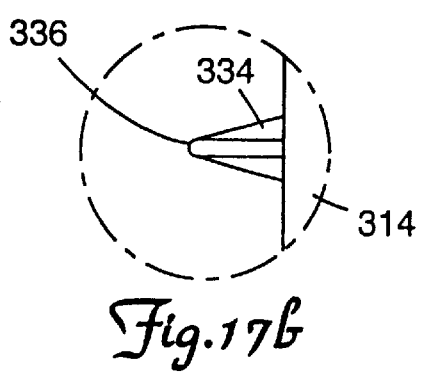

The retainer 314 also includes a second set of one or more ribs 334. In the embodiment shown in the drawings, the second set of ribs 334 consists of a single rib that is located along a radial wall section of the third chamber portion 326 directly adjacent the fourth chamber portion 328. The rib 334 has an overall configuration of a triangle in side view as illustrated in FIGS. 17 and 17a, and also has an outermost deformable (elastomeric or non-elastomeric) tip portion 336 that is shown enlarged in FIGS. 17a and 17b.

The second chamber portion 324 and the third chamber portion 326 also include a third set of one or more ribs 338 that extend in reference planes perpendicular to the central axis 320. Six ribs 338 are shown in the embodiment illustrated in FIGS. 17–19. Four of the ribs 338 are located in the second chamber portion 324, and are arranged in opposing fashion such that one pair of ribs 338 extend in a first common reference plane perpendicular to the central axis 320 and the other pair of ribs 338 extend in a second reference plane perpendicular to the central axis 320. The two remaining ribs 338 are located in the third chamber portion 326 and extend in another common reference plane that is perpendicular to the central axis 320. An exemplary rib 338 is shown enlarged in FIG. 17c, and each rib 338 includes an outermost deformable tip portion 340 that may be either elastomeric or non-elastomeric.

The retainer 314 has a symmetrical, diametrical wall section with a pair of pegs 342 and a pair of matching holes 344. One peg 342 and one hole 344 have parallel central reference axes that extend in a common plane perpendicular to the central axis 320. Similarly, the other peg 342 and the other hole 344 also have respective central reference axes that extend in a common plane that is perpendicular to the central axis 320 but spaced from the aforementioned reference plane containing the central axes of the other peg 342 and hole 344.

The wall sections defining the third chamber portion 326 also include an annular, chamfered wall section 346 that extends in a semi-circular path about the central axis 320. The lens subchamber consequently has an overall configuration that includes a generally cylindrical portion and an aligned frustoconical portion having common central axes that are collinear with the central axis 320. Since the retainer 316 is identical to the retainer 314, a detailed description of the retainer 316 need not be provided.

When the retainers 314, 316 are connected together in the manner shown in FIG. 10, the pegs 342 of the retainer 314 are received in the holes 344 of the retainer 316 and the pegs 342 of the retainer 316 are received in the holes 344 of the retainer 314. Preferably, at least one mating pair of the pegs 342 and holes 344 are closer to one end of the subassembly 312 than the other end. As such, if an attempt is made to connect the retainers 314, 316 together in such a manner that the first chamber portions 322 are not opposed from each other and instead are located at opposite ends, the ends of the retainers 314, 316 will not be aligned and provide a readily apparent visual indication to the assembler that the retainers 314, 316 have not been properly oriented with respect to each other.

Figure 16A:
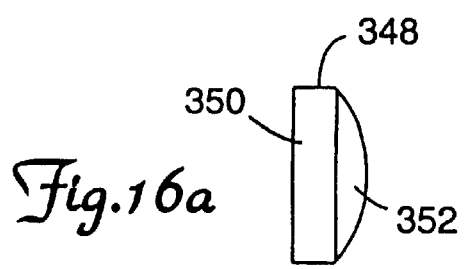
FIG. 16a is an enlarged side elevational view of a lens of the optics assembly illustrated in FIG. 16.

A plano-convex lens 348 (see FIGS. 16 and 16a) is received in the third chamber portions 326, and includes a cylindrical portion having an outer peripheral cylindrical wall 350 and a convex, dome-shaped portion having an outer wall 352 with a configuration of a partial sphere. The central diametrical axis of the dome-shaped portion and the central axis of the cylindrical portion lie along a common reference axis known as the optical axis of the lens 348. An example of a suitable lens has a 6 mm focal length and a diameter of 6 mm such as part no. 45078 from Edmund Scientific. Preferably, the orientation of the chamfered wall section 346 of the third chamber portions 326 (relative to the central axis 320) is somewhat similar to the orientation of the engaged region of the outer wall 352 (relative to the central axis of the dome-shaped portion) in areas where the sections 346 contact the outer wall 352 as the retainers 314, 316 are assembled together.

During assembly, and as the retainers 314, 316 are closed around the lens 348, the cylindrical wall 350 comes into contact with the ribs 330, 334, 338 in interference fit relation. As the retainers 314, 316 approach a fully closed, connected together orientation, tie tip portions 332, 336, 340 in the lens subchamber crush and deform while exerting respective forces on the lens 348 in certain directions. More specifically, as the retainers 314, 316 are closed, the tip portions 332, 340 of the first and third set of ribs 330, 338 direct a force on the lens 348 in a radially inwardly direction toward the central axis 320, while the tip portions 336 of the second set of ribs 334 direct a force on the lens 348 having vector components extending in radially inward directions toward the central axis 320 as well as vector components extending parallel to the central axis 320 in directions toward the chamfered wall sections 346.

The orientation of the ribs 330, 334, 338 that are located in the third chamber portions 326 is selected to guide the lens 348 into proper concentric relationship so that the optical axis of the lens 348 is aligned in parallel with and preferably precisely collinear with the central axis 320. As the retainers 314, 316 are closed together, the optical axis of the lens 348 is shifted as necessary by the ribs 330, 334, 338 and brought into a position that coincides with the central reference axis 320. The ribs 334 urge the dome-shaped outer wall 352 into a position of snug contact with the chamfered wall sections 346. The ribs 334 also exert a force on the lens 348 that is sufficient to pivot the lens 348 upon the wall sections 346 and shift the rear, flat face of the cylindrical lens portion next to the light outlet port 328 into an orientation such that the rear face is precisely perpendicular to the central axis 320 once the retainers 314, 316 are closed. The ribs 330, 338 function to shift the lens 348 in a lateral direction as the retainers 314, 316 are closed so that the optical axis of the lens 346 is collinear with the central axis 320.

As the retainers 314, 316 are closed, the deformable tip portions 332, 336, 340 cold flow to accommodate the configuration of the lens 348 (and any surface irregularities) and secure the lens 348 in place. Such deformable tip portions 332, 336, 340 (along with other regions of the plastic retainers 314, 316) also tend to protect the lens 348 from damage when the optics assembly 300 or the measuring device 14 is subjected to impact or vibration.

The second chamber portions 324 of the retainers 314, 316 are adapted to receive an optical filter 354. The filter 354 that is shown in FIG. 10 for exemplary purposes has a cylindrical configuration with a central axis. As the retainers 314, 316 are brought toward a closed, connected-together orientation, the tip portions 332 of the ribs 330 located in the second chamber portions 324 and the tip portions 340 of the ribs 338 located in the second chamber portions 324 crush and deform, and urge the filter 354 to such an orientation that the central axis of the filter is collinear with the central axis 320 of the subassembly 312. Once the retainers 314, 316 are fully closed, the ribs 330, 338 snugly engage the cylindrical side wall of the filter 354 and securely retain it in place.

The retainers 314, 316 when closed together present a smooth cylindrical outer surface having a diameter that is preferably closely similar or identical to the internal diameter of the hole of the block 302 receiving the subassembly 312. More preferably, the cylindrical outer surface presented by the retainers 314, 316 when assembled together is slightly larger than the hole in the block 302 receiving the subassembly 312 in order to establish a slight interference fit between the block 302 and the subassembly 312. Once the subassembly 312 is received in the hole, the retainers 314, 316 remain assembled together without the need for adhesive, fasteners or the like. Alternatively, however, an adhesive or mechanical fastener could be provided to hold the retainers 314, 316 in the block.

Each of the retainers 314, 316 is preferably integrally-molded and made of a relatively soft, deformable plastic material such as an ABS polymer or a blend of ABS polymer and polycarbonate. An example of a suitable ABS polymer is no. 8540H from TAITALAC. Preferably, the material has a limited cold flow and yet is sufficient elastic to securely hold the optical component in place.

Optionally, the tip portions 332, 336, 340 or alternatively the entire ribs 330, 334, 338 are made of a plastic material that has a higher modulus of elasticity than the modulus of elasticity of the plastic material of the remainder of the retainers 314, 316. Insert molding, for example, could be used to provide tip portions 332, 336, 340 that are made of a material different than the remainder of the material of the retainers 314, 316. In any case, the material of the tip portions 332, 336, 340 and/or the entire ribs 330, 334, 338 is selected such that each tip portion 332, 336, 340 snugly engages and retains a force on the lens 348 and/or the filter 354 even after repeated cycles of temperature fluctuations. Preferably, the retainers 314, 316 are made of a material that has a smaller thermal conductivity than the thermal conductivity of the material of the block 302, in order to help insure that the temperature of the lens 348 and the filters 354 of the various subassemblies 304–312 is substantially identical even during periods of temperature fluctuation of the block 302.

The excitation optic subassemblies 310, 311 are identical to the excitation optic subassembly 312 with the exception of the optical filters. In particular, the optical filter 354 of the subassembly 312 has an overall diameter of 0.25 inch (6 mm) and a length of 0.145 inch to 0.175 inch (3.6 to 4.4 mm), has a pass band with a center wavelength of 398 nm and transmits 50% of peak transmission at wavelengths of 385 nm and 410 nm. The optical filter for the subassembly 311 is identical to the filter 354 except that the optical filter for the subassembly 311 has a pass band with a center wavelength of 413 nm and transmits 50% of peak transmission at wavelengths of 400 nm and 425 nm. The optical filter for the subassembly 310 is identical to the filter 354 except that the optical filter for the subassembly 310 has a pass band with a center wavelength of b 475 nm and transmits b 50% of peak transmission at wavelengths of 460 nm and 490 nm. Other aspects of the subassemblies 310, 311 are identical to the subassembly 312 and as such a detailed description of the subassemblies 310, 311 need not be provided.

However, the optic subassemblies 304–309 are emission optic subassemblies and are somewhat different than the excitation optic subassemblies 310–312 as can be appreciated by reference to the subassembly 304 that is shown in exploded view in FIG. 16. The subassembly 304 includes two retainers 314a, 316a that are essentially similar to the retainers 314, 316 except for the differences set out below. The retainer 314a alone is illustrated in FIGS. 20 and 21. The retainers 314a, 316a are identical and as such a detailed description of the retainer 314a will suffice to describe the retainer 316a as well. The retainer 314a has internal wall sections that define a first chamber portion 322a, a second chamber portion 324a, a third chamber portion 326a, a fourth chamber portion 328a and a fifth chamber portion 329a. When the retainers 314a, 316a are connected together, the first chamber portions 322a present a generally cylindrical light inlet port and the fourth chamber portions 328a present a generally cylindrical light outlet port. Moreover, when the retainers 314a, 316a are closed, the second chamber portions 324a present a generally cylindrical filter sub-chamber for receiving an optical filter 354a similar to the filter sub-chamber of subassembly 312, and the third chamber portions 326a present a first lens sub-chamber for receiving an optical lens 348a similar to the lens sub-chamber of the subassembly 312. The fifth chamber portions 329a when the retainers 314a, 316a are closed present a second lens sub-chamber for receiving an optical lens 349a that is similar to the first lens sub-chamber of the subassembly 304, but the second lens sub-chamber is oriented 180 degrees opposite from the orientation of the first lens sub-chamber with respect to a central reference axis of the subassembly 304.

The retainer 314a has first, second and third sets of ribs 330a, 334a, 338a respectively that are preferably identical to the first rib set 330, the second rib set 334 and the third rib set 338 of the subassembly 312. As a consequence, as the retainers 314a, 316a are closed, the ribs 330a, 334a, 338a function to shift the lenses 348a, 349a as well as the filter 354a as necessary to bring the optical axes of the lens 348a, 349a and the central axis of the filter 354a into parallel alignment and preferably collinear alignment with the central axis of the subassembly 304 once assembled. The retainers 314a, 316a also each have two pegs and two mating holes similar to the pegs 342 and holes 344 of the retainers 314, 316. Preferably, however, the peg and hole on each side of each retainer 314a, 316a are spaced apart from each other a distance that is somewhat different than the spacing between the pegs 342 and holes 344 of the retainers 314, 316 in directions parallel to the central axis 320, in order to reduce the likelihood that one of the retainers 314, 316 is accidentally connected to one of the retainers 314a, 316a.

The emission optic subassemblies 305–309 are each identical to the emission optic subassembly 304 except for the optical filters. Specifically, the optical filter 354a of the subassembly 304 as well as the optical filters for the subassemblies 305, 307 are each identical to the filter 354 described above except that the filters for the subassemblies 304, 305, 307 have a pass band with a center wavelength of 550 nm and transmit 50% of peak transmission at wavelengths of 515 nm and 585 nm. The optical subassembly 306 has an optical filter that is identical to the filter 354 except that the optical filter for the subassembly 306 has a pass band with a center wavelength of 485 nm and transmits 50% of peak transmission at wavelengths of 450 nm and 520 nm. The optical filters for the subassemblies 308, 309 are identical to the filter 354 except that the optical filters for the subassemblies 308, 309 have a pass band with a center wavelength of 500 nm and transmit 50% of peak transmission at wavelengths of 465 nm and 535 nm. The lenses 348a, 349a of the subassembly 304 as well as the corresponding lenses of the subassemblies 305–309 are each identical to the lens 348 described above.

The retainers 314, 314a, 316, 316a provide important advantages, inasmuch as they not only secure the lenses 348, 348a, 349a and the filters 354, 354a in proper alignment but also present built-in apertures for receiving light emitting diodes and photodiodes as described in further detail below. In addition, the retainers 314, 314a, 316, 316a provide molded, built-in light inlet ports and light outlet ports of a suitable size for adjacent optical apertures. The retainers 314, 314a, 316, 316a provide an inexpensive yet simple and efficient means for manufacture and assembly of the various components without the need for gaskets or washers as is common with other optical assemblies (such as, for example, conventional optical assemblies wherein lenses, filters and washers are dropped in sequence into a cylindrical chamber of a one-piece housing).

Those skilled in the art will recognize that the concepts of the mating retainers and an optical block may also be used for other optical assemblies such as binoculars, telescopes and the like. Moreover, a useful assembly may be provided by molding lenses and/or optical filters in place and integral with one of the retainers. As another alternative, the retainers could be constructed to present folded or offset optic axes such as is often provided for, e.g. binoculars. If the assembly is to be used in applications where rapid heat transfer between the block and the retainers is desired (for example, in assemblies where the optic components are heated), the retainers could be made of a material other than plastic and a thermal potting compound could be placed between the retainers and the block.

Although the optics assembly 300 as described in detail above is presently preferred, an alternative optics assembly may be constructed by eliminating the block 302 and providing other structure to hold the retainers together and to also hold the subassemblies together as a group if desired. For example, rings or snap-action clips may be constructed to hold each pair of retainers together, and a framework, grid, strapping or other structure may be provided to hold assembled pairs of the retainers to other assembled pairs of retainers. Optionally, the configuration of each assembled pair of retainers may be a shape other than cylindrical such as hexagonal, square, rectangular or triangular in instances where it is desired to establish flat, face-to-face contact between adjacent retainer pairs and avoid air gaps (as may be desired, for example, to facilitate heat transfer). As another option, each retainer may be provided with structure (such as snap-action pegs or tabs or a mortise and tenon arrangement) to interlock with the other retainer of that subassembly, or to interlock with retainers of other subassemblies.

As an additional option, a number of retainers for a number of different subassemblies may be integrally molded together in side-by-side relation as an array that is then connected to a similar array after the optical components are in place in each subassembly chamber, in order to reduce the number of parts that might otherwise be separately handled. For example, three retainers similar to retainers 316 in FIG. 16 could be integrally molded and then assembled to three retainers similar to the retainers 314 in FIG. 16 (with the option, as explained above, that each retainer 314 is identical to each retainer 316). Moreover, the backs of the retainers of one row could be integrally molded to the backs of the retainers of the adjacent row to further reduce the number of parts in any one optics assembly. Further, the assembled pairs of such retainers could have shapes other than cylindrical such as hexagonal, square, rectangular, triangular or the like as mentioned above.

Figure 22:
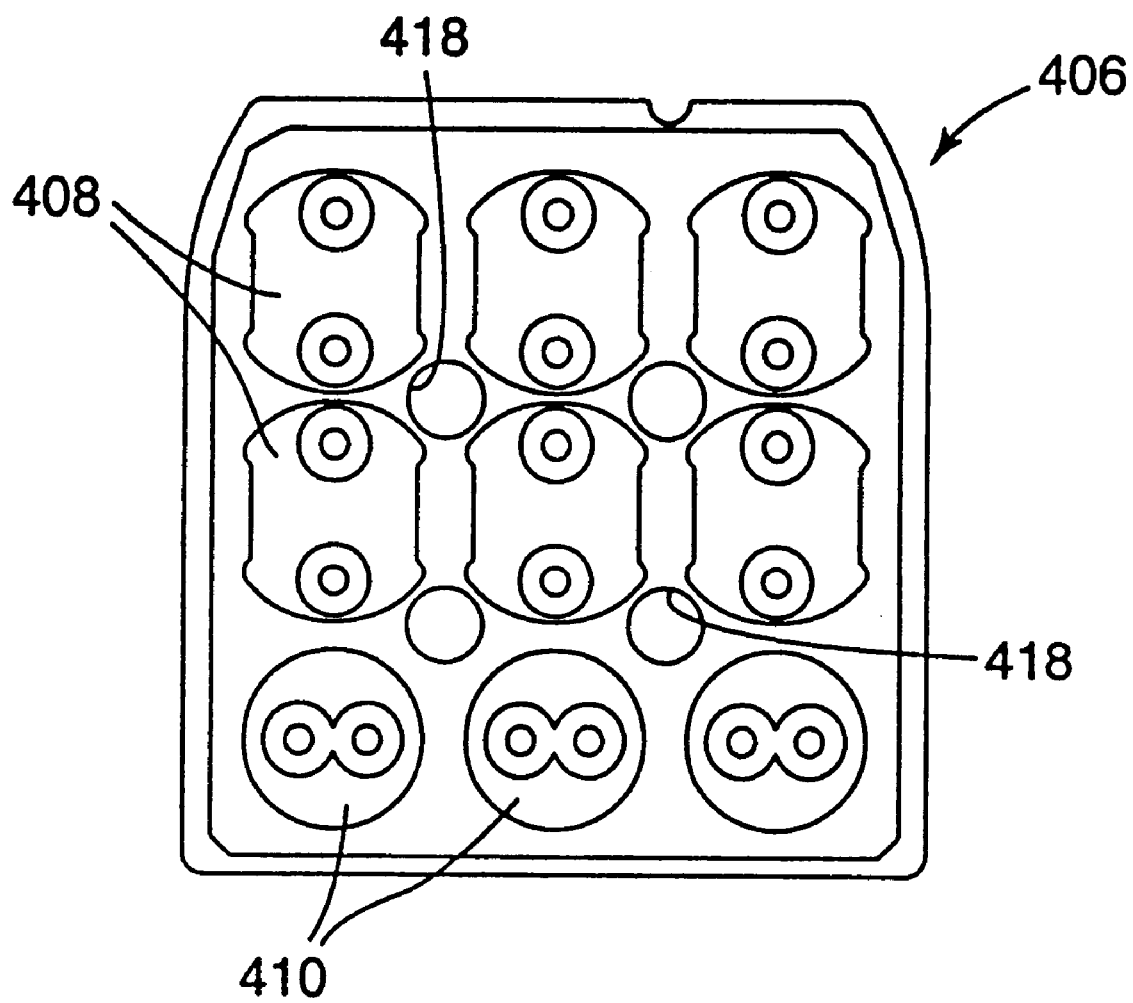
FIG. 22 is an enlarged elevational view of an electro-optics coupling plate of the measuring device shown in FIG. 1.

The measuring device 14 also includes an electrical assembly 400 (see, e.g., FIG. 9) that includes an electro-optics subassembly 402 and a printed circuit board subassembly 404 having a printed circuit board substrate and various electronic components mounted on the substrate. The electro-optics subassembly 402 includes a coupling plate 406 (see also FIG. 22) having six somewhat oval-shaped recesses 408 that are arranged in two rows with three recesses 408 in each row. The coupling plate 406 also includes three circular recesses 410 that are arranged along a single row and in columnar alignment with the recesses 408, such that the recesses 408, 410 present an array of nine recesses with three recesses in each of three rows.

Preferably, at least a portion of the coupling plate 406 is made of an elastomeric material. As one example, the coupling plate 406 may include an aluminum substrate that is covered or partially covered with an elastic material such as polyurethane or silicone. Optionally, the substrate presents recesses corresponding to the recesses 408, 410, and a layer of elastomeric material is received in each recess. Optionally, the elastomeric material extends past the four edges of the metal substrate and covers the entire extent of a flat rear surface of the metal substrate that faces away from the optics assembly 300. Preferably, the elastomeric material is electrically non-conductive and has holes that are aligned with but somewhat smaller than the holes in the metal provided for electrical leads. As such, the leads are kept out of contact with the aluminum substrate.

The electro-optical subassembly 402 includes three light emitting diodes or "LEDs" 412 (see FIGS. 8 and 10), each of which have a circular base that is snugly received in a respective one of the recesses 410. Each LED 412 also has a dome-shaped portion that is snugly, complementally received in the light inlet port presented by the first chamber portions of the respective retainers of subassemblies 310–312. The retainers of subassemblies 310–312 also have a circular cavity (see, e.g., cavity 323 in FIGS. 17 and 18) for receiving the remainder of the circular base of the corresponding LED. An example of a suitable LED is a gallium nitride LED such as part no. NLPB-500 from Nichia or alternatively a laser diode.

The electro-optics subassembly 402 also includes six solid state light detectors or photodiodes 414, each of which includes a body that is partially and snugly received in a respective one of the recesses 408. The photodiodes 414 may be either silicone photodiodes or avalanche photodiodes. An example of a suitable silicon photodiode 414 is part no. S1133-14 from Hamamatsu. The LEDs 412 as well as the photodiodes 414 each include a pair of leads that extend through respective holes of the coupling plate 406, and in particular through the holes of the metal substrate and elastomeric material as described above.

A pair of machine screws 416 (see FIG. 10) extend through a folded-over portion of the printed circuit board substrate, through respective holes 418 (see FIG. 22) of the coupling plate 406, through respective holes 420 (see FIG. 16) of the block 302 and are threaded into matingly-threaded holes 422 (see FIG. 14) of the fiber block end plate 214. Preferably, the block 302 is also provided with a pair of protruding, parallel alignment posts 424 that are received in respective holes 426 (see FIG. 14) of the insert plate 214 to facilitate assembly. Once the screws 416 are tightened into the insert plate 214, the elastic material extending over the substrate of the coupling plate 406 provides a yieldable layer that helps to prevent damage to the electrical assembly 400 whenever the measuring device 14 is subject to physical shock forces as may occur, for example, whenever the measuring device 14 is accidentally dropped.

As shown for example in FIG. 9, a peripheral edge portion of the coupling plate 406 protrudes outwardly from adjacent areas of the optic block 302 as well as the printed circuit board subassembly 404. The peripheral edge portions of the coupling plate 406 are received in channels 428 of the two parts of the housing 200. The protruding, peripheral edge portions of the coupling 406 in combination with the channels 428 provide a stable mounting support for the optics assembly 300 and the electrical assembly 400, and also serve to reduce the amount of convective heat that would otherwise flow from the area within the housing 200 surrounding the printed circuit board subassembly 404 to the area within the housing 200 surrounding the remainder of the components including the optics assembly 300 and the fiber block assembly 210.

Figure 23:
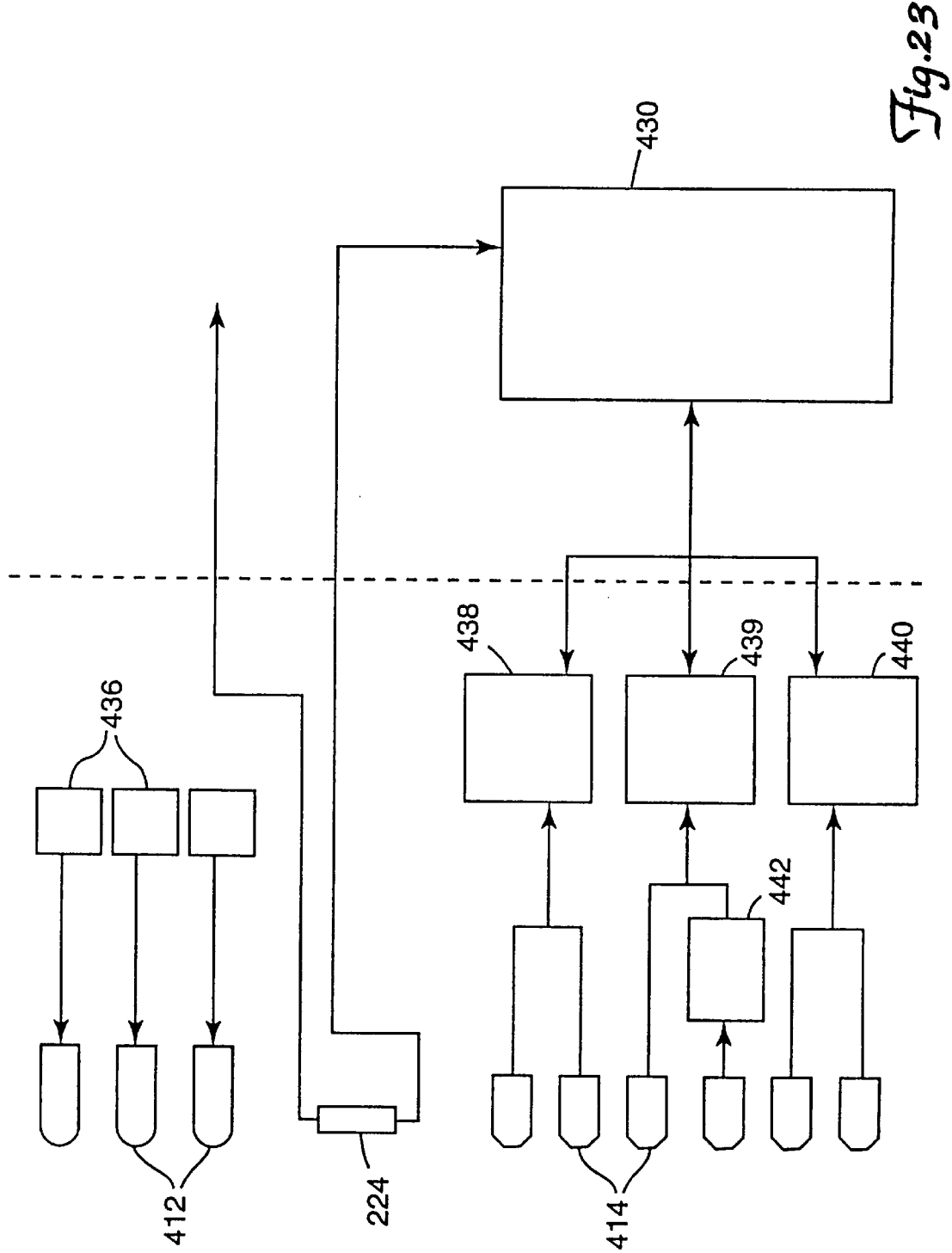
FIG. 23 is a schematic block diagram of an electrical assembly of the device of FIG. 1 as well as part of a monitor.
Figure 24:
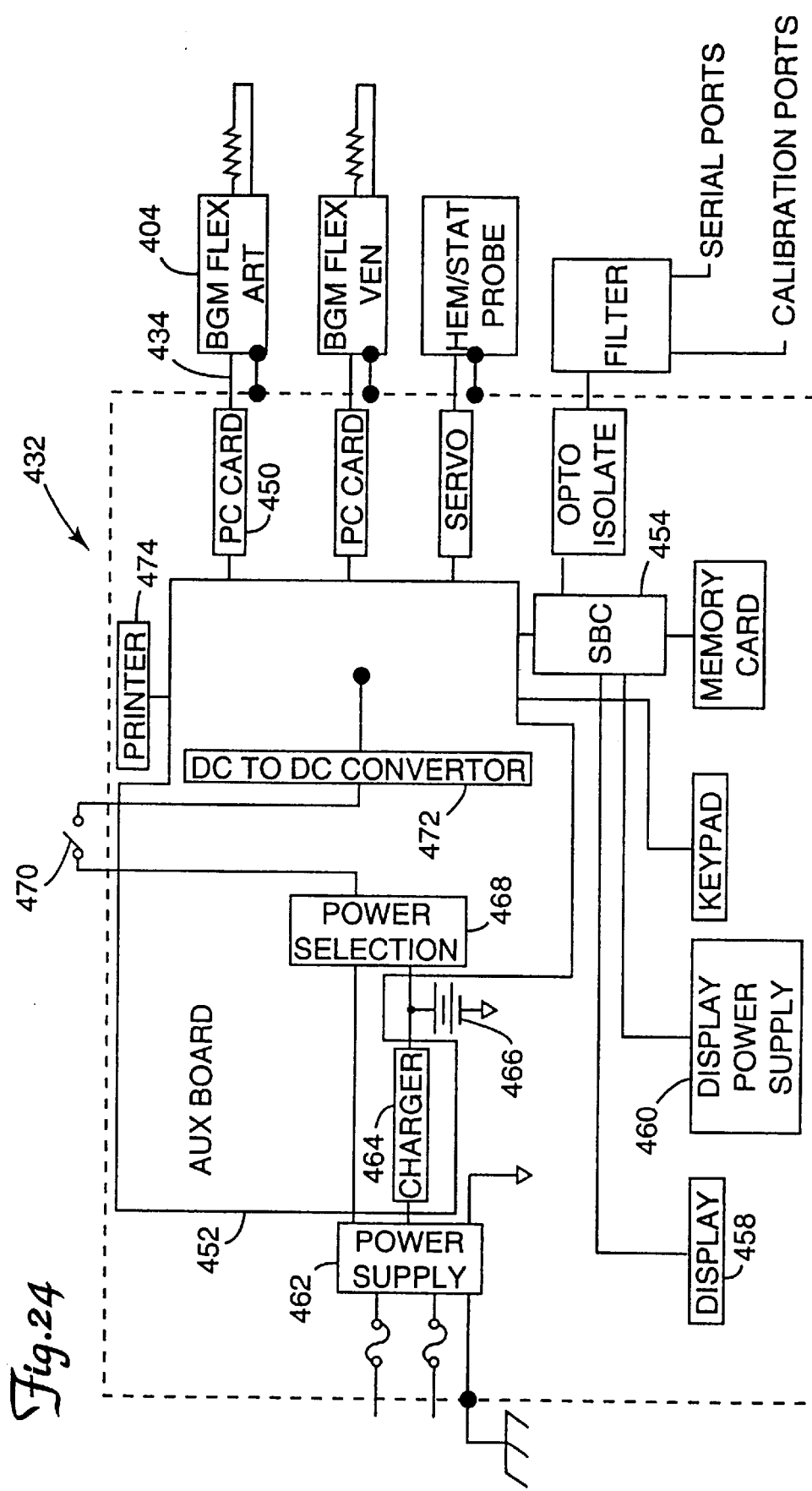
FIG. 24 is a schematic block diagram of the monitor, also showing connection to the device of FIG. 1 along with connection to other devices.

The printed circuit board subassembly 404 includes a controller 430 (see FIG. 23) that receives power, clock timing and instructional signals from a remote monitor 432 (see FIG. 24). A flexible electrical cable 434 (FIG. 8) operatively interconnects the controller 430 and the monitor 432. As another option, however, the electrical assembly 400 may be powered by batteries located in or adjacent to the housing 200 and the electrical cable 434 replaced by a bundle of optical fibers or by a telemetric communication device such as a device providing radio frequency or optical frequency signals.

Figure 8:
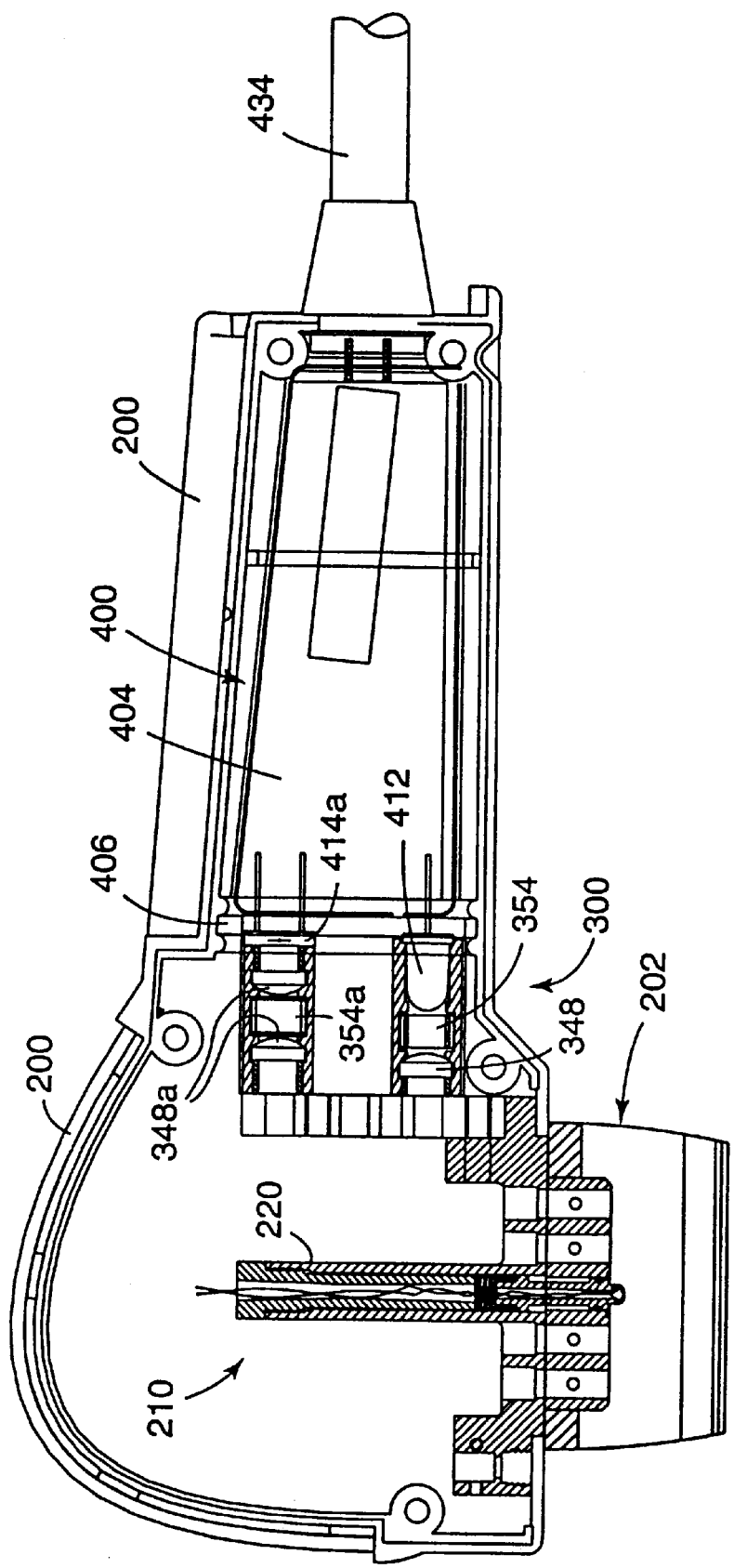
FIG. 8 is an enlarged side cross-sectional view of the measuring device alone that is illustrated in FIG. 1, except that optical fibers within the device have not been shown.

The printed circuit board substrate of the subassembly 404 is folded into a rectangular, box-like configuration as shown in FIGS. 8–10. The box-like configuration includes four side portions and two end portions that surrounds the space where the electronic components on the substrate are mounted. Such construction advantageously provides electrical shielding for the electronic components and also serves to somewhat thermally isolate the components from the LEDs.

The controller 430 is electrically connected (connection not shown in drawings) to three drivers 436 that, in turn, are each electrically connected to a corresponding one of the LEDs 412. The drivers 436 energize the respective LEDs 412 in sequence in accordance.

The printed circuit board subassembly 404 includes three analog-to-digital converters 438, 439, 440 that are shown in FIG. 23 as well as in FIG. 15. A suitable analog-to-digital converter is catalog no. DDC101 from BURR-BROWN. As schematically depicted in FIG. 15, the converter 438 is electrically connected to the photodiodes 414 associated with the optic subassemblies 305 and 306, the converter 439 is electrically connected to the photodiodes 414 associated with the optic subassemblies 307 and 308 and the converter 440 is electrically connected the diode 414 associated with the optic subassemblies 304, 309. Additionally, a signal amplifier or opamp 442 (such as catalog no. AD795 from Analog Devices) is interposed in the electrical lead between the photodiode 414 of the subassembly 309 and the converter 439.

In use, the controller 430, upon receiving a certain signal from the monitor 432, directs a signal to one of the drivers 436 which, in turn, energizes the corresponding one of the LEDs 412. Light then travels from that LED 412 through the adjacent optical fibers of the fiber block assembly 210 and to the corresponding sensor 28–34 where it is absorbed. The sensor then emits light at a different wavelength. The amount of emitted light is determined by the analyte concentration (such as calibration fluid or blood) in the fluid chamber 18 of the cassette 12. Light emitted from such sensor 28–34 is directed through other optical fibers of the fiber block assembly 210 and to one of the photodiodes 414, and the converter 438–440 that is electrically connected to that diode 414 provides a digital output signal that is representative of the amount of light flux detected. The controller 430, in accordance with a preselected time delay interval, reads data received from the appropriate converter 438–440 and passes such data to the monitor 432 via cable 434.

The optical filter 354 within each of the excitation optic subassemblies 310–312 serves to pass substantially all of the light having wavelengths within its pass band and block substantially all of the light having wavelengths that are not within the pass band. The lens 348 of each excitation optic subassembly 310–312 focuses light emitted from the optical filter 354 onto the optical aperture of the adjacent fiber optic bundle.

Light that is emitted from the sensors 28–34 and directed to the emission optic subassemblies 304–309 passes from the optical aperture of the adjacent fiber optic bundle to the corresponding lens 348*a*. The lens 348*a* serves to collummate and direct the light along the optical axis to the adjacent optical filter 354*a*. The second lens 349*a* then focuses the light onto the corresponding, adjacent photodiode 414. The filter 354*a* passes most of the light having wavelengths within the pass band and blocks substantially all of the light having wavelengths outside of the pass band. For any given optical pathway, the filter 354 selects the wavelengths of light that excite the fluorescent dye in the corresponding sensor 28–34, and blocks substantially all other light. The filter 354*a* selects the wavelengths of light that have been emitted by the fluorescent dye and block substantially all remaining light (including any reflected excitation light).

The converters 438–440 convert the analog signal received from the photodiodes 414 into a digital data stream that is representative of the amount of light flux sensed by the photodiodes 414. The digital data is forwarded to the controller 430 which, in turn, sends the data to the monitor 432.

FIG. 15 shows that the light emitted from the LED 412 that is received in the subassembly 310 is simultaneously directed to the sensor 30, the sensor 32 and the reference disk 254 adjacent the hole 246. Light emitted from the sensor 30 is detected by the photodiode 414 next to the subassembly 305 and converted to a digital signal by the converter 438. Light emitted from the reference disk 254 next to the hole 246 is detected by the photodiode 414 of subassembly 307 and is converted to a digital signal by the converter 439. Light that is detected from the sensor 32 by the photodiode 414 adjacent the subassembly 304 is converted to a digital data stream by the converter 440. The digital data stream from the three converters 438–440 is received by the controller 430 and forwarded to the monitor 432.

In somewhat similar fashion, the light emitting from the LED 412 of the subassembly 312 is directed to the sensor 34 as well as the reference disk 254 that is adjacent the hole 250. Light emitted from the sensor 34 is detected by the photodiode 414 next to the subassembly 306, and the analog output of the photodiode 414 is converted to a digital data stream by the converter 438. At the same time, light emitted from the reference disk 254 adjacent the hole 250 is detected by the photodiode 414 next to the subassembly 308, and the analog signal from that photodiode 414 is converted to a digital data stream by the converter 439.

When the LED 412 of the subassembly 311 is energized, light is directed simultaneously to the sensor 28 and to the reference disk 254 that is adjacent the hole 248. Light emitted from the reference disk 254 adjacent the hole 248 is detected by the photodiode 414 next to the subassembly 308, and the analog output of the photodiode 414 is changed to a digital data stream by the converter 439. Light that is emitted from the sensor 28 is detected by the photodiode 414 next to the subassembly 309, and the analog output from that photodiode 414 is amplified by amplifier 442 and directed to the converter 440 which changes the analog signal to a digital data stream.

The schematic shown in FIG. 15 enables the use of only three converters 438–440 even though four sensors (i.e., sensors 28–34) and three reference disks 254 are in use, and also enables the use of only three LEDs 412. Such a time sharing or "multiplexing" arrangement conserves the number of components needed for the electrically assembly 400 and also conserves space so that the housing 200 may be relatively small. In addition, such an arrangement reduces the amount of heat that might otherwise be generated within the housing 200.

A schematic block diagram of the monitor 432 is shown in FIG. 24. The monitor 432 includes an interface card 450 that is connected to the cable 434 leading from the electrical subassembly 404. The interface card 450 is electrically coupled to an auxiliary board 452 that, in turn, is connected to a primary controller or "SBC" (single board computer) 454. The interface card 450 also provides power to the LEDs 412.

The SBC controls the amplitude and duration of the pulse drive to the LEDs 412. The SBC 454 is connected to a memory card 456 as well as a display 458 such as an LED display. A power inverter 460 for the display 458 is also connected to the SBC 454.

The monitor 432 also includes a power supply 462 that is connected to a source of line voltage. The power supply 462 is electrically coupled to a charger 464 that maintains a battery 466 in charged condition. The power supply 462 as well as the battery 466 are connected to a power selector 468. The monitor 432 includes a switch 470 that, when closed, sends power to three DC/DC converters 472. The DC/DC converters 472 as well as a printer 474 are both electrically coupled to the auxiliary board 452.

Figure 25:
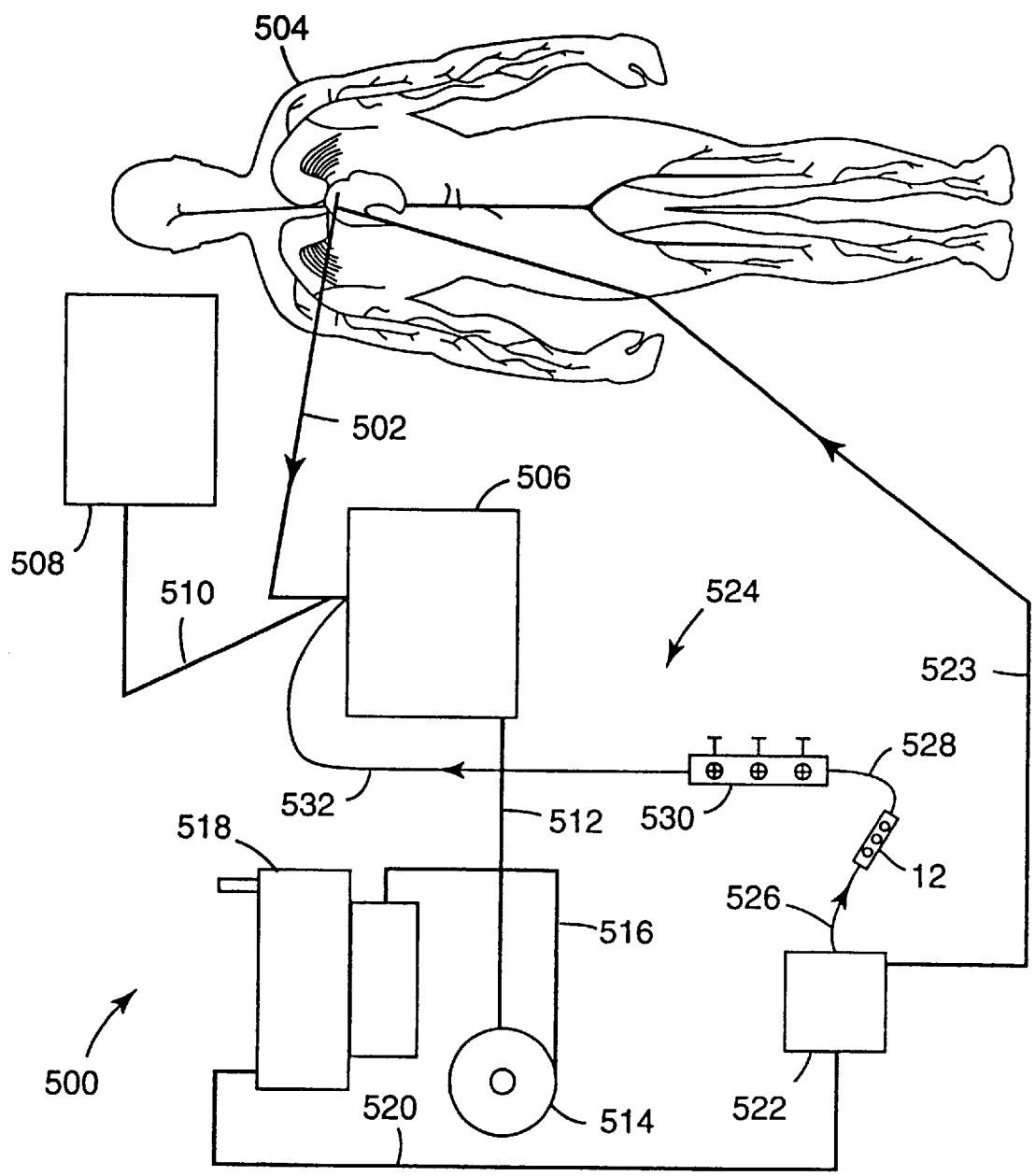
FIG. 25 is a schematic diagram of a cardiopulmonary by-pass circuit using the cassette and device of FIG. 1.

FIG. 25 is a schematic illustration of a cardiopulmonary by-pass circuit 500 that advantageously employs the measuring device 14 and the cassette 12 described above. The circuit 500 includes a first length of tubing 502 having an inlet that is placed in communication with a venous blood vessel (preferably the vena cava) of a patient 504 undergoing surgery such as open heart surgery. The tubing 502 also includes an outlet that is connected to a venous bag reservoir 506. A cardiotomy reservoir 508 is also connected by means of a second length of tubing 510 to the venous bag reservoir 506.

The circuit 500 also includes a third length of tubing 512 having an inlet that is connected to an outlet port of the venous bag reservoir 506. The third length of tubing 512 has an outlet that is connected to a peristolic or centrifugal pump 514.

The pump 514 has an outlet that is coupled to an inlet of a fourth length of tubing 516. The fourth length of tubing 516 has an outlet that is coupled to an inlet port of an oxygenator 518. The oxygenator 518 has an outlet port that is connected to an inlet of a fifth length of tubing 520.

The fifth length of tubing 520 has an outlet that is in communication with an inlet port of an arterial filter 522. An outlet port of the arterial filter 522 is connected to an inlet of a sixth length of tubing 523. The sixth length of tubing 523 also has an outlet that is connected to an arterial blood vessel (preferably the aorta) of the patient 504.

The cardiopulmonary by-pass circuit 500 also includes a shunt passageway 524. In the embodiment illustrated in FIG. 25, the shunt passageway 524 includes a sixth length of tubing 526 having an inlet that is connected to an outlet port of the arterial filter 522. The sixth length of tubing 526 also has an outlet that is connected to an inlet port of a blood parameter measurement cassette such as the cassette 12 shown in FIGS. 1–7. As an example, the sixth length of tubing 526 may be the same as the tubing 54 shown in FIG. 5.

The shunt passageway 524 also includes a seventh length of tubing 528 having an inlet that is connected to an outlet port of the cassette 12. The seventh length of tubing 528 is optionally the same as the tubing 84 that is shown in FIG. 5. The seventh length of tubing 528 also has an outlet port that is connected to an inlet port of a sampling port 530.

The shunt passageway 524 further includes an eighth length of tubing 532 having an inlet that is coupled to an outlet port of the sampling port 530. The eighth length of tubing 532 has an outlet that is connected to the inlet port of the venous bag reservoir 506 in the embodiment shown in FIG. 25. Although not shown in the drawing, the shunt passageway 524 may optionally include a valve to limit or interrupt the passage of blood through the tubing 526, 528 and 532.

The passages within the flexible tubing 502, 510, 512 and 516 as well as within the cardiotomy reservoir 508, the venous bag reservoir 506 and the pump 514 comprise a venous passageway. The passages within the flexible of tubing 520, 523 as well as within the arterial filter 522 represent an arterial passageway. The outlet of the shunt passageway 524 (i.e., the outlet of the eighth length of tubing 532 in the embodiment shown in FIG. 25) may be placed at any one of a number of different locations along the venous passageway, and is shown as connected to the inlet port of the venous bag reservoir 506 for exemplary purposes only. Preferably, the outlet of the shunt passageway 524 is placed in the venous passageway upstream of the pump 514 in order to enable blood to flow through the shunt passageway 524 without the need for an auxiliary pump.

The inlet of the shunt passageway 524 (i.e., the inlet of the sixth length of tubing 526 in the embodiment shown in FIG. 25) is preferably placed in communication with the arterial passageway at any one of a number of different locations along the latter, and more preferably is connected to an outlet port of the arterial filter 522 as depicted in FIG. 25. As another option, however, the inlet of the shunt passageway 524 may be located along the venous passageway, preferably at a location downstream of the pump 514.

In the circuit 500 shown in FIG. 25, the shunt passageway 524 diverts a portion of the patient's blood flowing through the arterial passageway and directs the diverted portion back to the venous passageway. Advantageously, placement of the cassette 12 with its sensors 28–34 along the length of the shunt passageway 524 avoids the necessity of placing the cassette 12 in series relation with either the venous passageway or the arterial passageway, and yet allows for blood to move continuously past the sensors 28–34 at all times if desired. Moreover, the shunt passageway 524 can be connected to or disconnected from the venous and arterial passageways during a surgical procedure if desired without interrupting the flow of blood through the venous passageway and arterial passageway to the patient 504.

By contrast, conventional cardiopulmonary by-pass circuits with blood gas monitoring devices have typically included a flow-through cassette or cell that is interposed in the venous or arterial passageway and has one or more sensors for determining parameters of blood flowing through the cell. However, since the flow-through cell is in series with the venous and arterial passageways, the cell must be connected to the venous or arterial passageway before blood is directed through the by-pass circuit, a disadvantage in certain instances. Such an arrangement also effectively precludes the possibility of changing the cell if, for example, one or more of the sensors is defective.

Preferably, the shunt passageway 524 has an average cross-sectional area in reference planes perpendicular to the flow of blood that is smaller than the average cross-sectional area of the venous and/or the arterial passageways in reference planes perpendicular to the flow of blood. For example, the shunt passageway 524 including the flexible tubing 526, 528 and 532 may have an internal diameter of 0.125 inch (3.2 mm), while the venous and arterial passageways including the flexible tubing 502, 512, 516, 520 and 523 may have an average internal diameter in the range of from about 0.25 inch (6.3 mm) to about 0.5 inch (12.7 mm). The smaller internal area of the shunt passageway 524 allows the use of relatively small tubing sizes which can be easily attached to or disconnected from the venous and arterial passageways at any time without undue interruption to the flow of blood through the venous and arterial passageways. For example, the shunt passageway 524 may be connected to the venous and arterial passageways some time after blood has begun to flow through the latter, as may be desired in the surgical suite. after the patient has arrived from the pre-surgical suite with the arterial and venous passageways installed and in use.

Furthermore, the shunt passageway 524 is an advantage in that the sampling port 530 can be placed in close proximity to the cassette 12 and help insure that the blood samples that are taken from the sampling port 530 better correlate with the measurement of the blood characteristics determined by the cassette 12 and the measuring device 14. This arrangement also avoids the need for a syringe or other device to withdraw blood samples from the sampling port as is the case with many conventional cardiopulmonary by-pass circuits.

The cassette 12 and the device 14 may also be used in a non-cardiopulmonary by-pass shunt application. For example, in an intensive care unit or other critical care setting, an arterial-to-venous shunt passageway could be constructed by connecting-relatively small diameter flexible tubing (e.g., 0.125 inch (3.1 mm) to 0.19 inch (4.8 mm) outer diameter) to an arterial blood vessel and a venous blood vessel using conventional cannulation techniques. Blood would then flow through the tubing due to the arterial-venous pressure differential. A cassette such as cassette 12 connected to the tubing would be used to monitor one or more parameters of the blood.

Advantageously, the longitudinal axis of the measuring device 14, and particularly the longitudinal axis of the housing 200, is generally parallel, and preferably is parallel to the direction of blood flowing through the fluid chamber 18 of the cassette 12. Such construction provides a compact assembly and further reduces the possibility of eddy currents or other disruptions in the flow of blood that might otherwise tend to facilitate clotting of the blood. The parallel arrangement is particularly useful when the cassette 12 and the measuring device 14 are placed in the vicinity of the patient's body.

Figure 26:
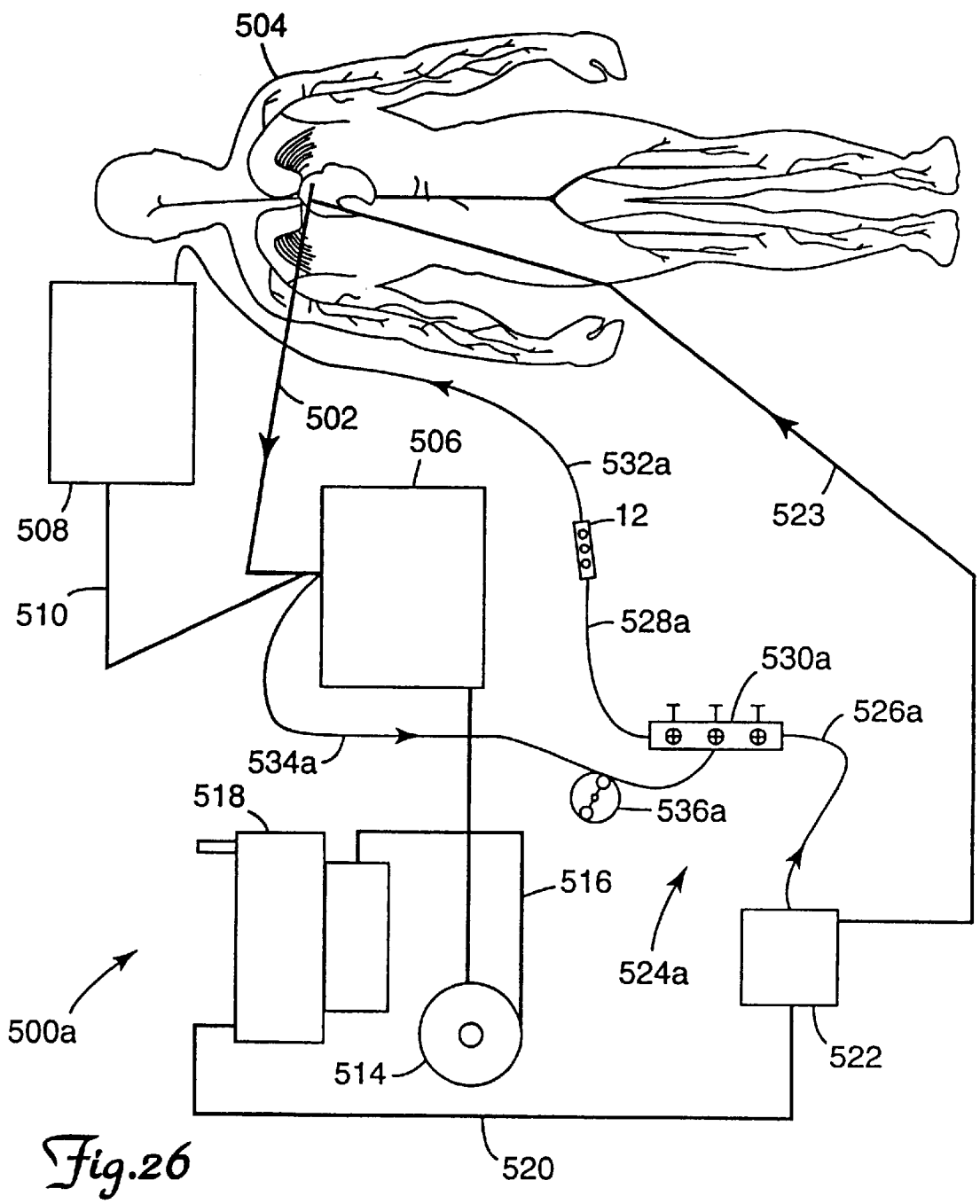
FIG. 26 is a view somewhat similar to FIG. 1 but in accordance with another embodiment of the invention.

FIG. 26 is a schematic illustration of a cardiopulmonary by-pass circuit 500a in accordance with another embodiment of the invention. In FIGS. 25 and 26, elements that are identified by the same numerals are identical and as a consequence a detailed description of those elements need not be repeated. However, the cardiopulmonary by-pass circuit 500a of FIG. 26 has a shunt passageway 524a that is somewhat different than the shunt passageway 524.

More particularly, the shunt passageway 524a includes a sixth length of tubing 526a having an inlet that is connected to the arterial filter 522 and an outlet that is connected to a sampling port 530a. The shunt passageway 524a also includes a seventh length of tubing 528a having an inlet that is connected to the sampling port 530a and an outlet that is connected to the cassette 12. An eighth length of tubing 532a of the shunt passageway 524a has an inlet that is connected to the cassette 12 and an outlet that is connected to the cardiotomy reservoir 508.

The cardiopulmonary by-pass circuit 500a also includes a ninth length of tubing 534a having an inlet that is connected to an inlet of the venous bag reservoir 506 and an outlet that is connected to the sampling port 530a. A pump 536a is interposed in the ninth length of tubing 534a for directing blood from the venous bag reservoir 506 through the ninth length of tubing 534a and to the sampling port 530a.

The sampling port 530a includes valves to selectively interrupt the flow of blood from either the sixth length of tubing 526a or the ninth length of tubing 534a. For example, the valves of the sampling port 530a may be adjusted to enable the flow of blood through the sixth length of tubing 526a and to the cassette 12 and interrupt the flow of blood in the ninth length of tubing 534a, so that the sensors 28–34 of the cassette 12 may be used to monitor the parameters of arterial blood. As another option, the valves of the sampling port 530a may be adjusted to interrupt the flow of blood through the sixth length of tubing 526a and enable the flow of blood through the ninth length of tubing 534a and to the cassette 12 so that the sensors 28–34 may be used for monitoring the parameters of venous blood. Such an arrangement enables the user to alternatively monitor both venous and arterial blood parameters without the need for two cassettes and measuring devices.

Figure 27:
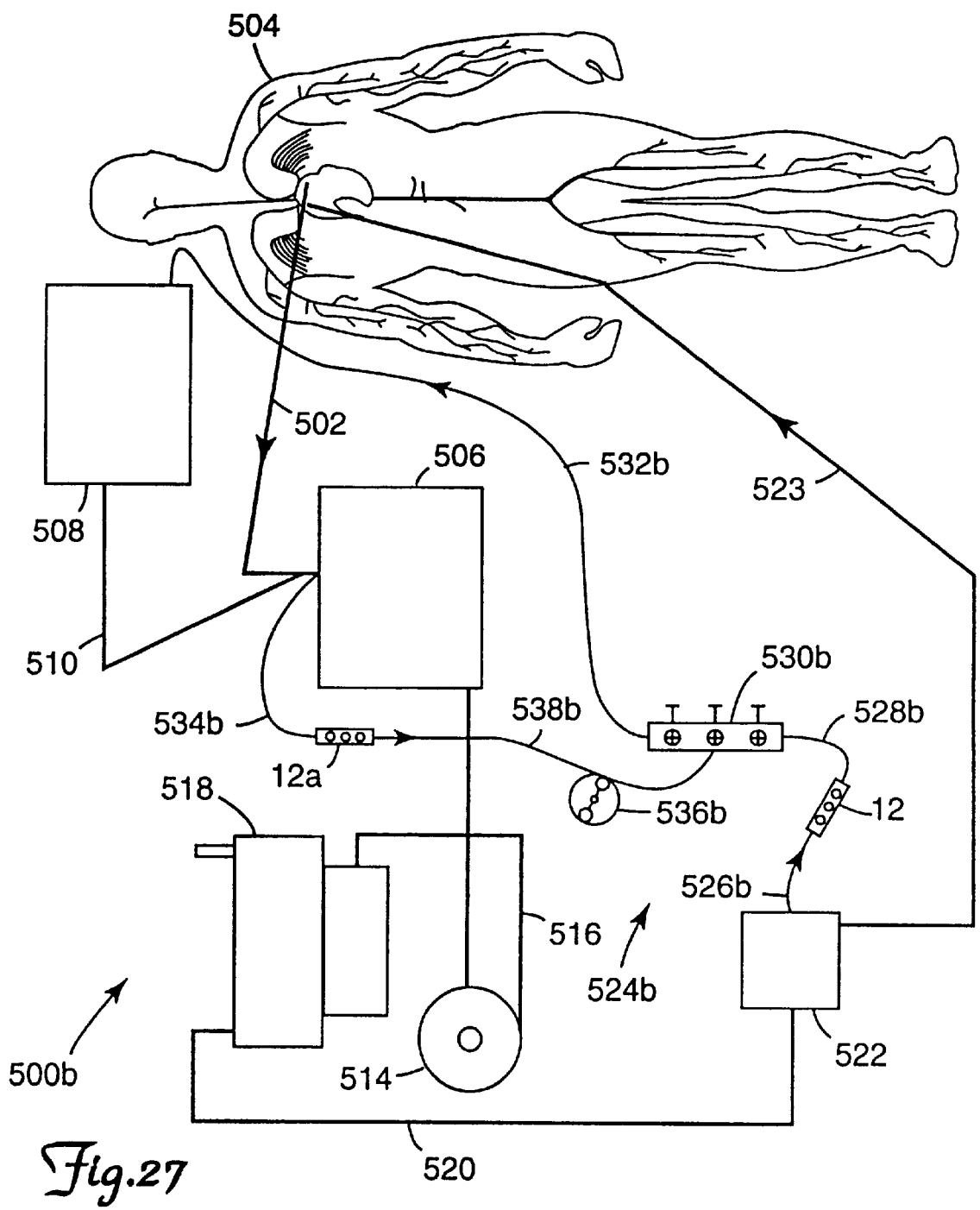
FIG. 27 is a view somewhat similar to FIG. 25 but in accordance with another embodiment of the invention.

Another alternative embodiment of the invention is schematically illustrated in FIG. 27, wherein is shown a cardiopulmonary by-pass circuit 500b. The components shown in FIGS. 25 and 27 that bear the same identifying numerals are identical and a detailed description of such components need not be repeated. However, the cardiopulmonary by-pass circuit 500b includes a shunt passageway 524b that is somewhat different than the shunt passageways 524, 524a described hereinabove.

More particularly, the shunt passageway 524b includes a sixth length of tubing 526b having an inlet that is connected to an outlet of the arterial filter 522 and an outlet that is connected to the inlet to the cassette 12. A seventh length of tubing 528b of the shunt passageway 524b has an inlet that is connected to the outlet connector 62 of the cassette 12 and an outlet that is connected to an inlet port of a sampling port 530b. An eighth length of tubing 532b of the shunt passageway 524b has an inlet that is connected to an outlet port of the sampling port 530b and an outlet that is connected to the cardiotomy reservoir 508.

Additionally, the shunt passageway 524b includes a ninth length of tubing 534b having an inlet that is connected to an inlet port of the venous bag reservoir 506 and an outlet that is connected to an inlet fitting of a second cassette 12a. Optionally, the second cassette 12a is identical to the first cassette 12. The second cassette 12a has an outlet connector (such as the Luer connector 62 shown in FIG. 5) that connects to an inlet of a tenth length of tubing 538b. The tenth length of tubing 538b has an outlet that is connected to an inlet of the sampling port 532b. A pump 536b is interposed in the tenth length of tubing 538b to direct blood from the inlet of the venous bag reservoir 506 to the sampling port 530b.

The cardiopulmonary by-pass circuit 500b that is shown in FIG. 27 enables the user to monitor characteristics of blood simultaneously in both the arterial and venous passageways. As an alternative to the circuits 500a, 500b shown respectively in FIGS. 26 and 27, the inlet of the ninth length of tubing 534a, 534b may be connected to the fourth length of tubing 516, and in such cases the pressure provided by the pump 514 is preferably sufficient to direct the flow of blood through the tubing 534a, 534b without the need for the pumps 536a, 536b.

The shunt passageways 524a, 524b, like the shunt passageway 524, preferably have an average cross-sectional area in reference planes perpendicular to the flow of blood that is smaller than the average cross-sectional area of either of the venous or arterial passageways when considered in reference planes perpendicular to the flow of blood. The shunt passageways 524a, 524b can be conveniently attached or detached from the circuits 500a, 500b respectively without interrupting the flow of blood passing through the arterial and venous passageways.

Figure 28:
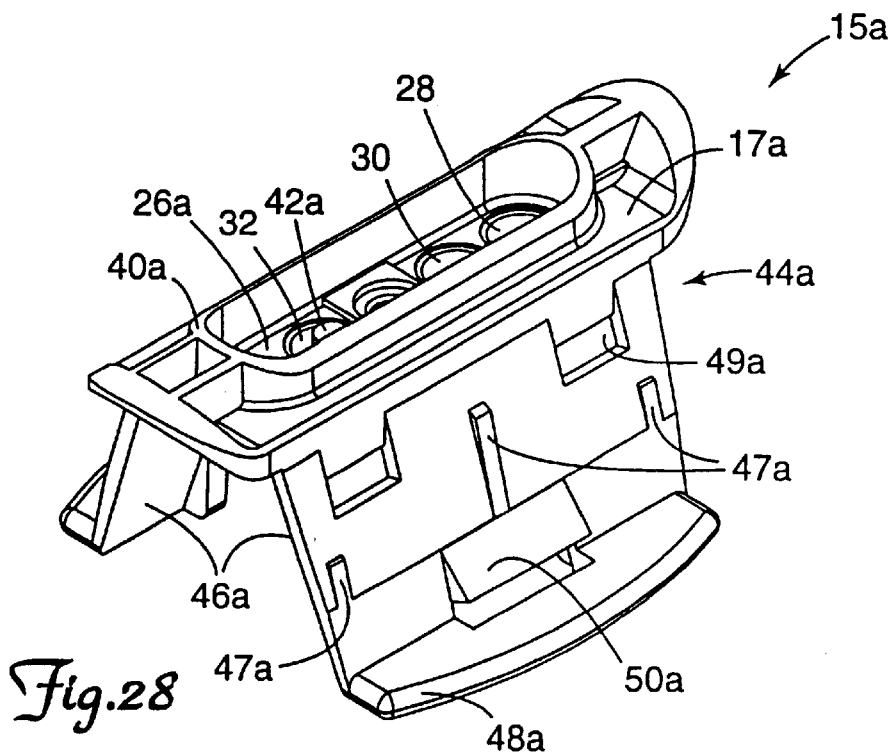
FIG. 28 is an enlarged perspective view of a body of a blood parameter measurement cassette constructed in accordance with another embodiment of the invention.
Figure 29:
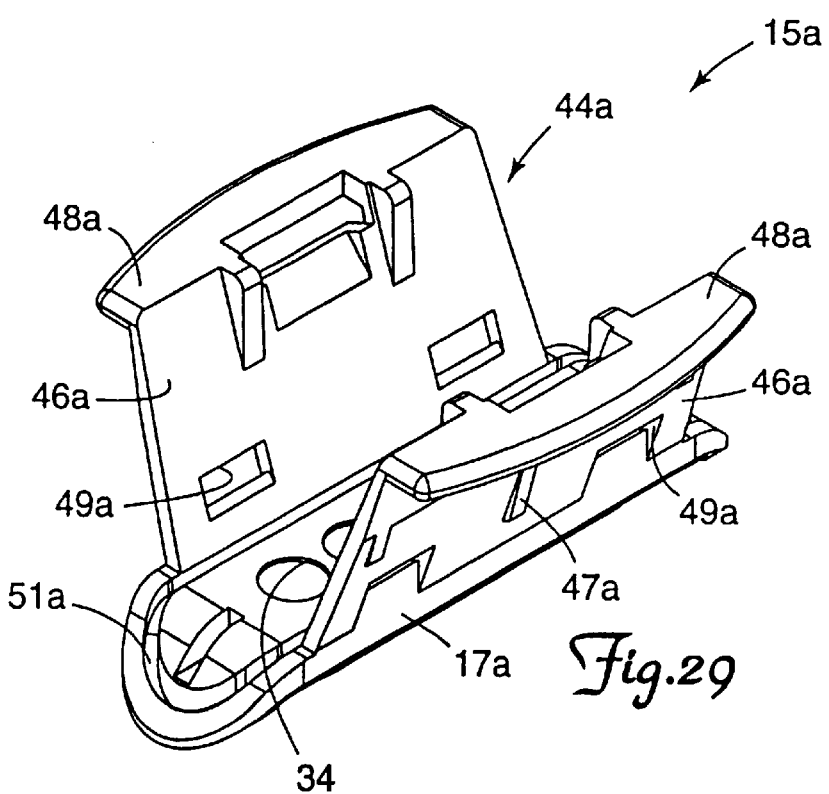
FIG. 29 is a view somewhat similar to FIG. 28 except looking in another direction toward the body.
Figure 30:
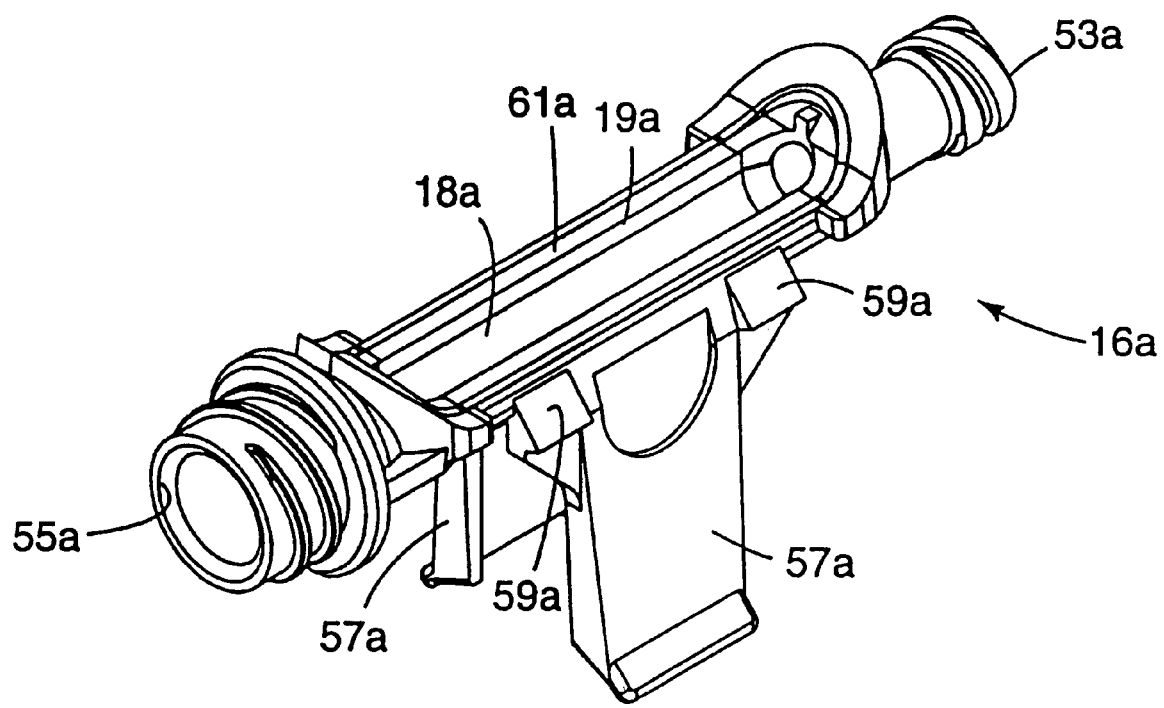
FIG. 30 is an enlarged perspective view of an exemplary cassette casing for detachable connection with the cassette body shown in FIGS. 28–29.

Cassette 12a according to another embodiment of the invention is illustrated in FIGS. 28–31 and broadly includes a cassette body 15a that is shown alone in FIGS. 28 and 29 and a cassette casing 16a that is shown alone in FIG. 30. The body 15a includes a central support member 17a for mounting one or more sensors that are adapted to sense one or more parameters in a fluid such as blood. In the embodiment shown in FIGS. 28 and 29, the support member 17a carries four sensors 28–34 that are identical to the sensors 28–34 described in connection with the cassette 12 above, although it should be understood in this regard that different sensors or a smaller or larger number of sensors may alternatively be provided.

The sensors 28–34 of the cassette body 15a are located in an oval-shaped recess 26a that is surrounded by a rim 40a. A key 42a is integrally connected to a side wall of the rim 40a as shown in FIG. 28. The recess 26a, the rim 40a and the key 42a are similar in configuration to the recess 26, the rim 40 and the key 42 described above in order to matingly and releasably couple to the protrusion 216 of the measuring device 14 when desired.

The cassette body 15a also includes a male coupling 44a for detachable connection to the female coupling 202 of the measuring device 14. The coupling 44a has a convex, generally U-shaped configuration in reference planes perpendicular to an axis extending through the center of the four sensors 28–34. The coupling 44a includes opposed leg portions 46a that extend outwardly from the body 15a in a direction away from the outward extension of the rim 40a. Each leg portion 46a includes three support sections having flat, coplanar outer surfaces 47a adapted for contact with the coupling 202. Preferably, the outer surfaces 47a of the opposed leg portions 46a converge as the body 15a is approached and extend along reference planes that are oriented in an angle in the range of about 28 degrees to about 32 degrees relative to each other. More preferably, the outer surfaces 47a extend along respective reference planes that are oriented at an angle of about 30 degrees relative to each other.

A flange 48a is integrally connected to the outer end of each leg portion 46a. Flanges 48a lie in a common plane that is parallel to the aforementioned axis extending through the center of the four sensors 28–34. The leg portions 46a are somewhat flexible and can be moved slightly toward each other under the influence of finger pressure, but also have sufficient memory to quickly and repeatedly return to their original, normal orientation as shown in the drawings once finger pressure is released.

An outer, central region of each leg portion 46a is integrally connected to a wedge-shaped tab 50a. The tabs 50a extend away from each other and outwardly from the respective leg portions 46a along respective reference planes that are oriented at an angle of about 80 degrees relative to each other. Additionally, a distal edge of each tab 50a extends in a reference plane that is oriented at an angle of 25 degrees relative to the direction of extension of the flanges 48a. Outermost edges of the tabs 50a are spaced outwardly relative to adjacent regions of the respective leg portions 46a and lie in a common reference plane that is between the body 15a and the aforementioned reference plane containing the flanges 48a.

Additionally, the leg portions 46a each have two rectangular openings 49a that are located between the body 15a and the tabs 50a, and preferably are located closely adjacent the body 15a. Additionally, the cassette body 15a has a groove 51a a as illustrated in FIG. 29 for receiving an O-ring 51a a that is depicted only in FIG. 31.

The cassette casing 16a that is shown alone in FIG. 30 has walls defining a chamber 18a, an inlet 53a for admitting a fluid such as blood to the chamber 18a and an outlet 55a for discharging fluid from the chamber 18a. The casing 16a has a side opening 19a that is surrounded by a wall 61a and extends into the chamber 18a. The casing 16a also includes a pair of elongated wings 57a that extend outwardly in a direction away from the chamber 18a. Two snaps or ears 59a, each having a protruding, wedge-shaped configuration, are connected to each wing 57a at a location next to the chamber 18a.

The wings 57a are somewhat flexible and can be moved slightly toward each other under the influence of finger pressure, but also have sufficient memory to quickly and repeatedly return to their original, normal orientation as shown in the drawings once finger pressure is released. Preferably, the cassette body 15a and the cassette casing 16a are each injection-molded as initially separate pieces of a plastic material such as relatively clear medical grade polycarbonate.

The ears 59a of the casing wings 57a and the openings 49a of the cassette body 15a constitute a connector for detachably coupling the casing 16a to the body 15a. The body 15a and the casing 16a are shown coupled together in FIG. 31, where it can be observed that each of the ears 59a are received in a respective one of the openings 49a to securely couple the casing 16a to the body 15a. When the casing 16a is so connected to the body 15a, the O-ring 51a (FIG. 31) engages the wall 61a (FIG. 30) of the casing 16a in order to close the opening 19a and provide a leak-resistant fluid seal between the body 15a and the casing 16a.

Advantageously, the wedge-shaped configuration of the ears 59a functions as a cam to deflect the respective wings 57a inwardly and in a direction toward each other as the ears 59a slide across the inner surfaces of the leg portions 46a when the casing 16a is coupled to the body 15a. As such, the user can securely couple the casing 16a to the body 15a by pressing on the casing 16a adjacent the fluid chamber 18a, and the user need not squeeze the wings 57a together. Once the outer edges of the ears 59a are moved past the outer sides of the openings 49a, the inherent resiliency of the wings 57a causes the ears 59a to snap in place in the openings 49a. However, the casing 16a may be detached from the body 15a when desired by pressing the wings 57a toward each other until such time as the outer edges of the ears 59a clear the openings 49a, and then moving the casing 16a away from the body 15a.

Figure 31:
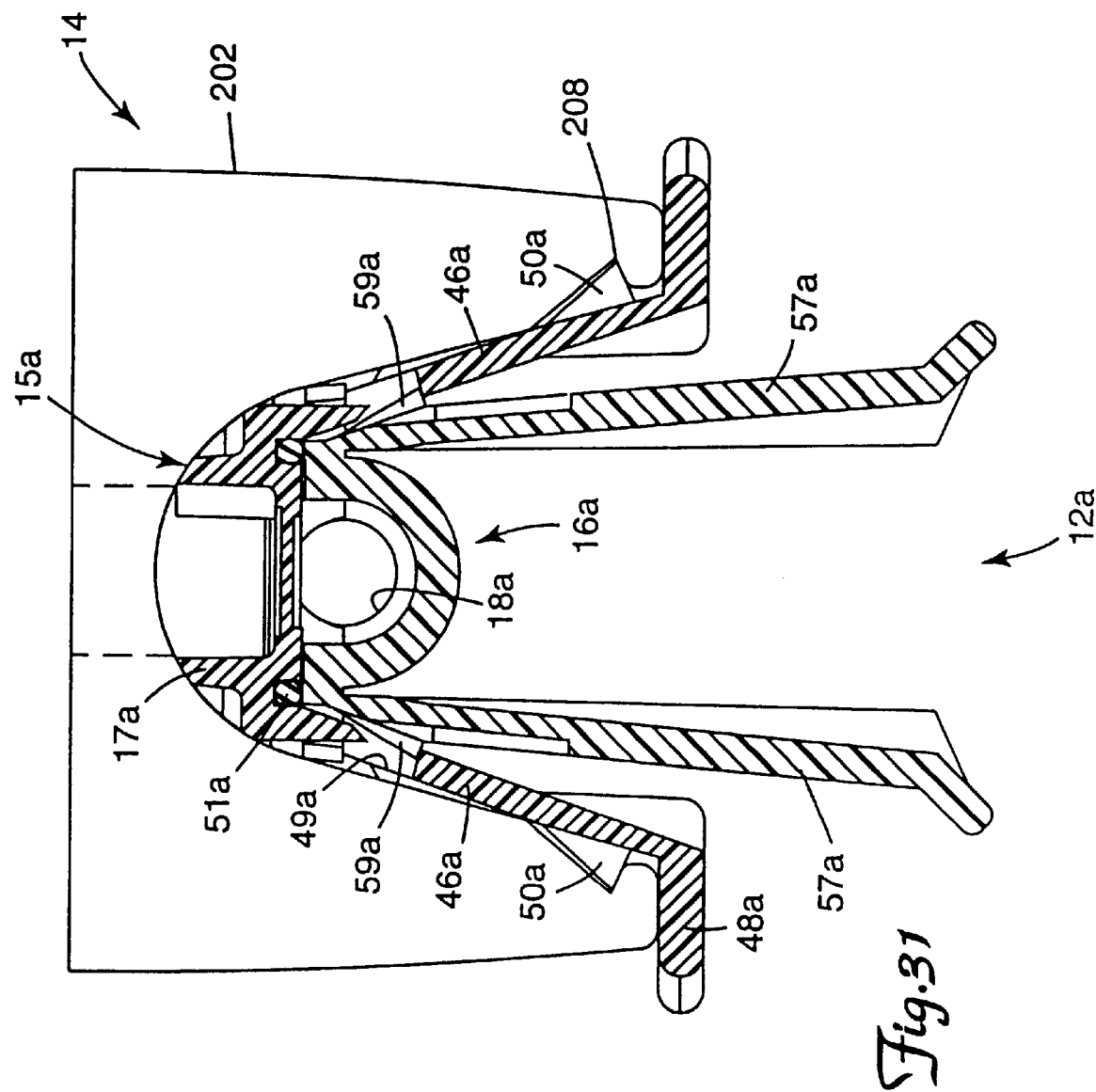
FIG. 31 is an enlarged end cross-sectional view of the cassette casing of FIG. 30 shown as attached to the cassette body of FIGS. 28–29, and additionally illustrating a coupling of the blood parameter measuring device of FIG. 1 coupled to the cassette.

FIG. 31 also illustrates connection of the cassette 12a to the female coupling 202 of the measuring device 14 described above. The tabs 50a snap into respective grooves 208 of the coupling 202 as the cassette 12a is moved toward the measuring device 14. In this regard, the tabs 50a are similar in function and operation to the tabs 50, and provide a snap-action connection to releasably couple the cassette 12a to the measuring device 14. When it is desired to detach the cassette 12a from the measuring device 14, the flanges 48a are moved inwardly by finger pressure toward each other until such time as the tabs 50a clear the grooves 208, and the cassette 12a may then be removed from the female coupling 202.

In other respects, the cassette 12a is similar in construction and function to the cassette 12. For example, the cassette 12a is used for calibration purposes and may be also used if desired for monitoring parameters of blood. As another example, internal walls of the cassette 12a defining the chamber 18a are preferably provided with a hydrophilic surface such as a coating of heparin. The chamber 18a also preferably includes chamber portions similar to the portions 20, 22, 24 and 25 described above.

Additionally, various fittings and connectors may be coupled to the inlet 53a and the outlet 55a for connection with flexible tubing. Alternatively, a cap such as cap 56 may be connected to the outlet port 55a, and a gas filter assembly similar to the filter assembly 66 may be coupled to the inlet 53a. Such an assembly enables the user to calibrate the sensors 28–34 in the manner similar to the procedure described above for the cassette 12.

Figure 32:
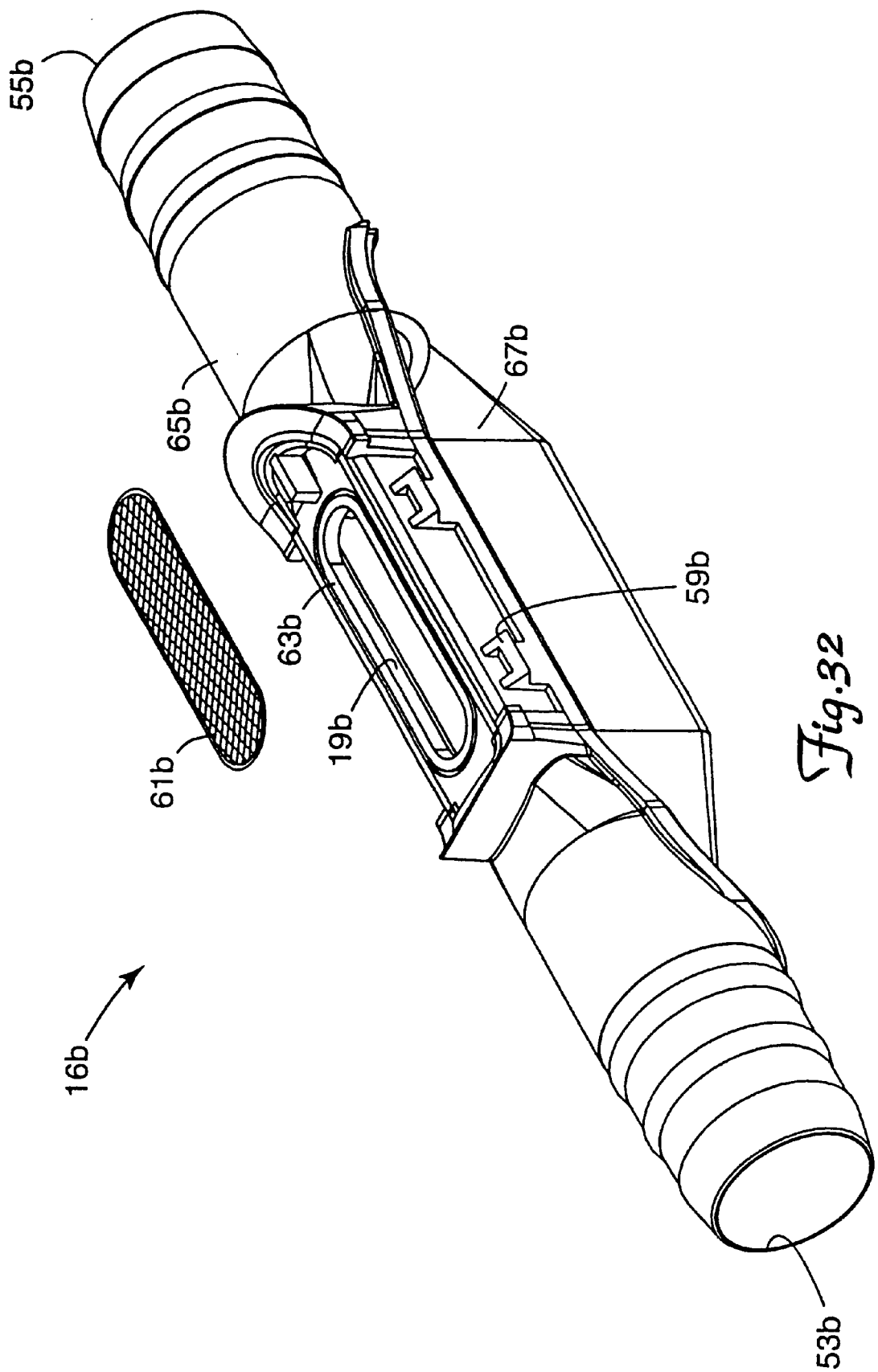
FIG. 32 is an enlarged perspective view in partially exploded form of another cassette casing that can be attached to the cassette body shown in FIGS. 28–29 if desired to present a somewhat larger cross-sectional area for the passage of blood.
Figure 33:
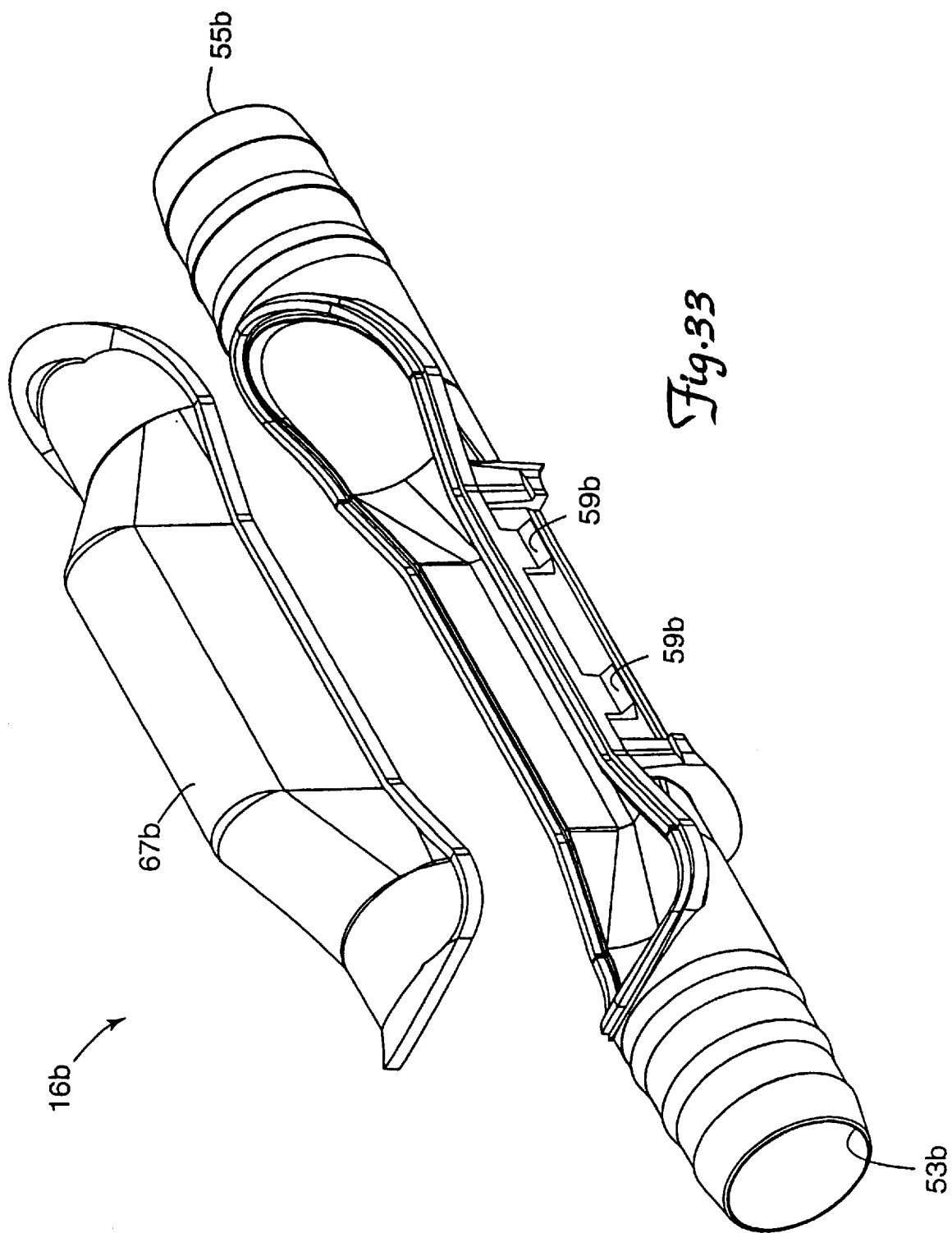
FIG. 33 is a view somewhat similar to FIG. 32 except taken in another direction toward the cassette casing and depicting another part of the casing in exploded form.

The cassette casing 16a has a relatively small internal diameter and is used during calibration. Optionally, the casing 16a may also be used when the cassette 12a forms part of a shunt passageway such as the shunt passageway 524, 524a, 524b in FIGS. 25–27. An alternative cassette casing 16a is illustrated in FIGS. 32 and 33, and is useful where the cassette 12a is to be used as a flow-through cell for sensing in an arterial or a venous passageway. For example, the casing 16b may have an inlet 53a and an outlet 55b that is adapted to receive flexible tubing having a nominal inner diameter of 0.5 inch (12.5 mm).

The casing 16b includes four wedge-shaped snaps or ears 59b which are located in pairs along opposite sides of an oval-shaped opening 19b. The ears 59b have the same spatial relationship to each other as the ears 59a described above, and are adapted to be snapped into the openings 49a of the cassette body 15a when the casing 16b is connected to the body 15a. However, since the ears 59b are not coupled to wings such as the wings 59a, the ears 59b serve to connect the casing 16b to the body 15a in substantially permanent fashion and as a consequence the casing 16b cannot readily be detached from the body 15a once coupled together.

The casing 16b has an internal fluid chamber 18b with a side opening 19b. An oval-shaped membrane 61b extends across the opening 19b and is joined to a oval-shaped land 63b. The membrane 61b is connected to the land 63b by ultrasonic welding or adhesive bonding. The membrane 61b is made of material having a series of small perforations such as 0.005 inch (0.12 mm) track-etched polycarbonate.

Aside from the membrane 61b, the cassette casing 16b is made using two initially separate pieces: a first piece 65b and a second piece 67b as shown in FIG. 33. The first and second pieces 65b, 67b are joined together using, for example, an ultrasonic welding or an adhesive bonding procedure.

Figure 34:
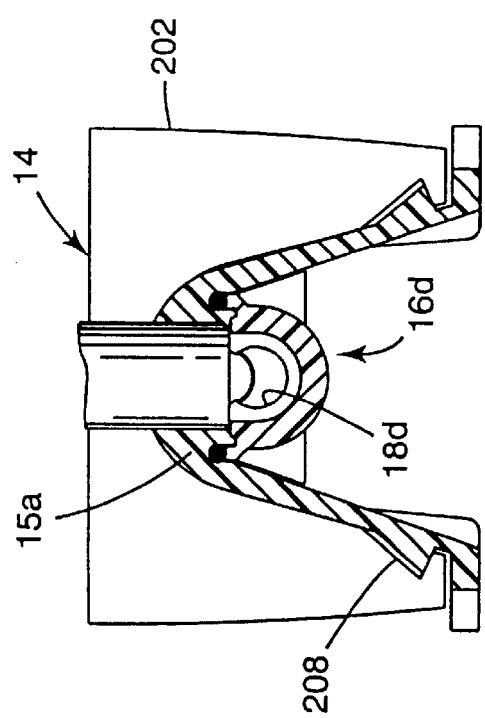
FIG. 34 is a view somewhat similar to FIG. 31 except showing the cassette casing of FIGS. 32–33 in place of the cassette casing of FIG. 30.

FIG. 34 is an end cross-sectional view through the casing 16b, the body 15a and the female coupling 202 of the measuring device 14. As can be observed in FIG. 34, the configuration of the fluid chamber 18b in the vicinity of the sensors 28–34 is generally oval-shaped, an advantage in that a somewhat larger chamber area can be provided within the confines of the leg portions 46a. The cross-sectional area of the generally oval-shaped portion of the fluid chamber 18b shown in FIG. 34 is approximately equal, and preferably equal, to the circular cross-sectional area of the inlet 53b and the outlet 55b. Moreover, wall sections defining the fluid chamber 18b so preferably provide a smooth transition between the circular cross-sectional areas and the middle, generally oval-shaped area to avoid undue disruption of the flow of blood through the chamber 18b.

Figure 35:
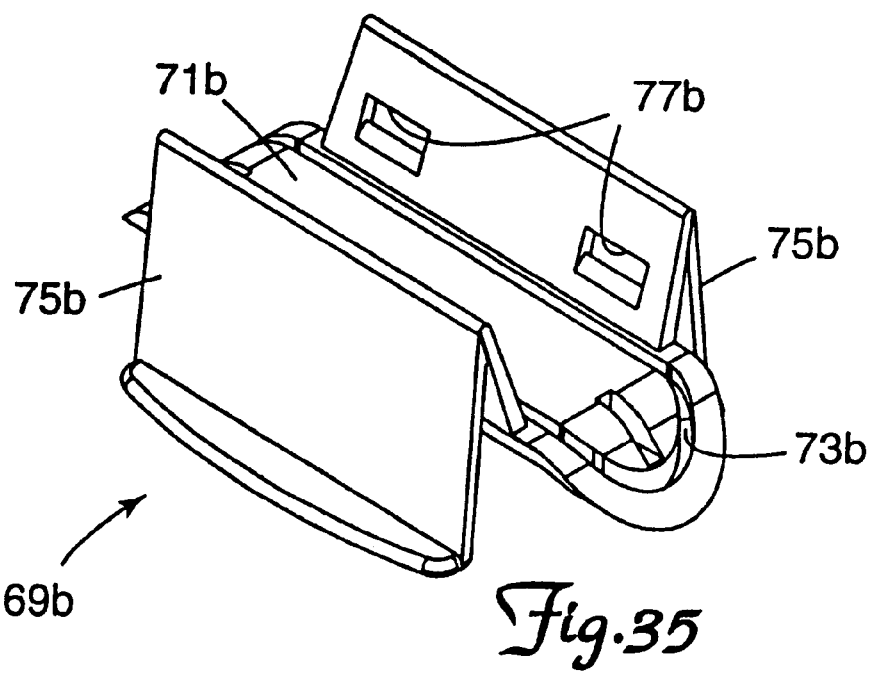
FIG. 35 is an enlarged perspective view of a shipping cap for use with the cassette casing of FIGS. 32–33.
Figure 36:
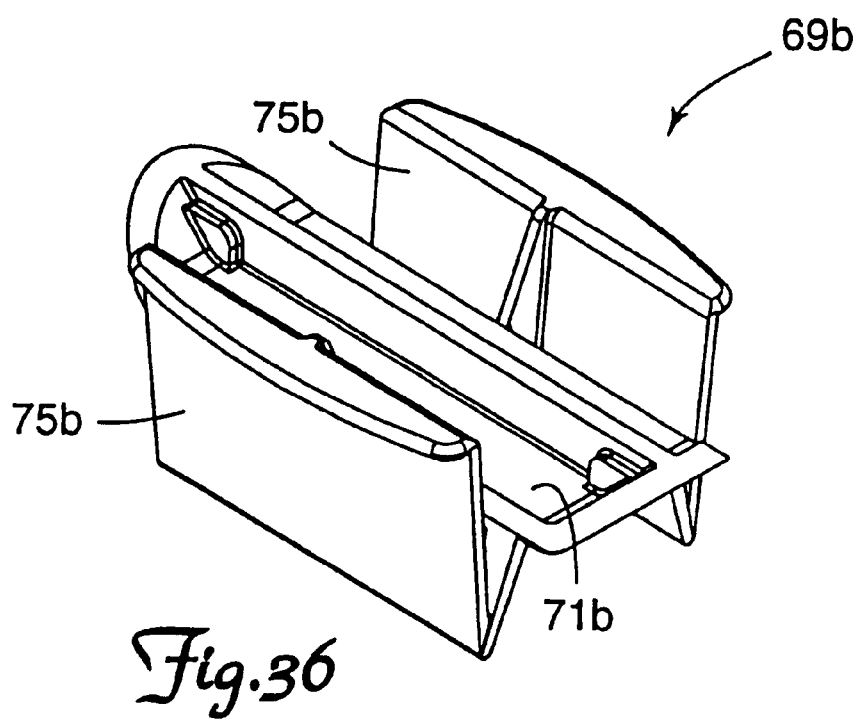
FIG. 36 is a view somewhat similar to FIG. 35 except looking in another direction toward the cap.

FIGS. 35 and 36 depict a cap 69b adapted for use with the casing 16b. The cap 69b includes a central, generally oval-shaped member 71b that is adapted to extend over and protect the membrane 61b before such time as the casing 16b is connected to the body 15a. Preferably, the member 71b has a shape complemental in configuration to the membrane 61b when the membrane 61b is fixed to the casing 16b. The cap 69b also has a groove 73b to carry an O-ring (not shown) for sealing engagement with the casing 16b in order to establish a hermetic seal over the membrane 61b.

The cap 69b includes a pair of flexible wings 75b, each of which has a pair of rectangular openings 77b as shown in FIG. 35. As the cap 69b is pressed onto the casing 16b, the wings 75b engage the wedge-shaped ears 59b and deflect outwardly in a direction away from each other. Once the ears 59b are moved to a position adjacent respective openings 77b, the inherent resiliency of the wings 75b causes the wings 75b to self-return to their normal orientation as shown in FIGS. 35 and 36 to securely couple the cap 69b to the casing 16b. The cap 69b may be easily detached from the casing 16b when desired by pressing the wings 75b in a direction toward each other until the ears 59b clear the openings 77b and then moving the cap 69b away from the casing 16b.

Figure 38:
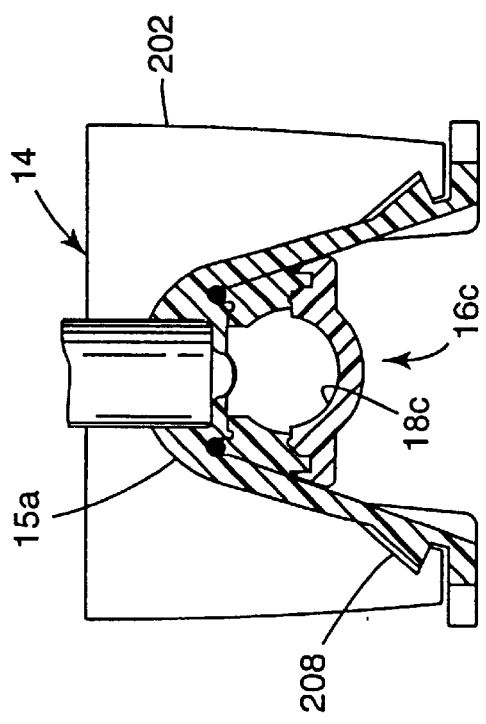
FIG. 38 is a view somewhat similar to FIG. 34 except showing another cassette casing that is coupled to the cassette body in accordance with yet another embodiment of the invention.
Figure 37:
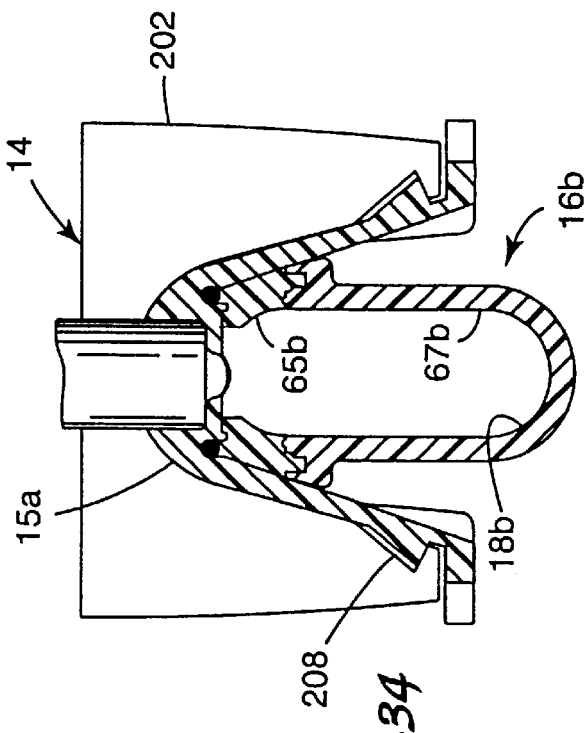
FIG. 37 is a view somewhat similar to FIG. 34 except showing another cassette casing that is connected to the cassette body in accordance with another embodiment of the invention.

FIGS. 37 and 38 illustrate for exemplary purposes two other casings for use with the body 15a. In FIG. 37, for example, a casing 16c includes a first piece 65c and a second piece 67c that together with the cassette body 15a present a fluid chamber 18c. The fluid chamber 18c has a generally circular cross-sectional area along its entire length. Since the chamber 18c is smaller in area than, for example, the cross-sectional area of the chamber 18b shown in FIG. 34, the need for an oval-shaped middle portion of the chamber 18c is avoided. In other respects, the casing 16c is similar to the casing 16b. For example, the casing 16c has a membrane similar to membrane 61b.

As an example of use of the cassette 12a, the body 15a is preferably coupled to the casing 16a and then shipped to the user in such coupled-together relation. Additionally, a gas filter assembly such as assembly 66 (see, e.g., FIG. 5) is connected to the cassette 12a along with a fitting and cap such as fitting 56 and cap 78 (see, e.g., FIG. 6). The user then connects the gas filter assembly to a source of calibration gas, and loosens the cap. The calibration gas is then directed through the fluid chamber 18a in the manner described above with regard to calibration of the cassette 12.

Once calibration is complete, the casing 16a is removed from the body 15a by squeezing the wings 57a toward each other. During such time, the body 15a preferably remains connected to the coupling 202 of the measuring device 14. Next, the cap 69b is removed from the selected casing 16b or 16c. If, for example, the cassette 12a is intended to be used in an arterial or a venous passageway having lengths of tubing with an internal nominal diameter of 0.5 inch (12.5 mm), the casing 16b is connected to the body 15a in the manner shown in FIG. 34. Once the procedure is completed, the body 15a with the casing 16b is removed from the coupling 202 and discarded. On the other hand, if the cassette 12a is intended for use in a smaller passageway, the casing 16c is coupled to the body 15a in the manner illustrated in FIG. 37.

Advantageously, the membrane 61b enables the user to connect the casing 16b to an arterial or venous passageway before such time as the body 15a is coupled to the casing 16b. As a consequence, the casing 16b may be used to pass fluid along the arterial and venous passageways without interruption of the blood flow to begin monitoring.

The cassette assembly that is shown in FIG. 38 includes the body 15a as mentioned above, but in this instance the body 15a is coupled to a casing 16b that is advantageously a unitary, single component with the exception of a membrane that is similar to membrane 61b. The cross-sectional area of a fluid chamber 18d of the cassette 12a shown in FIG. 38 is substantially the same as the area of the fluid chamber 18a depicted in FIG. 31, and as such the cassette 12a as depicted with the casing 16d in FIG. 38 is conveniently adapted for use with a shunt passageway such as passageway 524 in FIGS. 25–27. The casing 16d is useful in instances where, for example, the manufacturer wishes to ship a single unit that will be used for both calibration and blood monitoring, and lacks wings (such as wings 57*a* in FIG. 31) to reduce the likelihood that the body 15*a* will detach from the casing 16*b* in use. In other respects, the casing 16*d* is similar to the casings 16*b*, 16*c* and has, among other things, ears similar to ears 59*b* for coupling the casing 16*d* to the body 15*a*. In addition, the shipping cap 69*b* may be used with the casings 16*c*, 16*d* as desired.

What is claimed is:

1. A device for measuring one or more parameters of blood comprising:
   a housing having a coupling for releasable connection to a blood parameter measurement cassette;
   at least one light source;
   a first plurality of optical fibers optically coupled to said at least one light source and extending toward said coupling for directing light toward the cassette, said first plurality of optical fibers having a certain cross-sectional area adjacent said coupling;
   at least one light detector;
   a second plurality of optical fibers optically coupled to said at least one light detector and extending toward said coupling for receiving light from the cassette, said second plurality of optical fibers having a cross-sectional area adjacent said coupling that is in the range of about two to about four times said certain cross-sectional area of said first plurality.

2. The device of claim 1 wherein said second plurality of optical fibers has a cross-sectional area adjacent said coupling that is about three times said certain cross-sectional area of said first plurality.

3. The device of claim 1 including a second light source, a third plurality of optical fibers optically coupled to said second light source, a second light detector, and a fourth plurality of optical fibers optically coupled to said second light detector.

4. The device of claim 1 including a signal converter fixed to said housing and connected to said at least one light detector, said signal converter providing an output signal that varies in response to the quantity of light detected by said at least one light detector.

5. The device of claim 4 wherein said signal converter comprises at least one analog to digital signal converter.

6. The device of claim 4 wherein said output signal is an electrical output signal.

7. The device of claim 4 wherein said output signal is a telemetric output signal.

8. The device of claim 1 wherein said housing surrounds said at least one light source, said at least one light detector, said first plurality of optical fibers and said second plurality of optical fibers.

9. The device of claim 1 including an optical reference material, a first reference optical pathway for directing a portion of the light from said at least one light source toward said reference material and a second reference optical pathway for directing at least a portion of the light from said reference material toward said at least one light detector.

10. The device of claim 1 wherein said at least one light source comprises a solid state light source.

11. The device of claim 1 wherein said housing has a longitudinal axis, and wherein said first plurality of optical fibers and said second plurality of optical fibers extend along respective, generally 90 degree paths that include a portion generally parallel to said longitudinal axis and a portion generally perpendicular to said longitudinal axis.

* * * * *